US009868767B2

(12) United States Patent
Pei et al.

(10) Patent No.: US 9,868,767 B2
(45) Date of Patent: Jan. 16, 2018

(54) CHEMICAL SYNTHESIS AND SCREENING OF BICYCLIC PEPTIDE LIBRARIES

(71) Applicant: OHIO STATE INNOVATION FOUNDATION, Columbus, OH (US)

(72) Inventors: Dehua Pei, Columbus, OH (US); Punit Upadhyaya, Columbus, OH (US); Wenlong Lian, Columbus, OH (US); Thi Trinh, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 38 days.

(21) Appl. No.: 14/893,203

(22) PCT Filed: May 23, 2014

(86) PCT No.: PCT/US2014/039332
§ 371 (c)(1),
(2) Date: Nov. 23, 2015

(87) PCT Pub. No.: WO2014/190257
PCT Pub. Date: Nov. 27, 2014

(65) Prior Publication Data
US 2016/0115202 A1 Apr. 28, 2016

Related U.S. Application Data

(60) Provisional application No. 61/826,805, filed on May 23, 2013.

(51) Int. Cl.
A61K 38/12 (2006.01)
C07K 5/00 (2006.01)
C07K 7/00 (2006.01)
C07K 16/00 (2006.01)
C07K 17/00 (2006.01)
C07K 7/64 (2006.01)
C07K 5/02 (2006.01)
C07K 5/09 (2006.01)
C07K 5/078 (2006.01)
A61K 38/00 (2006.01)

(52) U.S. Cl.
CPC .............. C07K 7/64 (2013.01); C07K 5/0202 (2013.01); C07K 5/06156 (2013.01); C07K 5/0817 (2013.01); A61K 38/00 (2013.01)

(58) Field of Classification Search
CPC ........... A61K 38/12; C07K 17/00; C07K 7/50
See application file for complete search history.

(56) References Cited

U.S. PATENT DOCUMENTS

2010/0292148 A1   11/2010   Krippner et al.

FOREIGN PATENT DOCUMENTS

EP    2420255       2/2012
WO    2009098450    8/2009

OTHER PUBLICATIONS

Alzani, R. et al. Suramin induces deoligomerization of human tumor necrosis factor alpha. J. Biol. Chem. 268, 12526-12529 (1993).
Angelini, Alessandro, et al. "Bicyclic peptide inhibitor reveals large contact interface with a protease target." ACS chemical biology 7.5 (2012): 817-821.
Ardi, V. C., Alexander, L. D., Johnson, V. A. & McAlpine, S. R. Macrocycles that inhibit the binding between heat shock protein 90 and TPR-containing proteins. ACS Chem. Biol. 6, 1357-1366 (2011).
Beste, G. et al. Small antibody-like proteins with prescribed ligand specificities derivedfrom the lipocalin fold. Proc. Natl. Acad. Sci. USA 96, 1898-1903 (1999).
Beutler, B. et al. Purification of cachectin, a lipoprotein-lipase suppressing hormone secreted by endotoxin-induced RAW 264.7 cells. J. Exp. Med. 161, 984-995 (1985).
Buller, F., Zhang, Y., Scheuermann, J., Schafer, J., Buhlmann, P. & Neri, D. Discovery of TNF inhibitors from a DNA-encoded chemical library based on Diels-Alder cycloaddition. Chem. Biol. 16, 1075-1086 (2009).
Chan, D. S. et al. Structure-based discovery of natural-product-like TNF-ainhibitors. Angew. Chem. Int. Ed. Engl. 49, 2860-2864 (2010).
Chen, G. & Goedde!, D. V. TNF-RI signaling: a beautiful pathway. Science 296, 1634-1635 (2002).
Chen, X., Tan, P. H., Zhang, Y. & Pei, D. On-bead screening of combinatorial libraries: Reduction of nonspecific binding by decreasing surface ligand density. J. Comb. Chem. 11, 604-611 (2009).
Chen, S., Morales-Sanfrutos, J., Angelini, A., Cutting, B. & Heinis, C. Structurally diverse cyclization linkers impose different backbone conformations in bicyclic peptides. ChemBioChem. 13, 1032-1038 (2012).
Choi, H., Lee, Y., Park, H. & Oh, D-S. Discovery of the inhibitors of tumor necrosis factor alpha with structure-based virtual screening. Bioorg. Med. Chem. Lett. 20, 6195-6198 (2010).
Dewan, V. et al. Cyclic peptide inhibitors of HIV-I capsid-human lysyl-tRNA synthetase interaction. ACS Chem. Biol. 7, 761-769 (2012).
Esposito, E. & Cuzzocrea, S. TNF-alpha as a therapeutic target in inflammatory diseases, ischemia-reperfusion injury and trauma. Curr. Med. Chem. 16, 3152-3167 (2009).

(Continued)

Primary Examiner — Kaipeen Yang
(74) Attorney, Agent, or Firm — Meunier Carlin & Curfman LLC

(57) ABSTRACT

Disclosed herein are bicyclic peptide compounds, compositions comprising same, methods for making same, and libraries comprising same. The disclosed compounds, in various aspects, are useful for treating a variety of disorders, including inflammatory disorders, autoimmune disorders, and disorders of uncontrolled cellular proliferation. This abstract is intended as a scanning tool for purposes of searching in the particular art and is not intended to be limiting of the present invention.

19 Claims, 35 Drawing Sheets

(56) References Cited

OTHER PUBLICATIONS

Furka, A., Sebestyen, F., Asgedom, M. & Dibo, G. General method for rapid synthesis of multicomponent peptide mixtures. Int. J. Pep. Prat. Res. 37, 487-493 (1991).

He, M. M. et al. Small-molecule inhibition of TNF-a. Science 310, 1022-1025 (2005).

Heinis, C., Rutherford, T., Freund, S. & Winter, G. Phage-encoded combinatorial chemical libraries based on bicyclic peptides. Nat. Chem. Biol. 5, 502-507 (2009).

Hintersteiner, M. et al. Single bead labeling method for combining confocal fluorescence on-bead screening and solution validation of tagged one-bead one-compound libraries. Chem. Biol. 16, 724-735 (2009).

Houghten, R. A et al. Generation and use of synthetic peptide combinatorial libraries for basic research and drug discovery. Nature 354, 84-86 (1991).

Hu, B. H., Jones, M. R. & Messersmith, P. B. Method for screening and MALDI-TOF MS sequencing of encoded combinatorial libraries. Anal. Chem. 79, 7275-7285 (2007).

International Search Report and Written Opinion of the U.S. International Searching Authority from International Application No. PCT/US2014/039332, mailed Dec. 3, 2014, 11 pages.

Joo, S. H., Xiao, Q., Ling, Y., Gopishetty, B. & Pei, D. High-throughput sequence determination of cyclic peptide library members by partial Edman degradation/mass spectrometry. J. Am. Chem. Soc. 128, 13000-13009 (2006).

Kawakami, M., & Cerami, A. Studies of endotoxin-induced decrease in lipoprotein-lipase activity. J. Exp. Med. 154, 631-639 (1981).

Khabar, K. S., Siddiqui, S. & Armstrong, J. A. WEHI-13V AR: a stable and sensitive variant of WEHI 164 clone 13 fibrosarcoma for tumor necrosis factor bioassay. Immunol. Lett. 46, 107-110 (1995).

Kodadek, T. & Bachhawat-Sikder, K. Optimized protocols for the isolation of specific protein-binding peptides or peptoids from combinatorial libraries displayed on beads. Mol. BioSyst. 2, 25-35 (2006).

Koide, A. et al. The fibronectin type III domain as a scaffold for novel binding proteins. J. Mol. Biol. 284, 1141-1151 (1998).

Lam, K. S. et al. A new type of synthetic peptide library for identifying ligand-binding activity. Nature 354, 82-84 (1991).

Leduc, A. M. et al. Helix-stabilized cyclic peptides as selective inhibitors of steroid receptor-coactivator interactions. Proc. Natl. Acad. Sci. USA 100, 11273-11278 (2003).

Leung, C. H. et al. Structure-based repurposing of FDA-approved drugs as TNF-a inhibitors. ChemMedChem 6, 765-768 (2011).

Liu, R., Maril<:, J. & Lam, K. S. A novel peptide-based encoding system for "one-bead one-compound" peptidomimetic and small molecule combinatorial libraries. J. Am. Chem. Soc. 124, 7678-7680 (2002).

Liu, X.,Chen, C. & Hop, C. E. Do we need to optimize plasma protein and tissue binding in drug discovery? Curr. Top. Med. Chem. 11, 450-466 (2011).

Liu, T., Qian, Z., Xiao, Q. & Pei, D. High-throughput screening of one-bead-one compound libraries: identification of cyclic peptidyl inhibitors against calcineurin/NF AT interaction. ACS Comb. Sci. 13, 537-546 (2011).

Mancini, F., Toro, C. M., Mabilia, M., Giannangeli, M., Pinza, M. & Milanese, C. Inhibition of tumor necrosis factor-a (TNF-a)-TNF-a receptor binding by structural analogues of suramin. Biochem. Pharmacol. 58, 851-859 (1999).

Martin, T. L., Mufson, E. J. & Mesulam, M. M. The light side of horseradish peroxidase histochemistry. J. Histochem. Cytochem. 32, 793 (1984).

Millward, S.W., Fiacco, S., Austin, R.J. & Roberts, R.W. Design of cyclic peptides that bind protein surfaces with antibody-like affinity. ACS Chem. Biol. 2, 625-634 (2007).

Rutledge, S.E., Volkman, H.M. & Schepartz, A. Molecular recognition of protein surfaces: high affinity ligands for the CBPKIX domain. J. Am. Chem. Soc. 125, 14336-14347 (2003).

Saito, H. et al. A tumor necrosis factor receptor loop peptide mimic inhibits bone destruction to the same extent as anti-tumor necrosis factor monoclonal antibody in murine collagen-induced arthritis. Arthritis Rheum. 56, 1164-117 4 (2007).

Sako, Y., Morimoto, J., Murakami, H. & Suga, H. Ribosomal synthesis of bicyclic peptides via two orthogonal inter-side-chain reactions. J. Am. Chem. Soc. 130, 7232-7234 (2008).

Scholl, Markus, Zuzana Kadlecova, and Harm-Anton Klok. "Dendritic and hyperbranched polyamides." Progress in Polymer Science 34.1 (2009): 24-61.

Steiner, D., Forrer, P. & Plueckthun, A. Efficient selection of DARPins with subnanomolar affinities using SRP phage display. J. Mol. Biol. 382, 1211-1227 (2008).

Sun, Y., Lu, G. & Tam, J. P. A thioester ligation approach to amphipathic bicyclic peptide library. Org. Lett. 3, 1681-1684 (2001).

Sweeney, M. C et al. Decoding protein-protein interactions through combinatorial chemistry: sequence specificity of SHP-1, SHP-2, and SHIP SH2 domains. Biochemistry 44, 14932-14947 (2005).

Takasaki,W., Kajino, Y., Kajino, K., Murali, R. & Greene, M. I. Structure-based design and characterization of exocyclic peptidomimetics that inhibit TNF alpha binding to its receptor. Nat. Biotechnol. 15, 1266-1270 (1997).

Tavassoli, A., Lu, Q., Garn, J., Pan, H., Benkovic, S. J., & Cohen, S. N. Inhibition of HN budding by a genetically selected cyclic peptide targeting the Gag-TSG 101 interaction. ACS Chem. Biol. 3, 757-764 (2008).

Thakkar, A., Wavreille, A-S. & Pei, D. Traceless capping agent for peptide sequencing by partial Edman degradation and mass spectrometry. Anal. Chem. 78, 5935-5939 (2006).

Thakkar, A., Thi, T. B. & Pei, D. Global analysis of peptide cyclization efficiency. ACS Comb. Sci. 15, 120-129 (2013).

Timmerman, P. et al. A combinatorial approach for the design of complementarity determining region-derived peptidomimetics with in vitro anti-tumoral activity. J. Biol. Chem. 284, 34126-34134 (2009).

Virta, P. & Lonnberg, H. J. Solid-supported synthesis of cryptand-like macrobicyclic peptides. J. Org. Chem. 68, 8534 (2003).

Wells, J. & McClendon, C. Reaching for high-hanging fruit in drug discovery at proteinprotein interfaces. Nature 450, 1001-1009 (2007).

Wu, X., Upadhyaya, P., Villalona-Calero, M. A., Briesewitz, R. & Pei, D. Inhibition of Ras-effector interactions by cyclic peptides. Med. Chem. Commun. 4, 378-382 (2013).

Xu, L.H. et al. Directed evolution of high-affinity antibody mimics using mRNA display. Chem. Biol. 9, 933-942 (2002).

Yamagishi, Y. et al. Natural product-like macrocyclic N-methyl-peptide inhibitors against a ubiquitin ligase uncovered from a ribosome-expressed de novo library. Chem. Biol. 18, 1562-1570 (2011).

Yin, J. et al. Genetically encoded short peptide tag for versatile protein labeling by Sfp phosphopantetheinyl transferase. Proc. Natl. Acad. Sci. USA 102, 15815-15820 (2005).

Zhou, H. et al. Structure-based design of high-affinity macrocyclic peptidomimetics to block the menin-mixed lineage leukemia 1 (MLLI) protein-protein interaction. J. Med. Chem. 56, 1113-1123 (2013).

Extended European Search Report received Nov. 17, 2016 in related European Application No. 14800563.

Upadhyaya et al. "Direct Ras inhibitors identified from a structurally ridigified bicyclic peptide library." Tetrahedron, 2014, 70(42), 7714-7720.

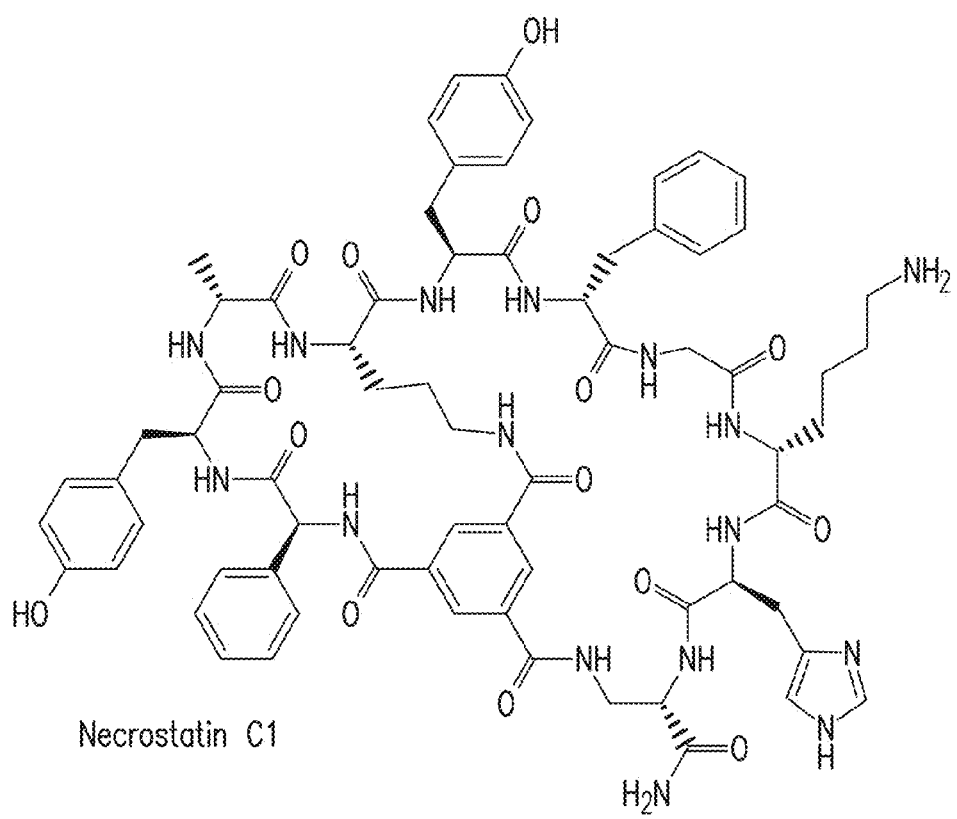
Necrostatin C1
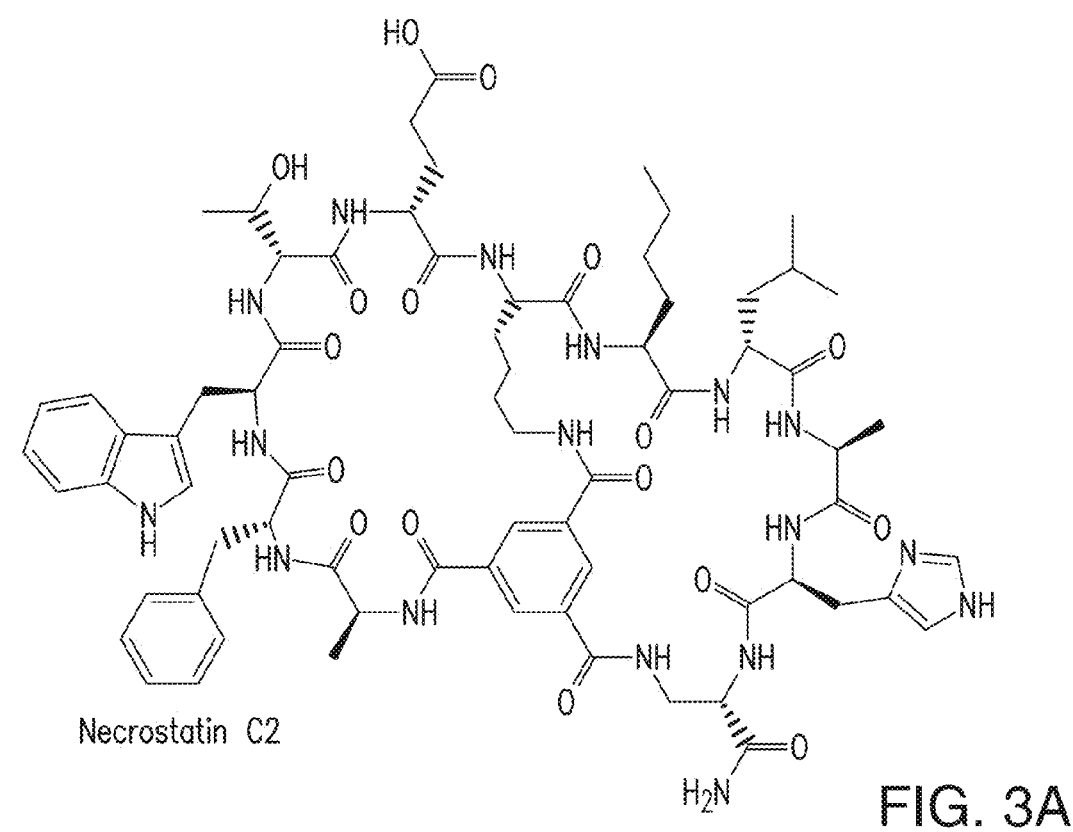
Necrostatin C2
FIG. 3A

FITC-labeled Necrostatin C1

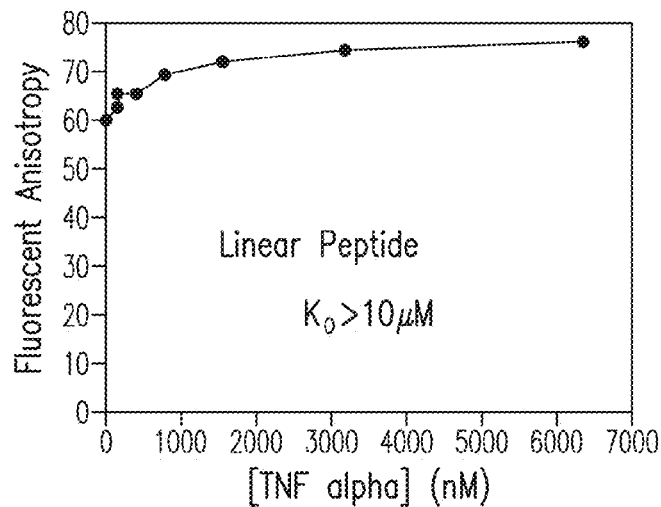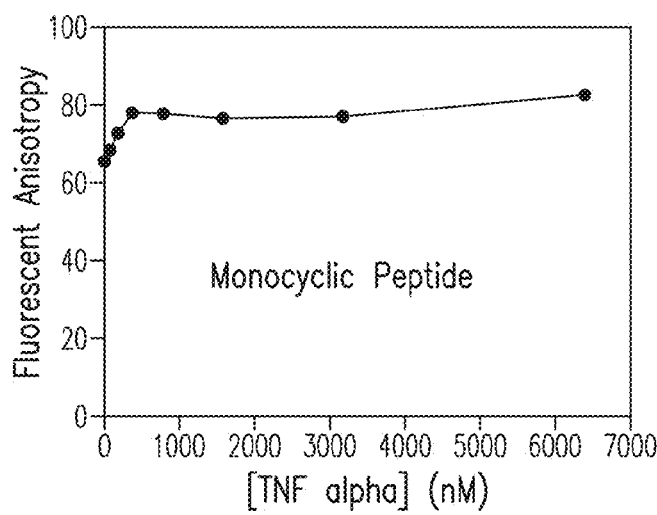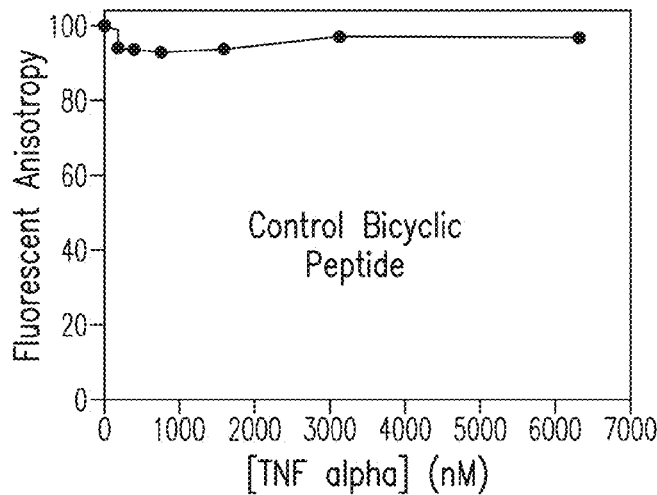
FIG. 9B

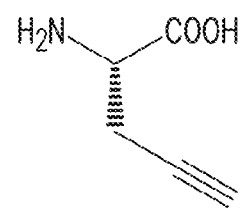 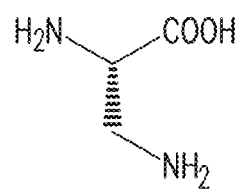 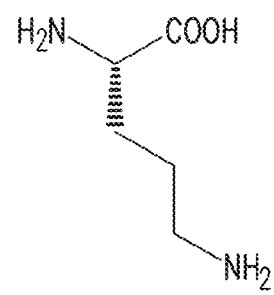
L-Proparygyl glycine (Pra)  L-Diaminopropionic acid (Dap)  L-Ornithine (Orn)
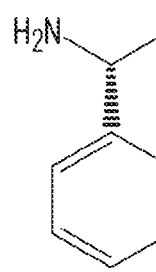 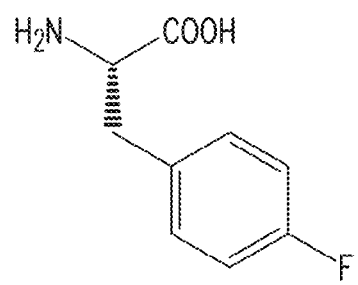 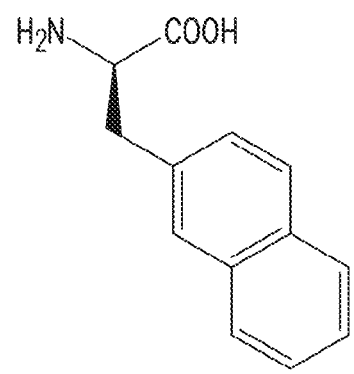
L-Phenylglycine (Phg)  L-4-Fluorophenylalanine (Fpa)  D-2-napthylalanine (Nal)
FIG. 14

|  | X1 | X2 | X3 | X4 | X5 |  |  |  |  |  |  |  |
|---|---|---|---|---|---|---|---|---|---|---|---|---|
| TT042413-A1 | R | dF | Z | Z | dF | K | F | Nal | R | R | R | R |
| TT042413-A2 | R | D | Phg | Z | dN | K | F | Nal | R | R | R | R |
| TT042413-A3 | Z | Z | dP | G | A | K | F | Nal | R | R | R | R |
| TT042413-A4 | Z | Z | A | S | A | K | F | Nal | R | R | R | R |
| TT042413-A5 | Z | Z | dL | dP | dT | K | R | R | R | R | Nal | F |
| TT042413-A8 | Phg | R | dN | Z | I | K | F | Nal | R | R | R | R |
| TT042413-A9 | Z | dT | dE | A | dN | K | F | Nal | R | R | R | R |
| TT042413-A10 | Z | dNal | dV | G | Q | K | F | Nal | R | R | R | R |
| TT042413-A12 | Z | Phg | S | Z | Z | K | F | Nal | R | R | R | R |
| TT042413-B1 | Z | Phg | M | S | Z | K | F | Nal | R | R | R | R |
| TT042413-B3 | Z | S | M | Z | G | K | F | Nal | R | R | R | R |
| TT042413-B5 | Z | S | Phg | Z | Z | K | F | Nal | R | R | R | R |
| TT042413-B8 | Z | R | dV | D | A | K | F | Nal | R | R | R | R |

FIG. 20

|  | X1 | X2 |  |  |  |  | X3 |  |  |
|---|---|---|---|---|---|---|---|---|---|
| TT111113D1 | A | dF | Phg | R | dN | Pra | I | A | K | FNalR4 |
| TT111113D4 | dA | Abu | Phg | R | dN | Pra | I | Abu | K | FNalR4 |
| TT111113E4 | Phg | I | Phg | R | dN | Pra | I | Abu | K | FNalR4 |
| TT111113D11 | none | Phg | Phg | R | dN | Pra | I | Abu | K | FNalR4 |
| TT111113E3 | A | dL | Phg | R | dN | Pra | I | D | K | FNalR4 |
| TT111113E5 | dA | Q | Phg | R | dN | Pra | I | D | K | FNalR4 |
| TT111113E7 | I | dE | Phg | R | dN | Pra | I | D | K | FNalR4 |
| TT111113D5 | dA | S | Phg | R | dN | Pra | I | dE | K | FNalR4 |
| TT111113D8 | none | dL | Phg | R | dN | Pra | I | dE | K | FNalR4 |
| TT111113E1 | dA | Phg | Phg | R | dN | Pra | I | dF | K | FNalR4 |
| TT111113E6 | A | Orn | Phg | R | dN | Pra | I | dF | K | FNalR4 |
| TT111113D12 | A | Abu | Phg | R | dN | Pra | I | dN | K | FNalR4 |
| TT111113E8 | dA | A | Phg | R | dN | Pra | I | dN | K | FNalR4 |
| TT111113D7 | Phg | dN | Phg | R | dN | Pra | I | I | K | FNalR4 |
| TT111113D9 | dA | Abu | Phg | R | dN | Pra | I | Nle | K | FNalR4 |
| TT111113D2 | none | W | Phg | R | dN | Pra | I | Phg | K | FNalR4 |
| TT111113E2 | A | dN | Phg | R | dN | Pra | I | R | K | FNalR4 |
| TT111113D6 | R | Nle | Phg | R | dN | Pra | I | S | K | FNalR4 |
| TT111113D10 | none | H | Phg | R | dN | Pra | I | Y | K | FNalR4 |

FIG. 21

Cyclorasin B2

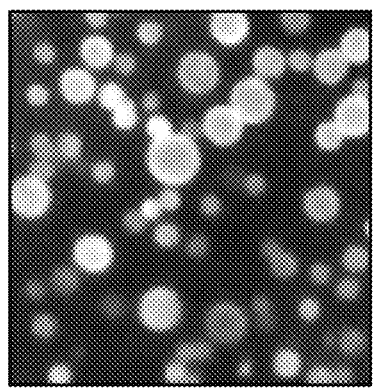
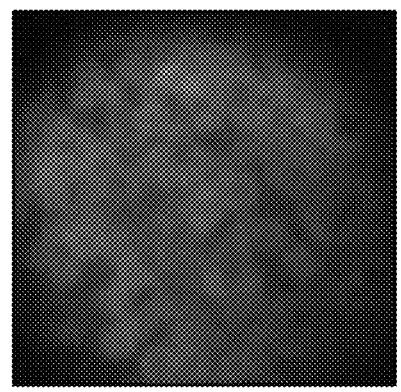
FIG. 23a  FIG. 23b
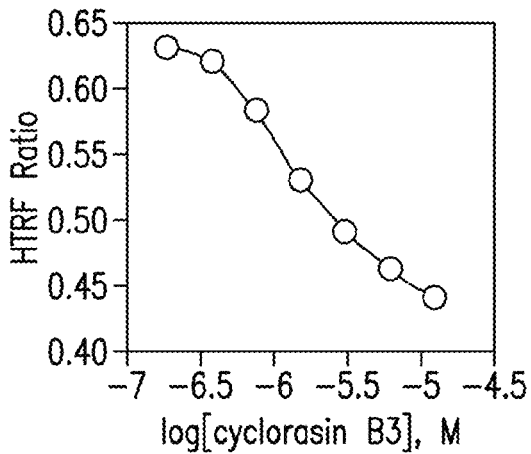
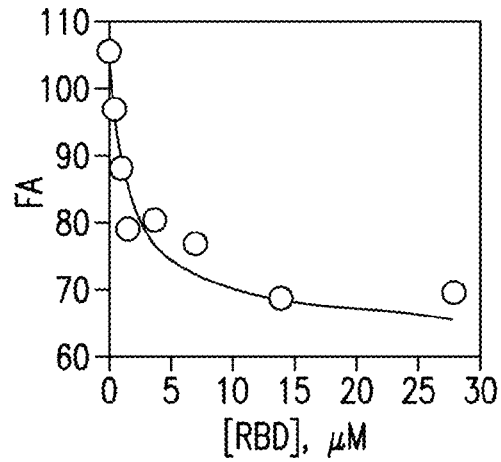
FIG. 23c  FIG. 23d
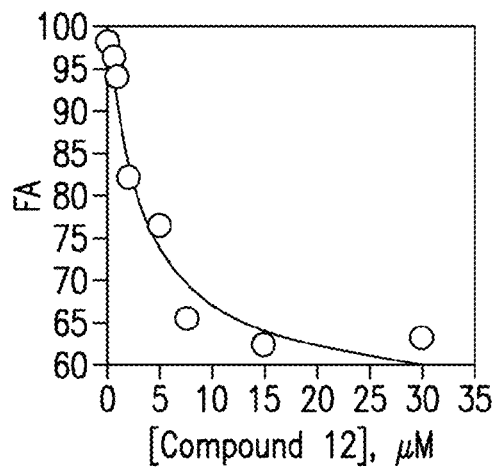
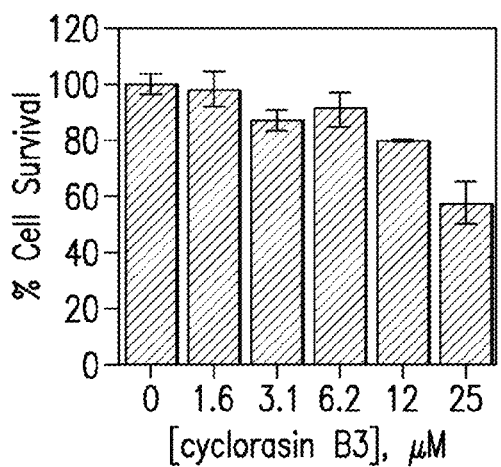
FIG. 23e  FIG. 23f

CHEMICAL SYNTHESIS AND SCREENING OF BICYCLIC PEPTIDE LIBRARIES

CROSS-REFERENCE TO RELATED APPLICATIONS

This application claims the benefit of priority to U.S. Provisional Application No. 61/826,805, filed May 23, 2013, which is hereby incorporated herein by references in its entirety.

STATEMENT REGARDING FEDERALLY FUNDED RESEARCH

This invention was made with government support under grant numbers GM062820 and CA132855 awarded by the National Institutes of Health. The government has certain rights in this invention.

BACKGROUND

Protein-protein interactions represent a new class of exciting drug targets, which are generally considered "undruggable" by conventional small-molecule approaches, because their binding sites are usually large, flat surfaces that lack well defined pockets for small molecules to bind.

Protein-protein interactions (PPIs) are of central importance in essentially all biochemical pathways, including those involved in disease processes. PPIs therefore represent a large class of new, exciting drug targets (Wells, J and McClendon, C. *Nature*, 2007, 450, 1001-1009). However, PPIs are considered the prototypical "undruggable" or "challenging" targets for the conventional small-molecule approach, because PPIs usually involve large, flat interfaces, with which a small molecule generally does not make enough points of contact to impart high affinity or specificity. On the other hand, it has become relatively straightforward to develop specific, high-affinity antibodies against any protein epitopes including flat surfaces. Non-immunoglobulin protein scaffolds have also been engineered into specific binders to target proteins through library screening and/or in vitro evolution (Koide, A et al. *J. Mol. Biol.*, 1998, 284, 1141-1151; Beste, G et al. *Proc. Natl. Acad. Sci. USA*, 1999, 96, 1898-1903; Xu, L. H. et al. *Chem. Biol.*, 2002, 9, 933-942; Rutledge, S E et al. *J. Am. Chem. Soc.*, 2003, 125, 14336¬14347; Steiner, D et al. *J. Mol. Biol.*, 2008, 382, 1211-1227). These antibody and protein binders possess large binding surfaces of their own and are capable of making multiple contacts with a target surface (e.g., those involved in PPIs). Unfortunately, protein-based drugs are impermeable to the mammalian cell membrane; as such they are generally limited to targeting extracellular proteins and are not orally available. Recently, there have been great interests in developing macrocyclic compounds such as cyclic peptides as PPI inhibitors (Koide, A et al. *J. Mol. Biol.*, 1998, 284, 1141-1151; Beste, G et al. *Proc. Natl. Acad. Sci. USA*, 1999, 96, 1898-1903; Xu, L. H. et al. *Chem. Biol.*, 2002, 9, 933-942; Rutledge, S E et al. *J. Am. Chem. Soc.*, 2003, 125, 14336¬14347; Steiner, D et al. *J. Mol. Biol.*, 2008, 382, 1211-1227; Dewan, V et al. *ACS Chem. Biol.*, 2012, 7, 761-769; Wu, X et al. *Med. Chem. Commun.*, 2013, 4, 378-382; Tavassoli, A et al. *ACS Chem. Biol.*, 2008, 3, 757-764; Millward, S W et al. *ACS Chem. Biol.*, 2007, 2, 625-634; Zhou, H et al. *J. Med. Chem.*, 2013, 56, 1113-1123; Yamagishi, Y et al. *Chem. Biol.*, 2011, 18, 1562-1570; Ardi, V C et al. *ACS Chem. Biol.*, 2011, 6, 1357-1366; Leduc, A M et al. *Proc. Natl. Acad. Sci. USA*, 2003, 100, 11273-11278). These macrocycles typically have molecular weights between 500 and 2000 and occupy a largely untapped therapeutic space that is often referred to as the "middle space." Because of their relatively large sizes and therefore ability to make multiple points of contact with a target, they are able to compete with proteins for binding to flat surfaces, and yet retain many of the pharmacokinetic properties of small molecules. Bicyclic peptides have also been generated in order to further contrain their structures and improve their binding affinity/specificity and metabolic stability (Sun, Y et al. *Org. Lett.*, 2001, 3, 1681-1684; Virta, P and Lonnberg, H J. *J. Org. Chem.*, 2003, 68, 8534; Hennis, C et al. *Nat. Chem. Biol.*, 2009, 5, 502-507; Chen, S et al. *ChemBioChem.*, 2012, 13, 1032-1038; Sako, Y et al. *J. Am. Chem. Soc.*, 2008, 130, 7232-7234; Timmerman, P et al. *J. Biol. Chem.*, 2009, 284, 34126-34134).

Described herein are compounds, compositions, and methods useful for such purposes.

SUMMARY

Disclosed herein are compounds, compositions, methods for making and screening large combinatorial libraries of bicyclic peptides displayed on small-molecule scaffolds. In some examples, the overall disk-shaped bicyclic molecules are capable of binding to flat protein surfaces such as the interfaces of protein-protein interactions. Screening of a bicyclic peptide library against tumor necrosis factor-alpha identified potent antagonists that protect cells from tumor necrosis factor-alpha-induced cell death. Potent K-Ras ligands were also identified from bicyclic libraries.

Disclosed herein are bicyclic peptide compounds. In some examples, the compounds disclosed herein are anticancer compounds. In some examples, the compounds have been prepared by solid-phase synthesis. In some examples, the compounds can have a molecular weight of 500 to 5000, such as from 500 to 2000 or 1000 to 2000.

In some examples, the compounds are of Formula I:

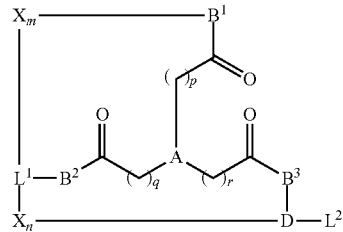

wherein
A is selected from N and benzene;
p, q, and r are independently selected from 0, 1, and 2;
$B_1$, $B_2$, and $B_3$ are independently selected from O and $NR^1$;
wherein $R^1$ comprises H, or substituted or unsubstituted $C_1$-$C_5$ alkyl;
$L_1$ and $L_2$ are independently selected from hydrogen, substituted or unsubstituted $C_1$-$C_6$ alkyl, amino acid, and a linker to a solid phase support;
D is selected from hydrogen, substituted or unsubstituted $C_1$-$C_6$ alkyl, or amino acid residue; and
$X_m$ and $X_n$ independently comprise a sequence of 1-10 amino acids.

In some examples of Formula I, the compounds are of Formula I-A:

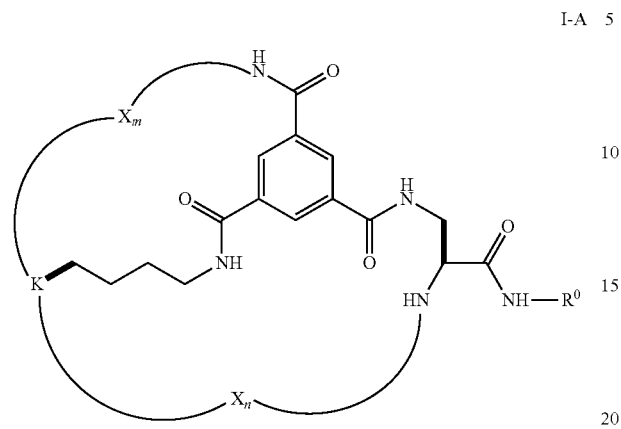

I-A wherein $X_m$ and $X_n$ are as defined in Formula I; $R^0$ is selected from hydrogen, substituted or unsubstituted $C_1$-$C_6$ alkyl, or linker to solid phase support; and K has a structure represented by a formula:

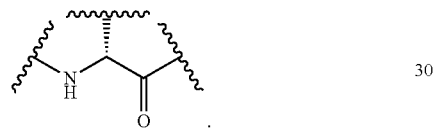

In some examples of Formula I-A, the compound has a structure represented by Formula I-A-1.

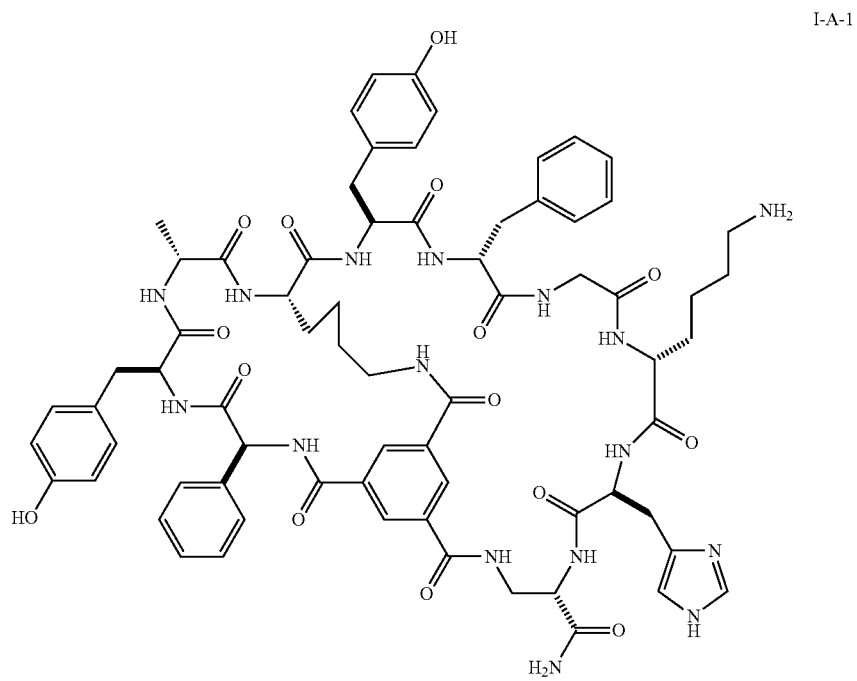

I-A-1

In some examples of Formula I-A, the compound has a structure represented by Formula I-A-2.

I-A-2

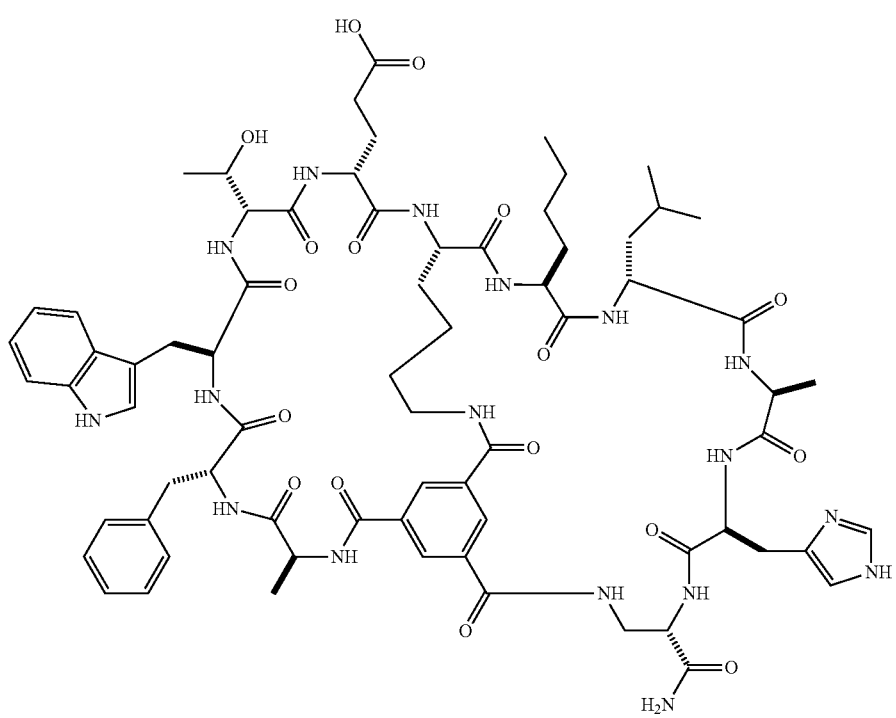

In some examples of Formula I, A comprises N. In some examples of Formula I, p, q, and r are each 1.

In some examples of Formula I, the compounds are of Formula I-B:

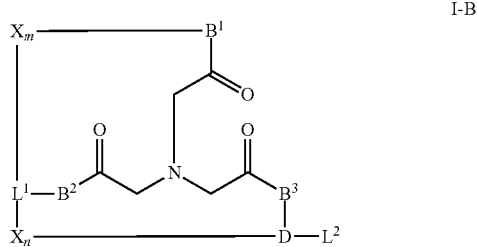

I-B wherein $X_m$, $X_n$, $L^1$, $L^2$, $B^1$, $B^2$, $B^3$ and D are as defined in Formula I.

Also disclosed herein, are compounds comprising a) a residue of trimesic acid, the residue bearing three carboxyl functionalities; b) a lysine residue covalently bonded to the first carboxyl functionality of the trimesic acid residue; c) a first peptide chain of 1-10 amino acid residues, $X_m$, covalently bonded to the second carboxyl functionality of the trimesic acid residue; and d) to the lysine residue; and a second peptide chain of 1-10 amino acid residues, $X_n$, covalently bonded to the third carboxyl functionality of the trimesic acid residue and to the lysine residue.

Also disclosed is a library comprising a plurality of the disclosed compounds.

Also disclosed herein is a method for making a bicyclic peptide compound, the method comprising the steps of: a) linking 2,3-diaminopropanoic acid to a solid phase support via its carboxyl functionality; b) building a first peptide chain of 1-10 amino acid residues from the 2-amino functionality of the 2,3-diaminopropanoic acid residue; c) linking a lysine residue to the distal end of the first peptide chain; d) building a second peptide chain of 1-10 amino acid residues onto the lysine residue; e) linking trimesic acid to the 3-amino functionality of the 2,3-diaminopropanoic acid residue; f) cyclizing the distal amino acid residue of the second peptide chain with a carboxyl functionality of the trimesic acid; and g) cyclizing the amino side chain of the lysine residue with a carboxyl functionality of the trimesic acid.

Also disclosed herein is a method for making a library of bicyclic peptide compounds, the method comprising the steps of: a) linking 2,3-diaminopropanoic acid to a solid phase support via its carboxyl functionality; b) building a first peptide chain of 1-10 amino acid residues from the 2-amino functionality of the 2,3-diaminopropanoic acid residue, using a split-and-pool technique to prepare the chain; c) linking a lysine residue to the distal end of the first peptide chain; d) building a second peptide chain of 1-10 amino acid residues onto the lysine residue, using a split-and-pool technique to prepare the chain; e) linking trimesic acid to the 3-amino functionality of the 2,3-diaminopropanoic acid residue; f) cyclizing the distal amino acid residue of the second peptide chain with a carboxyl functionality of the trimesic acid; and g) cyclizing the amino side chain of the lysine residue with a carboxyl functionality of the trimesic acid.

Also disclosed herein is a method of treating or preventing a disorder in a subject, such as a human, comprising administering to the subject an effective amount of a compound disclosed herein or a pharmaceutically acceptable salt thereof. In some examples, the subject is an animal, such as a human. In some examples, the subject is identified as having a need for treatment of the disorder. In some examples, the method treats a disorder. In some examples, the disorder is associated with TNF-α-induced cell death, such as dysfunctional regulation of TNF-α-induced cell death. In some examples the disorder is associated with uncontrolled cellular proliferation, such as cancer. In some examples, the disorder is cancer. In some examples the disorder is an inflammatory disorder. In some examples, the disorder is an autoimmune disorder, such as a disorder selected from rheumatoid arthritis, ankylosing spondylitis, Crohn's disease, psoriasis, hidradenitis suppurativa, and refractory asthma.

Also disclosed herein is a method for identifying a drug candidate for treatment of a disorder, the method comprising the steps of: exposing a compound disclosed herein, a compound prepared by the methods disclosed herein, a library disclosed herein, or a library prepared by the methods disclosed to a receptor associated with the disorder; b) detecting reaction between the receptor and the compound or the library; and c) determining the identity of compound reacting with the receptor.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DESCRIPTION OF FIGURES

The accompanying figures, which are incorporated in and constitute a part of this specification, illustrate several aspects and together with the description serve to explain the principles of the invention.

FIG. 14 displays the unnatural building blocks used in the library.

FIG. 20 shows sequences of hit peptides derived from screening the bicyclic library against K-Ras.

FIG. 21 shows sequences of hit peptides from screening results of library II against biotinylated K-Ras.

FIG. 23 displays the biological characterization of cyclorasin B3. FIG. 23a, b show on-bead assay of inhibition of Ras-Raf interaction by cyclorasin B3. In the absence of inhibitor (a), binding of Texas red-labeled K-Ras (500 nM) to immobilized GST-Raf RBD rendered the beads red, whereas the addition of 10 μM cyclorasin B3 abolished Ras-Raf interaction (b). FIG. 23c displays the determination of cyclorasin B3 potency by HTRF assay. FIG. 23d displays the effect of GST-Raf RBD on FITC-cyclorasin B3 (100 nM) binding to K-Ras (3 μM). FIG. 23e displays the effect of compound 12 on FITC-cyclorasin B3 (100 nM) binding to K-Ras (3 μM). FIG. 23f shows the effect of oleiylated cyclorasin B3 on the growth rate of H358 lung cancer cells as measured by MTT assay.

Figure 1:
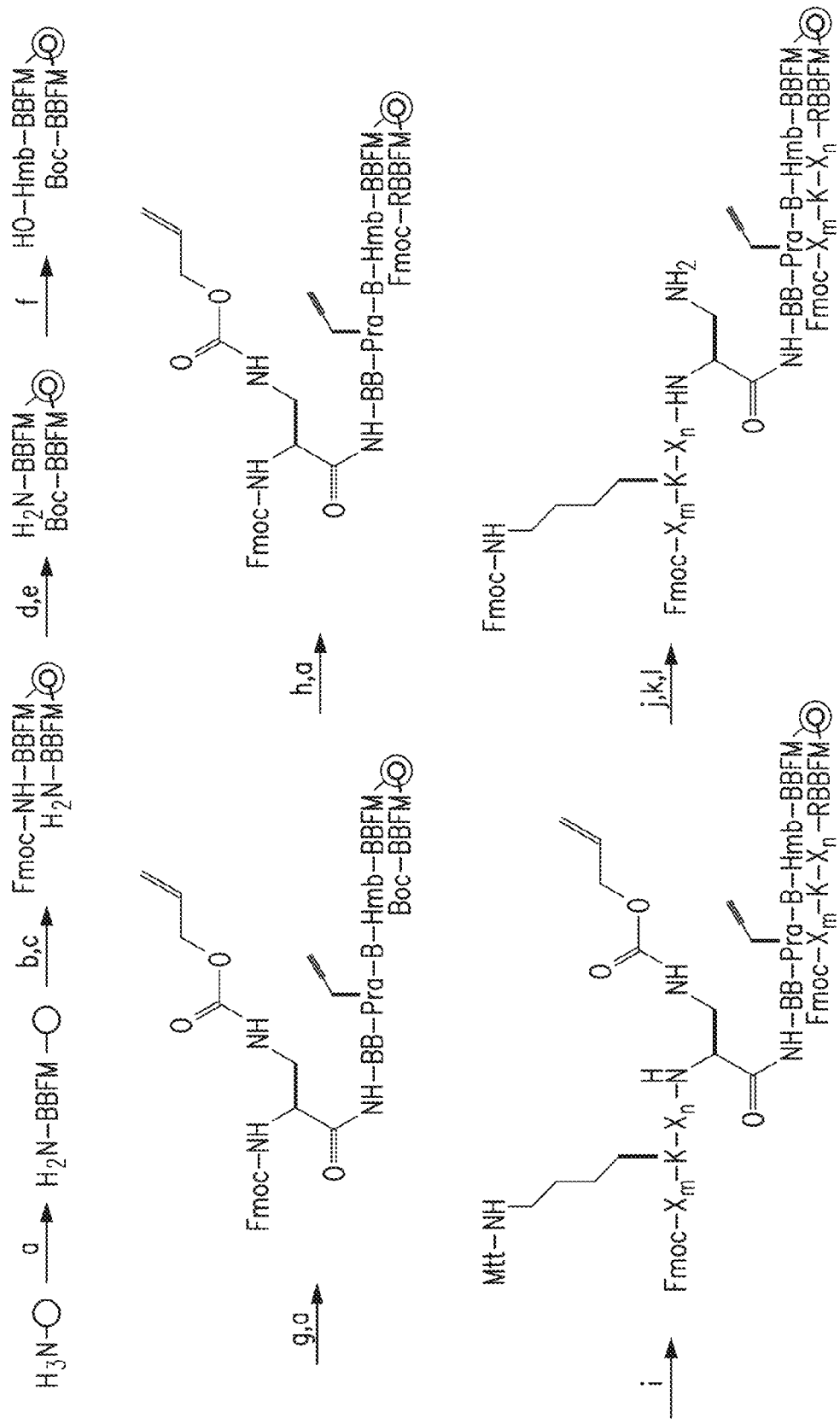
FIG. 1 shows the synthesis of some of the disclosed compounds, such as a bicyclic peptide library. Reagents and Conditions: (a) Standard Fmoc/HATU chemistry; (b) soak in water; (c) 0.4 equiv Fmoc-OSu in $Et_2O/CH_2Cl_2$; (d) di-t-butyl dicarbonate; (e) piperidine; (f) 4-hydroxybenzoic acid/HBTU/HOBT; (g) Fmoc-13-Ala-OH/DIC; (h) 50% TFA in DCM; (i) split-and-pool synthesis by Fmoc/HATU chemistry; (j) 2% TFA in DCM (6x); (k) Fmoc-OSu/DIPEA in DCM; (l) $Pd(PPh_3)_4$; (m) diallyl protected trimesic acid/HATU; (n) PyBOP/HOBT/DIPEA; (o) modified reagent K.
Figure 1:
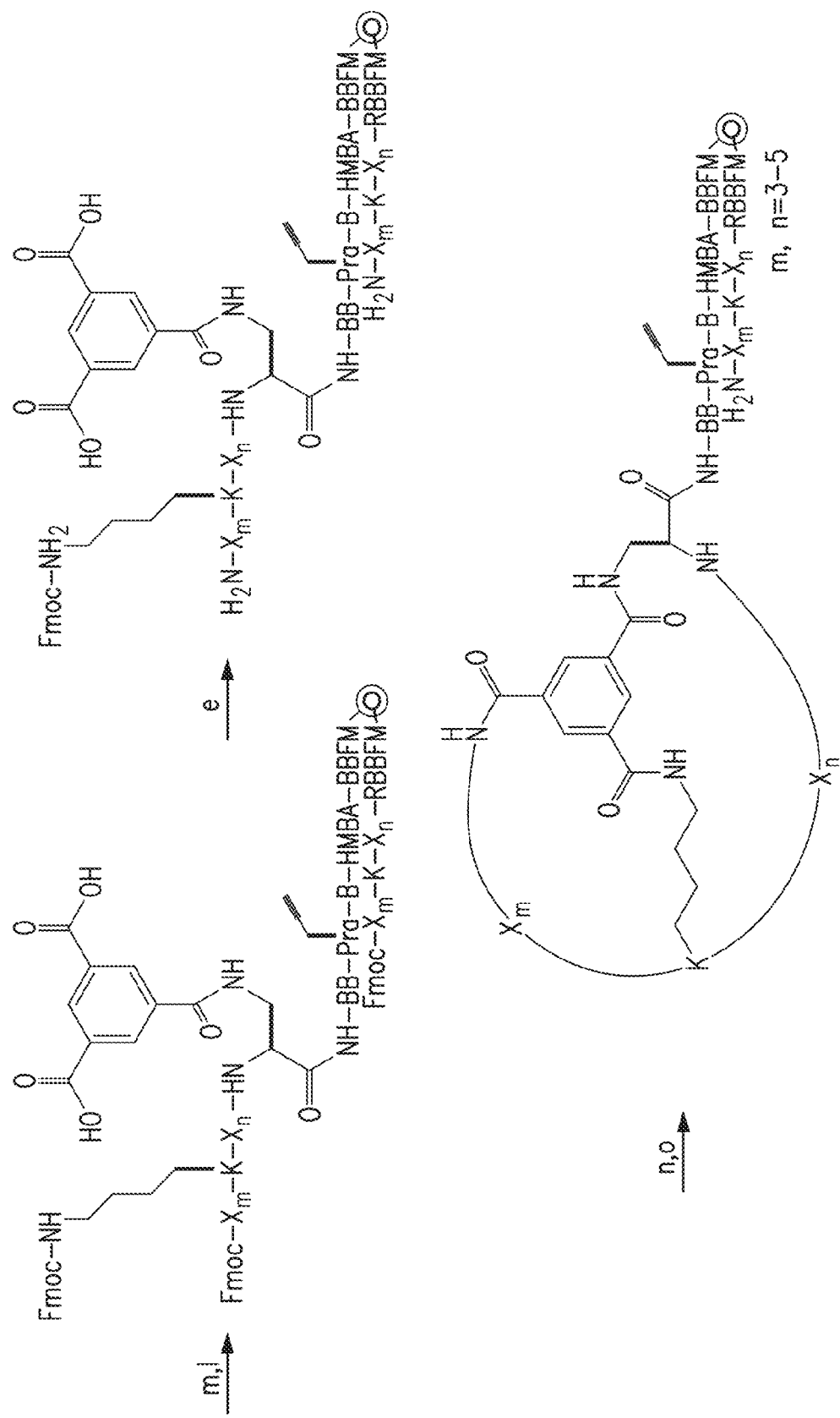

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

General Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" refers to the target of administration, e.g. a subject. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, fish, bird, or rodent. The term does not denote a particular age or sex. Thus, adult and newborn subjects, as well as fetuses, whether male or female, are intended to be covered. In some examples, the subject is a mammal. A patient refers to a subject afflicted with a disease or disorder. The term "patient" includes human and veterinary subjects. In some examples of the disclosed methods, the subject has been diagnosed with a need for treatment of cancer prior to the administering step. In some examples of the disclosed method, the subject has been diagnosed with cancer prior to the administering step. The term subject also includes a cell, such as an animal, for example human, cell.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In some examples, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In some examples, the subject is a mammal such as a primate, and, in some examples, the subject is a human. The term "subject" also includes domesticated animals (e.g., cats, dogs, etc.), livestock (e.g., cattle, horses, pigs, sheep, goats, fish, bird, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or treated by a compound or composition that can treat or prevent cancer. As a further example, "diagnosed with a need for treating or preventing cancer" refers to having been subjected to a physical examination by a person of skill, for example, a physician, and found to have a condition characterized by cancer or other disease wherein treating or preventing cancer would be beneficial to the subject.

As used herein, the phrase "identified to be in need of treatment for a disorder," or the like, refers to selection of a subject based upon need for treatment of the disorder. For example, a subject can be identified as having a need for treatment of a disorder (e.g., a disorder related to cancer) based upon an earlier diagnosis by a person of skill and thereafter subjected to treatment for the disorder. It is contemplated that the identification can, In some examples, be performed by a person different from the person making the diagnosis. It is also contemplated, in some examples, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In some examples, a preparation can be administered therapeutically; that is, administered to treat an existing disease or condition. In some examples, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In some examples, a preparation can be administered in a "prophylactically effective amount"; that is, an amount effective for prevention of a disease or condition.

As used herein, "$EC_{50}$," is intended to refer to the concentration or dose of a substance (e.g., a compound or a drug) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in an in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein the gene or genes has been introduced or knocked-out, as appropriate, to replicate a disease process.

As used herein, "$IC_{50}$," is intended to refer to the concentration or dose of a substance (e.g., a compound or a drug) that is required for 50% inhibition or diminuation of a biological process, or component of a process, including a protein, subunit, organelle, ribonucleoprotein, etc. $IC_{50}$ also refers to the concentration or dose of a substance that is required for 50% inhibition or diminuation in vivo, as further defined elsewhere herein. Alternatively, $IC_{50}$ also refers to the half maximal (50%) inhibitory concentration (IC) or inhibitory dose of a substance. The response can be measured in an in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein a gene or genes has been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

Chemical Definitions

As used herein, the term "substituted" is contemplated to include all permissible substituents of organic compounds. In some examples, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain examples, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_n$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1$C(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1$S(O)$_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1$S(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned herein are preferably those that result in the formation of stable or chemically feasible compounds. In is also contemplated that, in some examples, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in some examples, their recovery, purification, and use for one or more of the purposes disclosed herein.

Suitable monovalent substituents on a substitutable carbon atom of an "optionally substituted" group are independently halogen; —(CH$_2$)$_{0-4}$R°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R●, -(haloR●), —(CH$_2$)$_{0-2}$OH, —(CH$_2$)$_{0-2}$OR●, —(CH$_2$)$_{0-2}$CH(OR●)$_2$; —O(haloR●), —CN, —N$_3$, —(CH$_2$)$_{0-2}$C(O)R●, —(CH$_2$)$_{0-2}$C(O)OH, —(CH$_2$)$_{0-2}$C(O)OR●, —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O)SR·, —(C$_{1-4}$ straight or branched alkylene)C(O)OR, or —SSR● wherein each R● is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In some examples, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

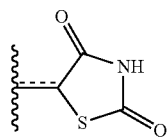

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the compounds and compositions disclosed herein unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In some examples, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the compounds and compositions disclosed herein include all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the compounds and compositions disclosed herein include all such possible diastereomers as well as their racemic mixtures, their substantially pure resolved enantiomers, all possible geometric isomers, and pharmaceutically acceptable salts thereof Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds disclosed herein include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$ respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds and prodrugs thereof can generally be prepared by carrying out the procedures below, by substituting a readily available isotopically labeled reagent for a non-isotopically labeled reagent.

The compounds described herein can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds disclosed herein to form solvates and hydrates. Unless stated to the contrary, all such possible solvates are included in the discussion herein.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an a-hydrogen can exist in an equilibrium of the keto form and the enol form.

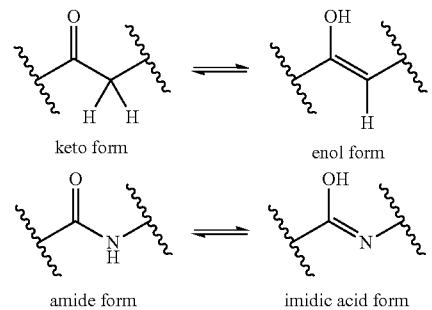

keto form      enol form amide form      imidic acid form

Likewise, amides with an N-hydrogen can exist in an equilibrium of the amide form and the imidic acid form. Unless stated to the contrary, all such possible tautomers are included herein.

It is known that chemical substances form solids which are present in different states of order which are termed polymorphic forms or modifications. The different modifications of a polymorphic substance can differ greatly in their physical properties. The compounds can be present in different polymorphic forms, with it being possible for particular modifications to be metastable. Unless stated to the contrary, all such possible polymorphic forms are included.

In some examples, a structure of a compound can be represented by a formula:

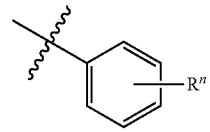

which is understood to be equivalent to a formula:

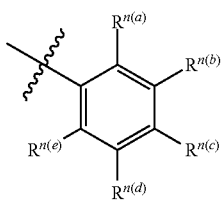

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions disclosed herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C—F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods disclosed herein.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Tumor Necrosis Factor-Alpha

Tumor necrosis factor-alpha (TNFα) is a pleiotropic inflammatory cytokine of a variety of functions, many of which are not yet fully understood (Chen, G and Goeddel, D V. *Science*, 2002, 296, 1634-1635). TNFα is responsible for cachexia, wasting in patients with chronic diseases such as cancer and tuberculosis (Kawakami, M and Cerami, A. *J. Exp. Med.*, 1981, 154, 631-639) and is implicated in the development of septic shock and multi-organ failure in severely infected patients (Beutler, B et al. *J. Exp. Med.*, 1985, 161, 984-995). It is also responsible for numerous chronic inflammatory disorders such as rheumatoid arthritis, ankylosing spondylitis, inflammatory bowel disease, psoriasis, hidradenitis suppurativa, and refractory asthma (Esposito, E and Cuzzocrea, S. *Curr. Med. Chem.*, 2009, 16, 3152-3167). These disorders are currently treated with protein inhibitors, including monoclonal antibodies infliximab (Remicade), adalimumab (Humira) or certolizumab pegol (Cimzia), and a circulating receptor fusion protein etanercept (Enbrel). These proteins bind specifically to TNFα and prevent its interaction with TNFα receptors (TNFRs). These biologic drugs are administered by in-hospital intravenous injections. Considerable efforts have been made over the past two decades to develop small-molecule inhibitors against TNFα, which have the potential to be administered orally. However, these efforts have so far led to only a few weak small-molecule inhibitors that directly bind to TNFα and interfere with TNFα-TNFR interaction (Alzani, R et al. *J. Biol. Chem.*, 1993, 268, 12526-12529; Mancini, F et al. *Biochem. Pharmocol.*, 1999, 58, 851-859; He, M M et al. *Science*, 2005, 310, 1022-1025; Chan, D S et al. *Angew. Chem. Int. Ed. Engi.*, 2010, 49, 2860-2864; Choi, H et al. *Bioorg. Med. Chem. Lett.*, 2010, 20, 6195-6198; Buller, F et al. *Chem. Biol.*, 2009, 16, 1075-1086; Leung, C H et al. *Chem Med Chem*, 2011, 6, 765-768). Disulfide-mediated cyclic peptides corresponding to the TNFα-binding sites in TNFR1 have also shown weak inhibitory activity against TNFα binding to its receptor and TNFα-mediated apoptosis (Takasaki, W et al. *Nat. Biotechnol.*, 1997, 15, 1266-1270; Saito, H et al. *Arthritis Rheum.*, 2007, 56, 1164-1174). The latter observation inspired us to develop macrocyclic compounds as TNFα inhibitors. Disclosed herein is a methodology for high-throughput synthesis and screening of large combinatorial libraries of bicyclic peptides and the discovery of Necrostatin C1 as a potent, bicyclic peptidyl antagonist against TNFα.

Disclosed herein is a methodology for chemical synthesis and screening of large combinatorial libraries of bicyclic peptides displayed on small-molecule scaffolds. By using planar trimesic acid as the scaffold, it is shown that the resulting disk-shaped molecules are privileged for binding to flat protein surfaces such as the interfaces of protein-protein interactions. Screening of a bicyclic peptide library against tumor necrosis factor-alpha (TNFα) identified a potent antagonist that inhibits the TNFα-TNFα receptor interaction and protects cells from TNFα-induced cell death. Bicyclic peptides of this type can provide a general solution for inhibition of protein-protein interactions.

In some examples, disclosed herein is a method for displaying peptidic or peptidomimetic sequences on small-molecule scaffolds to form bicyclic molecules that rival antibodies for binding affinity and specificity. Inhibitors were developed against PPIs, which are a large class of exciting but generally considered "undruggable" targets by conventional small-molecule approaches. A planar scaffold, trimesic acid, was chosen in order to maximize the surface area of the resulting molecules and therefore their ability to interact with flat protein surfaces such as the PPI interfaces. A bicyclic peptide library was generated by "wrapping" a peptide sequence of 6-10 random residues around the trimesoyl group. Peptide cyclization was mediated by the formation three amide bonds between the trimesoyl scaffold and the N-terminal amine, the side chain of a C-terminal L-2, 3-diaminopropionic acid (Dap), and the side chain of a fixed lysine within the random region. The resulting bicyclic peptides contained 3-5 random residues in each ring. The random sequence was constructed with a 25-amino acid set judiciously selected based on their structural diversity, metabolic stability, and commercial availability. It included 10 proteinogenic α-L-amino acids [Ala, Arg, Asp, Gln, Gly, His, Ile, Ser, Trp, and Tyr], 5 nonproteinogenic α-L-amino acids [L-4-fluorophenylalanine (Fpa), L-norleucine (Nle), L-ornithine (Orn), and L-phenylglycine (Phg)], and 10 a-D-amino acids [D-2-naphthylalanine (D-Nal), D-Ala, D-Asn, D-Glu, D-Leu, D-Lys, D-Phe, D-Pro, D-Thr, and D-Val]. This library has a theoretical diversity of 1.0×10e14. Inclusion of unnatural amino acids (and in the future non-peptidic building blocks) greatly increases the structural diversity and proteolytic stability of the compounds but also necessitates the chemical synthesis of the resulting compound libraries.

A challenge associated with screening chemically synthesized bicyclic peptide libraries is structural determination of the hit compounds. To overcome this difficulty, the bicyclic peptide library was synthesized in the one bead-two compound format on TentaGel microbeads (90 µm, 2.86×10e6 beads/g, ~100 pmol peptide/bead), by employing a published bead-segregation technique. Each library bead was topologically segregated into two different layers, with the outer layer displaying a unique bicyclic peptide and the inner layer containing the corresponding linear peptide as an encoding tag. The symmetry of the trimesoyl unit ensured that a single bicyclic product was formed on each bead. The library was designed such that the bicyclic peptide on the bead surface also carried an L-propargylglycine (Pra) residue in its linker region, whereas the linear encoding peptide does not.

Library screening against target proteins can be carried out in four steps. During steps 1 and 2, the library was incubated with the target protein labeled with a biotin and positive beads were isolated by magnetic sorting (step 1) and an on-bead enzyme-linked assay (step 2). At step 3, the positive beads from step 2 were tested again against fluorescently labeled target protein and the fluorescent beads were isolated. Finally, at step 4 the bicyclic peptide was selectively released from each positive bead and tested for binding to the target protein in solution by fluorescence polarization assay. For bicyclic peptides that showed solution-phase binding activity, the encoding peptides on their corresponding beads were individually sequenced by a mass spectrometric method previously developed in this laboratory (PED-MS).

Screening of the bicyclic peptide library against human tumor necrosis factor-alpha (TNF-alpha) resulted in two potent ligands, Necrostatin C1 and C2, with $K_D$ values of 0.45 and 1.9 µM, respectively. Necrostatin C1 was selected for further tests and shown to inhibit TNF-alpha binding to its cognate receptor with an IC50 of 3.1 micromolar. It also protected cells from TNF-alpha induced cell death. The same library was also screened against human K-Ras protein. Several high nanomolar K-Ras ligands were discovered, some of which inhibited the interaction between K-Ras and its effector proteins (e.g., Raf kinase). The TNF-alpha inhibitors are potentially useful for treatment of inflammatory diseases such as rheumatoid arthritis. K-Ras inhibitors will provide a novel class of anticancer drugs.

Compounds

Disclosed herein are bicyclic peptide compounds. In some examples, the compounds disclosed herein are anticancer compounds. In some examples, the compounds have been prepared by solid-phase synthesis. In some examples, the compounds can have a molecular weight of 500 to 5000, such as from 500 to 2000 or 1000 to 2000.

In some examples, the compounds are of Formula I:

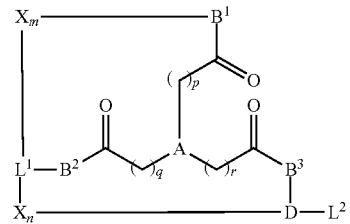

wherein

A is selected from N and benzene;

p, q, and r are independently selected from 0, 1, and 2;

$B_1$, $B_2$, and $B_3$ are independently selected from O and $NR^1$;

wherein $R^1$ comprises H, or substituted or unsubstituted $C_1$-$C_5$ alkyl;

$L_1$ and $L_2$ are independently selected from hydrogen, substituted or unsubstituted $C_1$-$C_6$ alkyl, amino acid, and a linker to a solid phase support;

D is selected from hydrogen, substituted or unsubstituted $C_1$-$C_6$ alkyl, or amino acid residue; and $X_m$ and $X_n$ independently comprise a sequence of 1-10 amino acids.

In some examples, the compounds disclosed herein of Formula I can comprise anticancer compounds. In some examples, the compounds of Formula I can be prepared by solid-phase synthesis.

In some examples, the compounds of Formula I can have a molecular weight of 500 or greater (e.g., 1000 or greater, 1500 or greater, 2000 or greater, 2500 or greater, 3000 or greater, 3500 or greater, 4000 or greater, or 4500 or greater). In some examples, the compounds of Formula I can have a molecular weight of 5000 or less (e.g., 4500 or less, 4000 or less, 3500 or less, 3000 or less, 2500 or less, 2000 or less, 1500 or less, or 1000 or less). In some examples, the compounds of Formula I can have a molecular weight of 500 to 5000 (e.g., 500-2500, 500-1500, 500-1000, 1000-1500, 1500-2500, 1500-2000, 2000-2500, 2500-5000, 2500-3000, 3000-3500, 3500-4000, 4000-4500, 4500-5000, 2500-3500, 3500-4500, 500-2000, or 1000-2000).

$X_m$ and $X_n$ $X_m$ and $X_n$ can independently comprise a sequence of 1-10 amino acids. In some examples, $X_m$ and $X_n$ can independently comprise 1 or more amino acid (e.g., 2 or more, 3 or more, 4 or more, 5 or more, 6 or more, 7 or more, 8 or more, or 9 or more). In some examples, $X_m$ and $X_n$ can independently comprise 10 or less amino acids (e.g., 9 or less, 8 or less, 7 or less, 6 or less, 5 or less, 4 or less, 3 or less, or 2 or less). In some examples, $X_m$ and $X_n$ can independently comprise 1-10 amino acids (e.g., 1-5, 5-10, 1-3, 3-5, 5-8, 8-10, 1-8, 2-6, or 3-7 amino acids). Each amino acid can be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, a derivative, or combinations thereof. These are listed in the Table 1 along with their abbreviations used herein.

TABLE 1

Amino Acid Abbreviations

| Amino Acid | Abbreviations* |
|---|---|
| alanine | Ala (A) |
| allosoleucine | AIle |
| arginine | Arg (R) |
| asparagine | Asn (N) |
| aspartic acid | Asp (D) |
| cysteine | Cys (C) |

TABLE 1-continued

Amino Acid Abbreviations

| Amino Acid | Abbreviations* |
|---|---|
| glutamic acid | Glu (E) |
| glutamine | Gln (Q) |
| glycine | Gly (G) |
| histidine | His (H) |
| isoleucine | Ile (I) |
| leucine | Leu (L) |
| lysine | Lys (K) |
| Methionine | Met (M) |
| napthylalanine | Nal (Φ) |
| Norleucine | Nle (Ω) |
| phenylalanine | Phe (F) |
| proline | Pro (P) |
| selenocysteine | Sec (U) |
| serine | Ser (S) |
| threonine | Thr (T) |
| tyrosine | Tyr (Y) |
| tryptophan | Trp (W) |
| valine | Val (V) |
| Phenylglycine | Phg |
| Propargylglycine | Pra |

Further, non-natural amino acids and D-amino acids can be used herein. The disclosed methods and compositions are particularly well suited for incorporating non-natural and D-amino acids.

The amino acids can be coupled by a peptide bond. The amino acids can be coupled to each other or to $B^1$, $L^1$ or D at the amino group, the carboxylate group, or the side chain.

In some examples of Formula I, $X_m$ and $X_n$ can independently selected from any of the sequences listed in Table 2.

TABLE 2

Example sequences for $X_m$ and $X_n$.

| SEQ ID NO | Sequence | Abbreviation |
|---|---|---|
|  | Phe-Tyr-Ala | FYA |
| 1 | His-Lys-Gly-Phe-Tyr | HKGFY |
| 2 | Ala-Phe-Trp-Thr-Glu | AFWTG |
| 3 | His-Ala-Leu-Nle | HAL-Nle |
| 4 | Phg-Tyr-Ala-Lys-Tyr-Phe-Gly-Lys-His-Dap | Phg-YAKYFGKH-Dap |
| 5 | Ala-Phe-Trp-Thr-Glu-Lys-Nle-Leu-Ala-His-Dap | AFWTEK-Nle-LAH-Dap |
| 6 | Phe-Dap-Ser-Val-Pro-Tyr-His-Dap | F-Dap-SVPYH-Dap |
| 7 | W-F-D-K-F-N-H-Dap | WFDKFNH-Dap |
| 8 | dNal-S-Q-Nal-K-F-R-V-R-Dap | dΦ-SQ-dNal-KFRVR-Dap |
| 9 | R-R-Nal-R-fF-K-F-dQ-G-Dap | RRdΦ-R-fF-KFQG-Dap |
| 10 | O-R-Nal-R-fF-K-F-Q-G-Dap | OR-dΦ-R-fF-KFQG-Dap |
| 11 | R-dF-Z-Z-F-K | RFZZFK |
| 12 | R-D-Phg-Z-N-K | RD-Phg-ZNK |
| 13 | Z-Z-P-G-A-K | ZZPGAK |
| 14 | Z-Z-A-S-A-K | ZZASAK |
| 15 | Z-Z-L-P-dT-K | ZZLPTK |
| 16 | Phg-R-N-Z-I-K | Phg-RNZIK |

TABLE 2-continued

Example sequences for $X_m$ and $X_n$.

| SEQ ID NO | Sequence | Abbreviation |
|---|---|---|
| 17 | Z-T-E-A-N-K | ZTEANK |
| 18 | Z-Nal-V-G-Q-K | Z-dΦ-VGQK |
| 19 | Z-Phg-S-Z-Z-K | Z-Phg-SZZK |
| 20 | Z-Phg-M-S-Z-K | Z-Phg-MSZK |
| 21 | Z-S-M-Z-G-K | ZSMZGK |
| 22 | Z-S-Phg-Z-Z-K | ZS-Phg-ZZK |
| 23 | Z-R-V-D-A-K | ZRVDAK |
| 24 | Arg-Asp-Phg-Pra-Asn | RD-Phg-Pra-N |
| 25 | FNalR$_4$-Dap | ΦRRRR-Dap |
| 26 | Phg-Arg-Asn-Pra-Ile | Phg-RN-Pra-I |
| 27 | Pra-Ser-Phg-Lys-Lys | Pra-S-Phg-KK |
| 28 | Pra-Arg-Val-Asp-Ala | Pra-RVDA |
| 29 | Ala-Phg-Arg-Asn-Pra-Ile | A-Phg-RN-Pra-I |
| 30 | Phg-Arg-Asn-Pra-Ile-Ala | Phg-RN-Pra-IA |
| 31 | Ala-Phg-Arg-Asn-Pra-Ile-Ala | A-Phg-RN-Pra-IA |
| 32 | Ala-Ala-Phg-Arg-Asn-Pra-Ile-Ala | AA-Phg-RN-Pra-IA |
| 33 | A-F-Phg-R-N-Pra-I-A | AF-Phg-RN-Pra-I-A |
| 34 | A-Abu-Phg-R-N-Pra-I-Abu | A-Abu-Phg-RN-Pra-I-Abu |
| 35 | Phg-I-Phg-R-N-Pra-I-Abu-K | Phg-I-Phg-RN-Pra-I-Abu-K |
| 36 | Phg-Phg-R-N-Pra-I-Abu | Phg-Phg-RN-Pra-I-Abu |
| 37 | A-dL-Phg-R-N-Pra-I-D | AL-Phg-RN-Pra-ID |
| 38 | A-Q-Phg-R-N-Pra-I-D | AQ-Phg-RN-Pra-ID |
| 39 | I-E-Phg-R-N-Pra-I-D | IE-Phg-RN-Pra-ID |
| 40 | A-S-Phg-R-N-Pra-I-E | AS-Phg-RN-Pra-IE |
| 41 | L-Phg-R-N-Pra-I-E | L-Phg-RN-Pra-IE |
| 42 | A-Phg-Phg-R-N-Pra-I-F | A-Phg-Phg-RN-Pra-IF |
| 43 | A-Om-Phg-R-N-Pra-I-F | A-Om-Phg-RN-Pra-IF |
| 44 | A-Abu-Phg-R-N-Pra-I-N | A-Abu-Phg-RN-Pra-IN |
| 45 | A-A-Phg-R-N-Pra-I-N | dA-A-Phg-RN-Pra-IN |
| 46 | Phg-N-Phg-R-N-Pra-I-I | Phg-N-Phg-RN-Pra-II |
| 47 | A-Abu-Phg-R-N-Pra-I-Nle | A-Abu-Phg-RN-Pra-I-Nle |
| 48 | W-Phg-R-N-Pra-I-Phg | W-Phg-RN-Pra-I-Phg |
| 49 | A-N-Phg-R-N-Pra-I-R | AN-Phg-RN-Pra-IR |
| 50 | R-Nle-Phg-R-N-Pra-I-S | R-Nle-Phg-RN-Pra-IS |
| 51 | H-Phg-R-N-Pra-I-Y-K-FNal | H-Phg-RN-Pra-IYK-Nal |
| 52 | Ala-Abu-Phg-Arg-Asn-Pra-Ile-Abu | A-Abu-Phg-RN-Pra-I-Abu |
| 53 | Phg-Ile-Phg-Arg-Asn-Pra-Ile-Abu | Phg-I-Phg-RN-Pra-I-Abu |

TABLE 2-continued

Example sequences for $X_m$ and $X_n$.

| SEQ ID NO | Sequence | Abbreviation |
|---|---|---|
| 54 | Ala-Leu-Phg-Arg-Asn-Pra-Ile-Asp | AL-Phg-RN-Pra-ID |
| 55 | Ala-Gln-Phg-Arg-Asn-Pra-Ile-Asp | AQ-Phg-RN -Pra-ID |
| 56 | Ala-Orn-Phg-Arg-Asn-Pra-Ile-Phe | A-Orn-Phg-RN-Pra-IF |
| 57 | Ala-Phg-Phg-Arg-Asn-Pra-Ile-Phe | A-Phg-Phg-RN-Pra-IF |
| 58 | Ala-Abu-Phg-Arg-Asn-Pra-Ile-Abu | A-Abu-Phg-RN-Pra-I-Abu |
| 59 | Ala-Ala-Phg-Arg-Asn-Pra-Ile-Ala | AA-Phg-RN-Pra-IA |
| 60 | Ala-Ala-Phe-Arg-Asn-Pra-Ile-Ala | AAFRN-Pra-IA |
| 61 | Ala-Leu-Phe-Arg-Asn-Pra-Ile-Asp | ALFRN-Pra-ID |
| 62 | Phg-Tyr-Ala-Lys-Tyr-Phe-Gly-Lys-His | Phg-YAKYFGKH |
| 63 | Ala-Phe-Trp-Thr-Glu-Lys-Nle-Leu-Ala-His | AFWTEK-Nle-LAH |

In some examples, $X_m$ can by any of SEQ ID NO:1 to SEQ ID NO:63. In some examples, $X_n$ can by any of SEQ ID NO:1 to SEQ ID NO:63. In some examples, $X_m$ can be a variant of any of SEQ ID NO:1 to SEQ ID NO:25. In some examples, $X_n$ can be a variant of any of SEQ ID NO:1 to SEQ ID NO:25. Peptide variants are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of 1 to 3 residues. Deletions are characterized by the removal of one or more amino acid residues from the peptide sequence. Typically, no more than from 1 to 3 residues are deleted at any one site within the peptide. Amino acid substitutions are typically of single residues, but can occur at a number of different locations at once; insertions usually will be on the order of about from 1 to 3 amino acid residues; and deletions will range about from 1 to 3 residues. Deletions or insertions preferably are made in adjacent pairs, i.e. a deletion of 2 residues or insertion of 2 residues. Substitutions, deletions, insertions or any combination thereof can be combined to arrive at a final construct. Substitutional variants are those in which at least one residue has been removed and a different residue inserted in its place. Such substitutions generally are made in accordance with the following Table 3 and are referred to as conservative substitutions.

TABLE 3

Amino Acid Substitutions
Exemplary Conservative Substitutions

| | |
|---|---|
| Ala replaced by Ser | Leu replaced by Ile or Val |
| Arg replaced by Lys or Gln | Lys replaced by Arg or Gln |
| Asn replaced by Gln or His | Met replaced by Leu or Ile |
| Asp replaced by Glu | Phe replaced by Met, Leu, Nal, Phg, or Tyr |
| Cys replaced by Ser | Ser replaced by Thr |
| Gln replaced by Asn or Lys | Thr replaced by Ser |

TABLE 3-continued

Amino Acid Substitutions
Exemplary Conservative Substitutions

| | |
|---|---|
| Glu replaced by Asp | Trp replaced by Tyr |
| Gly replaced by Pro | Tyr replaced by Trp or Phe |
| His replaced by Asn or Gln | Val replaced by Ile or Leu |
| Ile replaced by Leu or Val | |

Substantial changes in function are made by selecting substitutions that are less conservative than those in Table 3, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the peptides provided herein.

It is understood that one way to define the variants of $X_m$ and $X_n$ is through defining the variants in terms of homology/identity to specific known sequences. For example, SEQ ID NO:1 to SEQ ID NO:63 each sets forth a particular sequence. Specifically disclosed are variants of these peptide that have at least, 85%, 90%, 95%, or 97% homology to SEQ ID NO:1 to SEQ ID NO:63. Those of skill in the art readily understand how to determine the homology of two proteins. For example, the homology can be calculated after aligning the two sequences so that the homology is at its highest level.

In addition to variants of SEQ ID NO:1 to SEQ ID NO:63 are derivatives of these peptides which also function in the disclosed methods and compositions. Derivatives are formed by replacing one or more residues with a modified residue, where the side chain of the residue has been modified.

SPECIFIC EXAMPLES

In some examples of Formula I, A comprises benzene. In some examples of Formula I, $B_1$ comprises NH. In some examples of Formula I, $B_2$ comprises NH. In some examples of Formula I, $B_3$ comprises NH. In some examples of Formula I, $B_1$, $B_2$, and $B_3$ each comprise NH. In some examples of Formula I, p, q, and r are each 0.

In some examples of Formula I, the compounds are of Formula I-A:

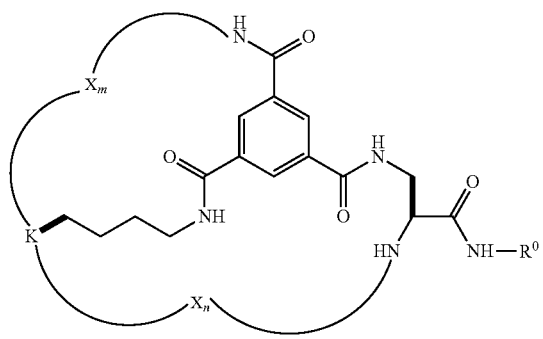

I-A wherein $X_m$ and $X_n$ are as defined in Formula I; $R^0$ is selected from hydrogen, substituted or unsubstituted $C_1$-$C_6$ alkyl, or linker to solid phase support; and K has a structure represented by a formula:

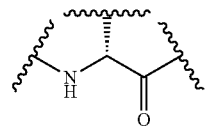

In some examples of Formula I-A, $R^0$ is hydrogen. In some examples of Formula I-A, $R^0$ is a substituted or unsubstituted $C_1$-$C_6$ alkyl. In some examples of Formula I-A, $R^0$ is a linker to a solid phase support.

In some examples of Formula I-A, $X_m$ comprises a peptide chain of 3-7 amino acid residues. In some examples of Formula I-A, $X_m$ comprises a peptide chain of 4-6 amino acid residues. In some examples of Formula I-A, $X_m$ comprises a peptide chain of 3 amino acid residues. In some examples of Formula I-A, $X_m$ comprises a peptide chain of 4 amino acid residues. In some examples of Formula I-A, $X_m$ comprises a peptide chain of 5 amino acid residues. In some examples of Formula I-A, $X_m$ comprises a peptide chain of 6 amino acid residues. In some examples of Formula I-A, $X_m$ comprises a peptide chain of 7 amino acid residues.

In some examples of Formula I-A, $X_m$ comprises all natural amino acids.

In some examples of Formula I-A, $X_n$ comprises a peptide chain of 2-6 amino acid residues. In some examples of Formula I-A, $X_n$ comprises a peptide chain of 3-5 amino acid residues. In some examples of Formula I-A, $X_n$ comprises a peptide chain of 2 amino acid residues. In some examples of Formula I-A, $X_n$ comprises a peptide chain of 3 amino acid residues. In some examples of Formula I-A, $X_n$ comprises a peptide chain of 4 amino acid residues. In some examples of Formula I-A, $X_n$ comprises a peptide chain of 5 amino acid residues. In some examples of Formula I-A, $X_n$ comprises a peptide chain of 6 amino acid residues.

In some examples of Formula I-A, $X_n$ comprises all natural amino acids.

In some examples of Formula I-A, $X_m$ and $X_n$ comprise different amino acid sequences.

In some examples of Formula I-A, the compound has a structure represented by Formula I-A-1.

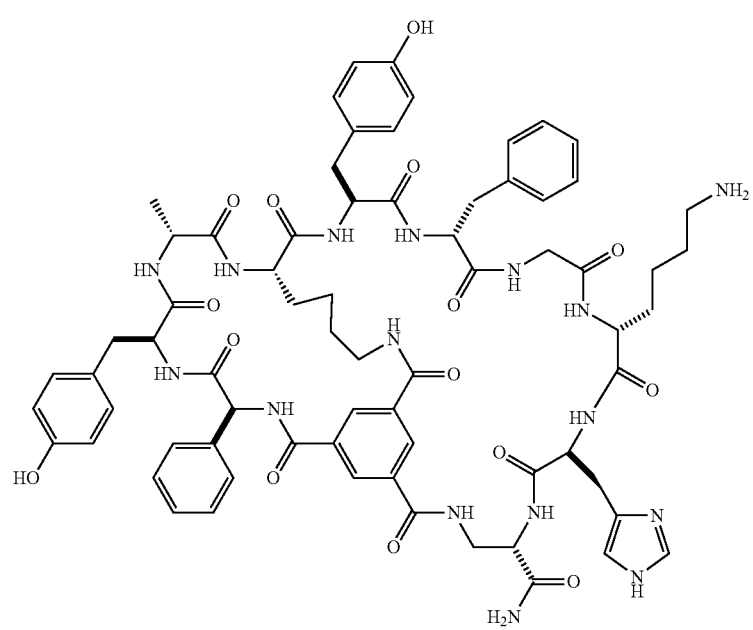

I-A-1

In some examples of Formula I-A, the compound has a structure represented by Formula I-A-2.

I-A-2

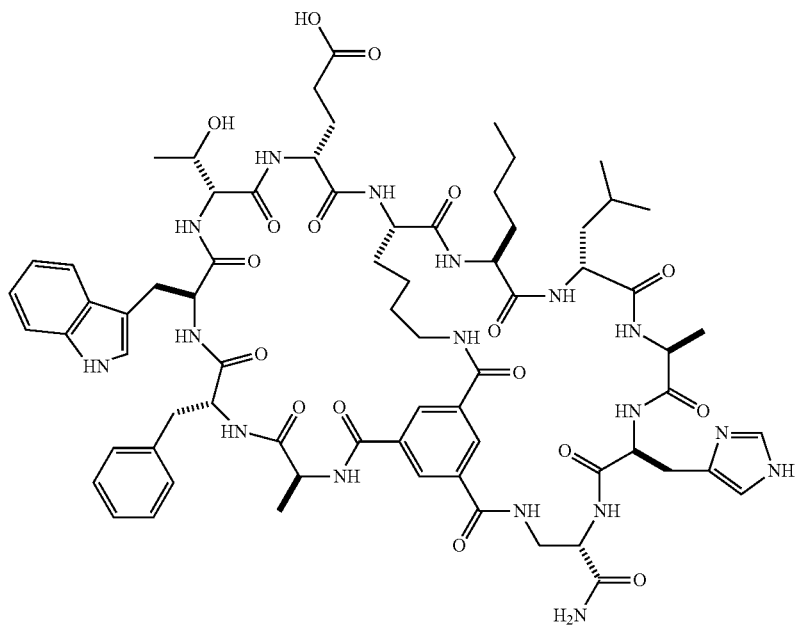

In some examples of Formula I, A comprises N. In some examples of Formula I, p, q, and r are each 1.

In some examples of Formula I, the compounds are of Formula I-B:

I-B

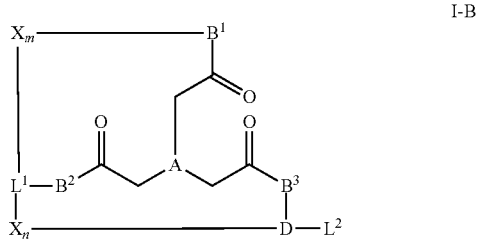

wherein $X_m$, $X_n$, $L^1$, $L^2$, $B^1$, $B^2$, $B^3$ and D are as defined in Formula I.

In some examples of Formula I-B, $X_m$ comprises a peptide chain of 3-7 amino acid residues. In some examples of Formula I-B, $X_m$ comprises a peptide chain of 4-6 amino acid residues. In some examples of Formula I-B, $X_m$ comprises a peptide chain of 3 amino acid residues. In some examples of Formula I-B, $X_m$ comprises a peptide chain of 4 amino acid residues. In some examples of Formula I-B, $X_m$ comprises a peptide chain of 5 amino acid residues. In some examples of Formula I-B, $X_m$ comprises a peptide chain of 6 amino acid residues. In some examples of Formula I-B, $X_m$ comprises a peptide chain of 7 amino acid residues.

In some examples of Formula I-B, $X_m$ comprises all natural amino acids.

In some examples of Formula I-B, $X_n$ comprises a peptide chain of 2-6 amino acid residues. In some examples of Formula I-B, $X_n$ comprises a peptide chain of 3-5 amino acid residues. In some examples of Formula I-B, $X_n$ comprises a peptide chain of 2 amino acid residues. In some examples of Formula I-B, $X_n$ comprises a peptide chain of 3 amino acid residues. In some examples of Formula I-B, $X_n$ comprises a peptide chain of 4 amino acid residues. In some examples of Formula I-B, $X_n$ comprises a peptide chain of 5 amino acid residues. In some examples of Formula I-B, $X_n$ comprises a peptide chain of 6 amino acid residues.

In some examples of Formula I-B, $X_n$ comprises all natural amino acids.

In some examples of Formula I-B, $X_m$ and $X_n$ comprise different amino acid sequences.

Also disclosed herein are compounds comprising a residue of trimesic acid, the residue bearing three carboxyl functionalities; a lysine residue covalently bonded to the first carboxyl functionality of the trimesic acid residue; a first peptide chain of 1-10 amino acid residues, $X_m$, covalently bonded to the second carboxyl functionality of the trimesic acid residue and to the lysine residue; and a second peptide chain of 1-10 amino acid residues, $X_n$, covalently bonded to the third carboxyl functionality of the trimesic acid residue and to the lysine residue.

In some examples, the trimesic acid based compound is covalently linked to a solid phase support.

In some examples of the trimesic acid based compounds, the first peptide chain comprises a peptide chain of 3-7 amino acid residues. In some examples of the trimesic acid based compounds, the first peptide chain comprises a peptide chain of 4-6 amino acid residues. In some examples of the trimesic acid based compounds, the first peptide chain comprises a peptide chain of 3 amino acid residues. In some examples of the trimesic acid based compounds, the first peptide chain comprises a peptide chain of 4 amino acid residues. In some examples of the trimesic acid based compounds, the first peptide chain comprises a peptide chain of 5 amino acid residues. In some examples of the trimesic acid based compounds, the first peptide chain comprises a peptide chain of 6 amino acid residues. In some examples of the trimesic acid based compounds, the first peptide chain comprises a peptide chain of 7 amino acid residues.

In some examples of the trimesic acid based compounds, the first peptide chain comprises all natural amino acids.

In some examples of the trimesic acid based compounds, the second peptide chain comprises a peptide chain of 2-6 amino acid residues. In some examples of the trimesic acid based compounds, the second peptide chain comprises a peptide chain of 3-5 amino acid residues. In some examples of the trimesic acid based compounds, the second peptide chain comprises a peptide chain of 2 amino acid residues. In some examples of the trimesic acid based compounds, the second peptide chain comprises a peptide chain of 3 amino acid residues. In some examples of the trimesic acid based compounds, the second peptide chain comprises a peptide chain of 4 amino acid residues. In some examples of the trimesic acid based compounds, the second peptide chain comprises a peptide chain of 5 amino acid residues. In some examples of the trimesic acid based compounds, the second peptide chain comprises a peptide chain of 6 amino acid residues.

In some examples of the trimesic acid based compounds, the first peptide chain and the second peptide chain comprise different amino acid sequences.

In some examples of the trimesic acid based compounds, the second peptide chain comprises all natural amino acids.

Also disclosed herein is a library comprising a plurality of the disclosed compounds. In some examples, the compounds in the library are covalently linked to a solid phase support.

In some examples, the compounds in the library and/or the solid phase support bear a label moiety. The label moiety can comprise any detectable label. Examples of suitable detectable labels include, but are not limited to, a UV-Vis label, a near-infrared label, a luminescent group, a phosphorescent group, a magnetic spin resonance label, a photosensitizer, a photocleavable moiety, a chelating center, a heavy atom, a radioactive isotope, a isotope detectable spin resonance label, a paramagnetic moiety, a chromophore, or any combination thereof. In some embodiments, the label is detectable without the addition of further reagents.

In some embodiments, the label moiety is a biocompatible label moiety, such that the compounds can be suitable for use in a variety of biological applications. "Biocompatible" and "biologically compatible", as used herein, generally refer to compounds that are, along with any metabolites or degradation products thereof, generally non-toxic to cells and tissues, and which do not cause any significant adverse effects to cells and tissues when cells and tissues are incubated (e.g., cultured) in their presence.

The label moiety can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyromethene, aza-boron dipyromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris(4,7-diphenyl-1,10-phenanthroline) (Ru (dpp)$_3$); Ru (II) tris(1,10-phenanthroline) (Ru(phen)$_3$), tris(2,2'-bipyridine)rutheniurn (II) chloride hexahydrate (Ru (bpy)$_3$); erythrosine B; fluorescein; fluorescein isothiocyanate (FITC); eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitirophenol; alizarin; phenolphthalein; o-cresolphthalein; chlorophenol red; calmagite; bromoxylenol; phenol red; neutral red; nitrazine; 3,4,5,6-tetrabromphenolphtalein; congo red; fluorescein; eosin; 2',7'-dichlorofluorescein; 5(6)-carboxy-fluorecsein; carboxynaphtofluorescein; 8-hydroxypyrene-1,3,6-trisulfonic acid; semi-naphthorhodafluor; semi-naphthofluorescein; tris(4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; dioctadecylcycloxacarbocyanine; fluorenylmethyloxycarbonyl chloride; 7-amino-4-methylcourmarin (Amc); green fluorescent protein (GFP); and derivatives or combinations thereof.

In some examples, the label moiety is a fluorescence label. In some examples, the fluorescence label is a small molecule. Such small molecules are known in the art.

In some examples, the label moiety has a structure represented by a formula:

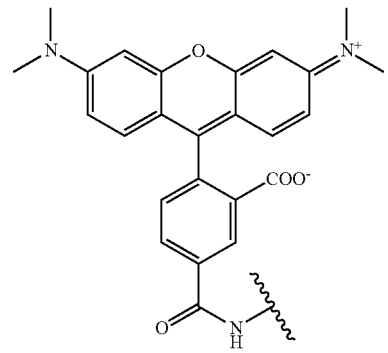

Use of Compounds

In some examples, the disclosed compounds can be administered to a subject. In some examples, the animal is a mammal. In some examples, the mammal is a human. In some examples, the mammal is a mouse. In some examples, the mammal is a rodent. In some examples, the animal is a fish or a bird.

In some examples, the disclosed compounds treat or prevent cancer when administered at a dose of greater than about 1 mg per day in a human. In some examples, the disclosed compounds treat or prevent cancer when administered at a dose of greater than about 5 mg per day in a human. In some examples, the disclosed compounds treat or prevent cancer when administered at a dose of greater than about 10 mg per day in a human. In some examples In some examples, the disclosed compounds treat or prevent a cancer when administered at a dose of greater than about 50 mg per day in a human. In some examples, the disclosed compounds treat or prevent cancer when administered at a dose of greater than about 75 mg per day in a human. In some examples, the disclosed compounds treat or prevent cancer when administered at a dose of greater than about 100 mg per day in a human. In some examples, the disclosed compounds treat or prevent cancer when administered at a dose of greater than about 150 mg per day in a human. In some examples, the disclosed treat or prevent cancer when administered at a dose of greater than about 200 mg per day in a human. In some examples, the disclosed compounds treat or prevent cancer when administered at a dose of greater than about 250 mg per day in a human. In some examples, the disclosed compounds treat or prevent cancer when administered at a dose of greater than about 300 mg per day in a human. In some examples, the disclosed compounds treat or prevent cancer when administered at a dose of greater than about 400 mg per day in a human. In some examples, the disclosed compounds treat or prevent cancer when administered at a dose of greater than about 500 mg per day in a human In some examples, the disclosed compounds treat or prevent cancer when administered at a dose of greater than about 750 mg per day in a human. In some examples, the disclosed compounds treat or prevent cancer when administered at a dose of greater than about 1000 mg per day in a human. In some examples, the disclosed compounds treat or prevent cancer when administered at an amount of greater than about 1500 mg per day in a human. In some examples, the disclosed compounds treat or prevent cancer when administered at a dose of greater than about 2000 mg per day in a human.

In some examples, the disclosed compounds treat or prevent cancer when administered at an oral dose of greater than about 5 mg per day in a human. In some examples, the disclosed compounds treat or prevent cancer when administered at an oral dose of greater than about 10 mg per day in a human. In some examples, the disclosed compounds treat or prevent cancer when administered at an oral dose of greater than about 25 mg per day in a human. In some examples, the disclosed compounds treat or prevent cancer when administered at an oral dose of greater than about 50 mg per day in a human. In some examples, the disclosed compounds treat or prevent cancer when administered at an oral dose of greater than about 75 mg per day in a human. In some examples, the disclosed compounds treat or prevent cancer when administered at an oral dose of greater than about 100 mg per day in a human. In some examples, the disclosed compounds treat or prevent cancer when administered at an oral dose of greater than about 150 mg per day in a human. In some examples, the disclosed treat or prevent cancer when administered at an oral dose of greater than about 200 mg per day in a human. In some examples, the disclosed compounds treat or prevent cancer when administered at an oral dose of greater than about 250 mg per day in a human. In some examples, the disclosed compounds treat or prevent cancer when administered at an oral dose of greater than about 300 mg per day in a human. In some examples, the disclosed compounds treat or prevent cancer when administered at an oral dose of greater than about 400 mg per day in a human. In some examples, the disclosed compounds treat or prevent cancer when administered at an oral dose of greater than about 500 mg per day in a human. In some examples, the disclosed compounds treat or prevent cancer when administered at an oral dose of greater than about 750 mg per day in a human. In some examples, the disclosed compounds treat or prevent cancer when administered at an oral dose of greater than about 1000 mg per day in a human. In some examples, the disclosed compounds treat or prevent cancer when administered at an oral dose of greater than about 1500 mg per day in a human. In some examples, the disclosed compounds treat or prevent cancer when administered at an oral dose of greater than about 2000 mg per day in a human.

Pharmaceutical Compositions

Also disclosed herein are pharmaceutical compositions comprising the disclosed compounds. That is, a pharmaceutical composition can be provided comprising a therapeutically effective amount of at least one disclosed compound. In some examples, a pharmaceutical composition can be provided comprising a prophylactically effective amount of at least one disclosed compound.

Also disclosed herein are pharmaceutical compositions comprising a pharmaceutically acceptable carrier and any of the compounds disclosed herein, wherein the compound is present in an effective amount. Also disclosed herein are neutraceutical compositions comprising a neutraceutically acceptable carrier and any of the compounds disclosed herein, wherein the compound is present in an effective amount.

In some examples of the compositions, the compound is present in an amount greater than about an amount selected from 5 mg, 10 mg, 25 mg, 50 mg, 100 mg, 150 mg, 200 mg, 250 mg, 300 mg, 400, mg, 500 mg, 750 mg, 1000 mg, 1,500 mg, or 2,000 mg.

The disclosed pharmaceutical compositions can further comprise one or more anticancer drugs.

Example anticancer drugs include 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR.

In some examples, the pharmaceutical composition is administered to a subject. In some examples, the subject is a mammal, fish or bird. In some examples, the mammal is a primate. In some examples, the mammal is a human. In some examples, the human is a patient.

In some examples, the pharmaceutical composition is administered following identification of the mammal in need of treatment of cancer. In some examples, the pharmaceutical composition is administered following identification of the mammal in need of prevention of cancer. In some examples, the mammal has been diagnosed with a need for treatment of cancer to the administering step.

In some examples, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically or neutraceutically acceptable non-toxic bases or acids. When the compound is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically or neutraceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared thereof, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds disclosed herein, or pharmaceutically acceptable salts thereof, or neutraceutically acceptable salts thereof, can be combined as the active ingredient in intimate admixture with a pharmaceutical carrier or neutraceutical carrier according to conventional pharmaceutical compounding techniques or conventional neutraceutical compounding techniques. The carrier can take a wide variety of forms depending on the form of preparation desired for administration, e.g., oral or parenteral (including intravenous). Thus, the pharmaceutical compositions or neutraceutical compositions disclosed herein can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds disclosed herein, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions disclosed herein can include a pharmaceutically acceptable carrier and a compound or a pharmaceutically acceptable salt of the compounds disclosed herein. The compounds disclosed herein, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules can be used for oral dosage units whereby solid pharmaceutical carriers are employed. Optionally, tablets can be coated by standard aqueous or nonaqueous techniques A tablet containing any of the compositions disclosed herein can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions disclosed herein can comprise any of the compounds disclosed herein (or pharmaceutically or neutraceutically acceptable salts thereof) as an active ingredient, a pharmaceutically acceptable carrier or neutraceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. In some examples, a preservative can be included to prevent the detrimental growth of microorganisms.

Pharmaceutical compositions disclosed herein suitable for injectable use include sterile aqueous solutions or dispersions. Furthermore, the compositions can be in the form of sterile powders for the extemporaneous preparation of such sterile injectable solutions or dispersions. In some examples, the final injectable form can be sterile and can be effectively fluid for easy syringability. In some examples, the pharmaceutical compositions can be stable under the conditions of manufacture and storage; thus, they can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof Pharmaceutical compositions disclosed herein can be in a form suitable for topical use such as, for example, an aerosol, cream, ointment, lotion, dusting powder, mouth washes, gargles, and the like. In some examples, the compositions can be in a form suitable for use in transdermal devices. These formulations can be prepared, utilizing any of the compounds disclosed herein or pharmaceutically acceptable salts thereof, via conventional processing methods. As an example, a cream or ointment can be prepared by mixing hydrophilic material and water, together with about 5 wt % to about 10 wt % of the compound, to produce a cream or ointment having a desired consistency.

Pharmaceutical compositions disclosed herein can be in a form suitable for rectal administration wherein the carrier is a solid. In some examples, the mixture forms unit dose suppositories. Suitable carriers include cocoa butter and other materials commonly used in the art. The suppositories can be conveniently formed by first admixing the composition with the softened or melted carriers) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing any of the compounds disclosed herein, and/or pharmaceutically acceptable salts thereof, can also be prepared in powder or liquid concentrate form.

In the treatment of cancer, the dosage level of the active ingredient comprising the compound or compositions disclosed herein can be about 0.01 to 500 mg per kg patient body weight per day and can be administered in single or multiple doses. In some examples, he dosage level will be about 0.1 to about 250 mg/kg per day; such as 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0, or 5.0 to 50 mg/kg per day. For oral administration, the compositions can be, for example, in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage of the patient to be treated. The compound can be administered on a regimen of 1 to 4 times per day, such as, for example, once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease or infection undergoing therapy.

Also disclosed herein are methods for the manufacture of a medicament for treating cancer in mammals (e.g., humans) comprising combining one or more disclosed compounds, products, or compositions with a pharmaceutically acceptable carrier or diluent. In some examples, the method for manufacturing a medicament comprises combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days.

Also disclosed are pharmaceutical compositions that comprise a compound disclosed herein in combination with a pharmaceutically acceptable carrier. In some examples, the pharmaceutical compositions are adapted for oral, topical or parenteral administration. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Methods of Using the Compounds and Compositions

Also provided herein are methods of use of the compounds or compositions described herein. Also provided herein are methods for treating a disease or pathology in a subject in need thereof comprising administering to the subject an effective amount of any of the compounds or compositions described herein.

A very important application is for specific delivery of drugs such as anticancer drugs. The bicyclic peptides disclosed herein can be directed to a cancer-specific or over-expressed surface protein. Then an anticancer drug can be covalently or noncovaelently attached to the bicyclic peptide.

Also provided herein are methods of treating, preventing, or ameliorating cancer in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Further examples of cancers treatable by the compounds and compositions described herein include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

In some examples, the cancer can be associated with TNF-α induced cell death.

The methods of treatment or prevention of cancer described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts thereof as described herein can be combined into a pharmaceutical composition with an additional anti-cancer agent, such as 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The additional anti-cancer agent can also include biopharmaceuticals such as, for example, antibodies.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

Also disclosed herein are methods of treating or preventing a disorder in a subject, such as a human, comprising administering to the subject an effective amount of a compound disclosed herein or a pharmaceutically acceptable salt thereof. In some examples, the subject is an animal, such as a human. In some examples, the subject is identified as having a need for treatment of the disorder. In some examples, the method treats a disorder. In some examples, the disorder is associated with TNF-α-induced cell death, such as dysfunctional regulation of TNF-α-induced cell death. In some examples, the disorder is associated with uncontrolled cellular proliferation, such as cancer. In some examples, the disorder is cancer. In some examples, the disorder is an inflammatory disorder. In some examples, the disorder is an autoimmune disorder, such as a disorder selected from rheumatoid arthritis, ankylosing spondylitis, Crohn's disease, psoriasis, hidradenitis suppurativa, and refractory asthma.

In some examples, the subject has been diagnosed with the disorder prior to the administration step.

In some examples, the compound is administered in an amount between about 0.01 to 500 mg per kg patient body weight per day and can be administered in single or multiple doses. In some examples, the dosage level can be about 0.1 to about 250 mg/kg per day, such as about 0.05 to 100 mg/kg per day, or about 0.1 to 50 mg/kg per day. In some examples, the dosage can be 0.05 to 0.5, 0.5 to 5.0 or 5.0 to 50 mg/kg per day. In some examples, the dosage level can be 0.5 to 100 mg/kg per day. For oral administration, the compositions are can be provided in the form of tablets containing 1.0 to 1000 milligrams of the active ingredient, such as 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, such as once or twice per day. This dosing regimen can be adjusted to provide the optimal therapeutic response.

In some examples, the subject is a domesticated animal. In some examples, the domesticated animal is a domesticated fish, domesticated crustacean, or domesticated mollusk. In some examples, the domesticated animal is poultry. In some examples, the poultry is selected from chicken, turkey, duck, and goose. In some examples, the domesticated animal is livestock. In some examples, the livestock animal is selected from pig, cow, horse, goat, bison, and sheep.

In some examples, the method further comprises the step of identifying the animal in need of treatment or prevention of cancer. In some examples, the mammal has been diagnosed with a need for treatment and prevention of cancer prior to the administering step.

Protection Against TNF-α Induced Cell Death

Also disclosed herein are methods for protection against TNFα-induced cell death. The method can comprise administering an effective amount of a compound disclosed herein, a compound made by a method disclosed herein, a library disclosed herein, or a compound identified by methods disclosed herein to a subject identified as having a need for protection against TNFα-induced cell death.

In some examples, the amount is therapeutically effective. In some examples, the amount is prophylactically effective.

In some examples, the subject is a cell. In some examples, the subject is an animal. In some examples, the subject is a human.

Manufacture of a Medicament

Also disclosed herein are methods for the manufacture of a medicament for treating or preventing cancer comprising combining a therapeutically effective amount of a disclosed compound or product of a disclosed method with a pharmaceutically acceptable carrier or diluent.

Also disclosed herein are methods for manufacturing a medicament associated with treating or preventing cancer or the need to treat or prevent cancer with a pharmaceutically acceptable carrier or diluent.

In some examples, the medicament comprises a disclosed compound.

Kits

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Also disclosed herein are kits comprising one or more of the disclosed compounds, and one or more of: a) at least one anticancer compound, b) instructions for treating a disorder associated with cancer, or c) instructions for treating cancer.

In some examples, the kit further comprises at least one agent, wherein the compound and the agent are co-formulated.

In some examples, the compound and the agent are co-packaged. The agent can be any agent as disclosed herein, known to have a side effect of cancer, an agent known to increase the risk of cancer, agent known to treat cancer in a subject.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

Method of Making Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxycarbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl). In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl) phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Disclosed herein are methods for making a bicyclic peptide compound, the methods can comprise: a) linking 2,3-diaminopropanoic acid to a solid phase support via its carboxyl functionality; b) building a first peptide chain of 2-6 amino acid residues from the 2-amino functionality of the 2,3-diaminopropanoic acid residue; c) linking a lysine residue to the distal end of the first peptide chain; d) building a second peptide chain of 3-7 amino acid residues onto the lysine residue; e) linking trimesic acid to the 3-amino functionality of the 2,3-diaminopropanoic acid residue; f) cyclizing the distal amino acid residue of the second peptide chain with a carboxyl functionality of the trimesic acid; and g) cyclizing the amino side chain of the lysine residue with a carboxyl functionality of the trimesic acid.

In some examples, the method further comprises the step of linking a label moiety to the compound.

In some examples, the method further comprises the step of cleaving the compound from the solid phase support. Also disclosed is a method for making a library of bicyclic peptide compounds, the method comprising the steps of: a) linking 2,3-diaminopropanoic acid to a solid phase support via its carboxyl functionality; b) building a first peptide chain of 2-6 amino acid residues from the 2-amino functionality of the 2,3-diaminopropanoic acid residue, using a split-and-pool technique to prepare the chain; c) linking a lysine residue to the distal end of the first peptide chain; d) building a second peptide chain of 3-7 amino acid residues onto the lysine residue, using a split-and-pool technique to prepare the chain; e) linking trimesic acid to the 3-amino functionality of the 2,3-diaminopropanoic acid residue; f) cyclizing the distal amino acid residue of the second peptide chain with a carboxyl functionality of the trimesic acid; and g) cyclizing the amino side chain of the lysine residue with a carboxyl functionality of the trimesic acid.

Methods of Identifying

Also disclosed herein are methods of identifying a drug candidate. In some examples, the drug candidate is a compound disclosed herein or a pharmaceutically acceptable salt thereof Disclosed herein is a method for identifying a drug candidate for treatment of a disorder, the method comprising the steps of: exposing a compound disclosed herein, a compound prepared by the methods disclosed herein, a library disclosed herein, or a library prepared by the methods disclosed to a receptor associated with the disorder; b) detecting reaction between the receptor and the compound or the library; and c) determining the identity of compound reacting with the receptor.

Also disclosed herein is a compound identified by the method of for identifying a drug candidate for treatment of a disorder.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Certain materials, reagents and kits were obtained from specific vendors as indicated below, and as appropriate the vendor catalog, part or other number specifying the item are indicated.

Fmoc-protected L-amino acids were purchased from Advanced ChemTech (Louisville, Ky.), Peptides International (Louisville, Ky.), or Aapptec (Louisville, Ky.). O-Benzotriazole-N,N,N',N'-tetramethyluronium hexafluorophosphate (HBTU) and 1-hydroxybenzotriazole hydrate (HOBt) were from Aapptec. Tetramethylrhodamine azide was prepared as previously described (Wells, J and McClendon, C. Nature, 2007, 450, 1001-1009). All solvents and other chemical reagents were obtained from Sigma-Aldrich, Fisher Scientific (Pittsburgh, Pa.), or VWR (West Chester, Pa.) and were used without further purification unless noted otherwise. N-(9-Fluorenylmethoxycarbonyloxy)succinimide (Fmoc-OSu) was from Advanced ChemTech. Phenyl isothiocyanate was purchased in 1-mL sealed ampoules from Sigma-Aldrich, and a freshly opened ampoule was used in each experiment.

Synthesis of Diallyl Trimesic Acid.

Trimesic acid (2 g, 9.52 mmol) was dissolved in 20 ml of allyl alcohol and cooled to 0° C. Five equiv. of thionyl chloride and 0.1 equiv of DMF were slowly added to the above solution and the reaction mixture was allowed to warm to room temperature. The reaction was refluxed overnight and stopped by evaporation to dryness under reduced pressure. The residue was dissolved in DCM and washed with saturated $NaHCO_3$ solution and brine. The organic layer was dried over $MgSO_4$ and evaporated. The resulting product was dissolved in 1:1 THF/allyl alcohol and 0.9 equiv. of KOH was added. The solution was stirred for 1 h. The reaction mixture was evaporated and the residue was dissolved in DCM and extracted with 0.1 M NaOH. The organic layer was discarded. Concentrated HCl was added to the aqueous layer until the product completely precipitated out of the solution. The precipitate was collected by vacuum filtration and dried under vacuum to afford the desired product (80% yield). $^1$H-NMR (250 MHz, DMSO-d6): δ 8.67-8.69 (m, 3H), 6.02-6.18 (m, 2H), 5.47 (d, $J_{trans}$=17.5 Hz, 2H), 5.35 (d, Jcis=10 Hz, 2H), and 4.88 (d, 4H).

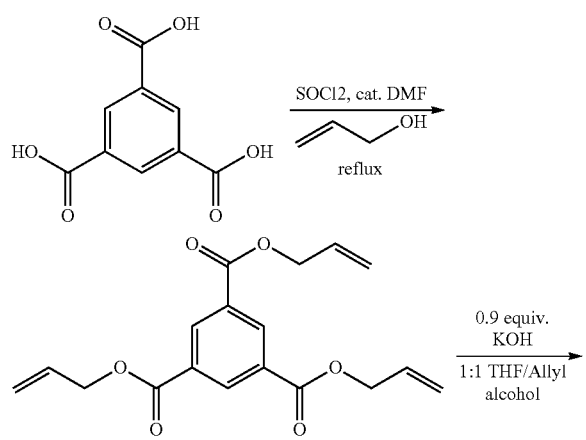

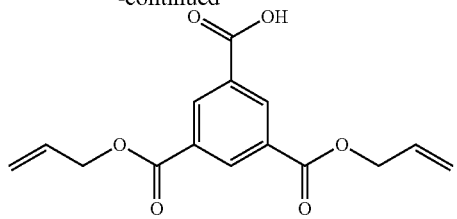

Protein Expression and Purification.

The gene coding for the extracellular domain of human TNFα (aa 77-233) was amplified by the polymerase chain reaction using the full-length TNFα cDNA (Open Biosystem) as template and oligonucleotides 5'-catctcgagtcacagggcaatgatcccaaagt-3' (SEQ ID NO.: 64) and 5'-caccgcaagcttgtcagatcatcttctcgaacc-3' (SEQ ID NO.: 65) as primers. The resulting DNA fragment was digested with endonucleases Hind III and Xho I and inserted into prokaryotic vector pET-22b(+)-ybbR (Yin, J. et al. Proc. Natl. Acad. Sci. U.S.A. 2005, 102, 15815-15820). This cloning procedure resulted in the addition of a ybbR tag (MVLDSLE-FIASKL; SEQ ID NO.: 66) to the N-terminus of TNFα. E. coli BL21(DE3) cells transformed with the pET22b-ybbR-TNFα plasmid were grown at 37° C. in Luria broth (LB) supplemented with 0.05 mg/ml ampicillin to an $OD_{600}$ of 0.50, when protein expression was induced by the addition of isopropyl β-D-1-thiogalactopyranoside (150 μM final concentration). After 5 h at 30° C., the cells (1 L) were harvested by centrifugation. The cell pellet was suspended in 20 mL of lysis buffer (40 mM Tris-HCl, 150 mM NaCl, pH 8.0) plus 0.5% protamine sulfate, 20 mg/mL trypsin inhibitor, 100 mg/ml phenylmethylsulfonyl fluoride and 100 mg/mL lysozyme. The mixture was stirred at 4° C. for 30 min and briefly sonicated (2×10 s pulses). The crude lysate was centrifuged to yield a clear supernatant, which was diluted 10 times in running buffer (20 mM Tris-HCl, 1 mM EDTA, 0.5% triton X100, pH 8.0) and passed through Q-Sepharose column. The column was eluted with 50 mL of running buffer with a gradient of 0-1000 mM NaCl. The ybbR tagged TNFα fractions were pooled and concentrated to ~1 mL using an Amicon Ultra-15 cellulose membrane filter. The resulting solution was passed through a Mono-Q 10/100 GL anion-exchange column equilibrated in the running buffer. The column was eluted with the running buffer plus a linear gradient of 0-1000 mM NaCl. Fractions containing TNFα were pooled and concentrated in an Amicon Ultra-15 cellulose filter. Protein concentration was determined by Bradford assay using bovine serum albumin as the standard.

Protein Labeling.

Biotinylation of TNFα was carried out by treating the ybbR-tagged TNFα protein (80 μM) in 50 mM HEPES, pH 7.4, 10 mM $MgCl_2$ with Sfp phosphopantetheinyl transferase (1 μM) and biotin-CoA (Yin, J. et al. Proc. Natl. Acad. Sci. U.S.A. 2005, 102, 15815-15820) (100 μM) for 30 min at room temperature. Texas-Red labeling of TNFα was similarly carried out except that a Texas Red-CoA adduct (Yin, J. et al. Proc. Natl. Acad. Sci. U.S.A., 2005, 102, 15815-15820) was used instead of biotin-CoA. The reaction mixture was passed through a G-25 Fast-Desalting column equilibrated in 30 mM HEPES, pH 7.4, 150 mM NaCl to remove any free biotin or dye molecules.

Fluorescence Anisotropy.

A primary FA experiment was performed by incubating 100 nM TMR-labeled bicyclic peptide with 2 μM TNFα in the blocking buffer. The full FA titration experiment was similarly performed by incubating 50 nM labeled bicyclic peptide with varying concentrations (0-6 µM) of TNFα. The FA values were measured on a Molecular Devices Spectramax M5 spectrofluorimeter, with excitation and emission wavelengths at 545 and 585 nm, respectively. Equilibrium dissociation constants ($K_D$) were determined by plotting the fluorescence anisotropy values as a function of TNFα concentration. The titration curves were fitted to the following equation $$Y = \frac{\left(A_{min} + \left(A_{max} \times \frac{Q_b}{Q_f} - A_{min}\right)\left(\frac{(L+x+K_D) - \sqrt{(L+x+K_D)^2 - 4Lx}}{2L}\right)\right)}{\left(1 + \left(\frac{Q_b}{Q_f} - 1\right)\left(\frac{(L+x+K_D) - \sqrt{(L+x+K_D)^2 - 4Lx}}{2L}\right)\right)}$$

where Y is the measured anisotropy at a given TNFα concentration x; L is the bicyclic peptide concentration; Qb/Qf is the correction fact for dye-protein interaction; $A_{max}$ is the maximum anisotropy when all the peptides are bound to TNFα, while $A_{min}$ is the minimum anisotropy.

Peptide Sequencing by PED-MS.

Beads containing the encoding linear peptides were placed into individual wells of an AcroPrep 96-well filter plate (Pall Corporation, PN5030) with one bead per well. To each well was added a freshly mixed solution containing 25 µL of pyridine/water (v/v 2:1) plus 0.1% triethylamine and 25 µL of Fmoc-OSu (2 µmol) and phenyl isothiocyanate (100 µmol) in dry pyridine. The reaction was allowed to proceed for 6 min and drained by a universal vacuum manifold system designed for 96-well plates (United Chemical Technologies, Inc.). The bead was washed five times with DCM and once with TFA, and incubated with 100 µL of TFA (2×6 min). The bead was washed with DCM and pyridine and PED cycle was repeated for 11 times. After the last PED cycle, the N-terminal Fmoc group was removed by treatment with 20% piperidine in DMF. For MALDI-TOF analysis, each bead was treated with 100 µL of TFA containing ammonium iodide (1.0 mg) and dimethylsulfide (10 µL) for 20 min to reduce any oxidized Met. The bead was washed with water and transferred into a microcentrifuge tube and treated overnight with 20 µL of CNBr in 70% TFA (40 mg/mL) in the dark. The solvents were evaporated under vacuum to dryness and the peptides released from the bead were dissolved in 5 µL of 0.1% TFA in water. One µL of the peptide solution was mixed with 2 µL of saturated 4-hydroxy-α-cyanocinnamic acid in acetonitrile/0.1% TFA (1:1) and 1 µL of the mixture was spotted onto a MALDI sample plate. Mass spectrometry was performed on a Bruker Microflex MALDI-TOF instrument. The data obtained were analyzed by Moverz software (Proteometrics LLC, Winnipeg, Canada).

Library Synthesis.

The bicyclic peptide library was synthesized on 2.0 g of TentaGel S NH$_2$ resin (90 µm, 0.2 mmol/g). All of the manipulations were performed at room temperature unless otherwise noted. The linker sequence (BBFM) was synthesized with 4 equiv of Fmoc-amino acids, using HBTU/HOBt/DIPEA as the coupling reagents. The coupling reaction was typically allowed to proceed for 1 h, and the beads were washed with DMF (3×) and DCM (3×). The Fmoc group was removed by treatment twice with 20% piperidine in DMF (5+15 min), and the beads were exhaustively washed with DMF (6×). To spatially segregate the beads into outer and inner layers, the resin (after removal of N-terminal Fmoc group) was washed with DMF and water, and soaked in water overnight. The resin was quickly drained and suspended in a solution of Fmoc-OSu (0.26 mmol, 0.50 equiv) and diisopropylethylamine (1.2 mmol or 2.0 equiv) in 30 mL of 55:45 (v/v) DCM/diethyl ether. The mixture was incubated on a carousel shaker for 30 min. The beads were washed with 55:45 DCM/diethyl ether (3×) and DMF (8×) to remove water from the beads and then treated with 5 equiv of di-t-butyl dicarbonate in DMF. Next, the Fmoc group was removed by piperidine treatment and 2 equiv of 4-hydroxymethylbenzoic acid and HBTU/HOBt/DIEA (2:2:4 equiv) were added to the resin. Fmoc-β-Ala-OH (5 equiv) was coupled to the Hmb linker by using DIC/DMAP (5.5:0.1 equiv), and the coupling was repeated twice to drive the reaction to completion. Then, Fmoc-L-Pra-OH, two Fmoc-β-Ala-OH, and Fmoc-L-Dap(Alloc)-OH were sequentially coupled by standard Fmoc/HBTU chemistry. The Boc protecting group on the encoding peptide was removed by treatment with TFA/water/triisopropylsilane (95:2.5:2.5), and the exposed amine was coupled with Fmoc-Arg(Pbf)-OH. The random region was synthesized by the split-and-pool method (Lam, K S et al. *Nature,* 1991, 354, 82-84; Houghten, R A et al. *Nature,* 1991, 354, 84-86; Furka, A et al. *Int. J. Pep. Prot. Res.,* 1991, 37, 487-493; Thakkar, A et al. *ACS Comb. Sci.,* 2013, 15, 120-129; Yin, J. et al. *Proc. Natl. Acad. Sci. USA,* 2005, 102, 15815-15820) using 5 equiv of Fmoc-amino acids and HATU as the coupling agent. The coupling reaction was repeated once to ensure complete reaction at each step. To differentiate isobaric amino acids during PED-MS analysis, 4% (mol/mol) of CD$_3$CO$_2$D was added to the coupling reactions of D-Ala, D-Leu, D-Lys, and Orn, while 4% CH$_3$CD$_2$CO$_2$D was added to the Nle reactions (Thakkar, A et al. *Anal. Chem.,* 2006, 78, 5935-5939). Fmoc-Lys(Mmt)-OH was placed in the middle of the random positions using HATU/DIPEA (4 and 8 equiv) to facilitate the formation of bicyclic compounds. After the entire sequence was synthesized, the Alloc group on the C-terminal Dap residue was removed by treatment with a DCM solution containing tetrakis(triphenylphosphine)palladium (0.25 equiv) and phenylsilane (5 equiv) for 15 min (3×). The beads were sequentially washed with 0.5% diisopropylethylamine in DMF, 0.5% sodium dimethyldithiocarbamate hydrate in DMF, DMF (3×), DCM (3×), and DMF (3×). The resulting free amine was coupled to diallyl protected trimesic acid using HATU/DIPEA (5 equiv, 10 equiv) for 2 h. The allyl protecting groups on trimesic acid scaffold was removed using the same procedure as described for the Alloc group. The lysine Mmt group was removed using 2% TFA/5% triisopropylsilane in DCM for 40 min. The N-terminal Fmoc group was then removed with 20% piperidine in DMF. The beads were washed with DMF (6×), 1 M HOBt in DMF (3×), DMF (3×), and DCM (3×). For peptide cyclization, a solution of PyBOP/HOBt/NMM (5, 5, 10 equiv, respectively) in DMF was mixed with the resin and the mixture was incubated on a carousel shaker for 3 h. The resin was washed with DMF (3×) and DCM (3×) and dried under vacuum for >1 h. Side chain deprotection was carried out with modified reagent K (7.5% phenol, 5% water, 5% thioanisole, 2.5% ethanedithiol, 1% anisole, and 1% triisopropylsilane in TFA) for 1 h. The resin was washed with TFA and DCM and dried under vacuum before storage at −20° C.

Library Screening.

Library resin (100 mg) was swollen in DCM, washed extensively with DMF, doubly distilled H$_2$O, and incubated in 1 mL of blocking buffer (PBS, pH 7.4, 150 mM NaCl, 0.05% Tween 20 and 0.1% gelatin) containing 800 nM biotinylated TNFα overnight at 4° C. The beads were washed with the blocking buffer, suspended in 1 mL of the blocking buffer supplemented with 10 µL of M280 streptavidin-coated Dynabeads (Invitrogen), and incubated for 1 h at 4° C. The magnetic beads were separated from the rest of the resin using a TA Dynal MPC-1 magnetic particle concentrator (Invitrogen). The hits from magnetic screening were transferred into a BioSpin column (0.8 mL, BioRad) and washed exhaustively with 6 M guanidine hydrochloride, water, and the blocking buffer to remove the bound proteins. The second round of screening was performed by incubating the initial hits with 1.5 µM biotinylated TNFα as described above. After washing with the blocking buffer, the beads were suspended in 1 mL of the blocking buffer containing streptavidin-alkaline phosphatase (1 µg/mL final concentration) at 4° C. for 10 min. The beads were quickly washed with 1 mL of the blocking buffer (3×) and 1 mL of a staining buffer (30 mM Tris, pH 8.5, 100 mM NaCl, 5 mM MgCl$_2$, 20 µM ZnCl$_2$) (3×). Next, 1 mL of the staining buffer and 100 µL of a BCIP stock solution (5 mg/mL) were added to the beads and intense turquoise color developed on positive beads in 25 min. The turquoise colored beads were manually removed under a dissecting microscope, and subjected to a third round of screening after extensive washing with PBS, ddH$_2$O, and 8 M guanidine hydrochloride. The resulting beads were incubated overnight at 4° C. with 300 nM Texas-red labeled TNFα in the blocking buffer. The beads were viewed under an Olympus SZX12 microscope equipped with a fluorescence illuminator (Olympus America, Center Valley, Pa.) and the intensely fluorescent beads were manually collected as positive hits.

On-Bead Labeling and Peptide Release:

The positive beads derived from on-bead screening were pooled, washed with water and DMF, and soaked in 60 µL of 1:1 (v/v) water/DMF mixture. The labeling reaction was initiated by the addition of 20 µL of freshly prepared ascorbic acid and copper sulfate solutions (each at 5 mg/mL in water) and 5 µL of tetramethylrhodamine azide in DMSO (10 mM). The reaction was allowed to proceed at room temperature overnight in the dark. The reaction was terminated by extensive washing of the beads with water/DMF, and the beads were transferred into individual microcentrifuge tubes (one bead/tube) and each treated with 5 µL of 0.1 M NaOH solution for 4 h at room temperature in the dark. The solution was neutralized by the addition of 5.5 µL of 0.1 M HCl, transferred to a new tube, evaporated to dryness in a vacuum concentrator, and redissolved in 26 µL of double distilled water to generate a stock solution of ~1 µM bicyclic peptide. The beads containing the linear coding peptides were kept in the original tubes and stored for later PED-MS analysis.

Effect of Bicyclic Peptide on TNFα-TNFR1 Interaction.

Recombinant TNFR1 was purchased from R&D Systems. EZ-Link Plus activated peroxidase, an amine-reactive form of HRP was purchased from Thermo Scientific. TNFR1 was labeled with HRP by combining 50 µL of TNFR1 (1.0 µM) and 4 µL of HRP (2.7 pNl) in 950 pt, of Na$_2$CO$_3$ buffer (0.2 M Na2CO$_3$, 0.15 M NaCl, pH 9.0) for 1 h. The resulting TNFR1-HRP conjugate was treated with NaCNBH$_3$ to reduce the resulting Schiff base and quenched with 20 µl of ethanolamine. A Nunc 96F Maxisorp plate was coated overnight with 100 µL of 5 mg/mL Neutravidin (in 50 mM Na$_2$CO$_3$, pH 9.0) at 4° C. The solution was removed and each well was washed with 100 µL of the blocking buffer containing 3% BSA. Next, 100 µL of 7.5 nM biotinylated TNFα in PBS was added to each well and incubated at 4° C. for 1 h. The wells were quickly washed twice with a washing buffer (0.01% Tween 20 in PBS buffer). Peptides of varying concentrations (50 µL) were added to the wells, followed by the addition of 50 µL of 0.5 nM TNFR1-HRP. After incubation at 4° C. for 1.5 h, the plate was washed twice with the washing buffer and incubated with 100 µL of 3,3',5,5'-tetramethylbenzidine (Sigma) for 30 min. The reaction was quenched by the addition of 100 µL of 1 M phosphoric acid. The absorbance at 450 nm was measured and plotted against the peptide concentration and the IC$_{50}$ value was obtained by curve fitting.

MTT Assay.

WEHI-13VAR fibroblasts (American Type Culture Collection) were seeded at a density of 5×10$^4$ cells/well in 100 µL of culture medium (10% FBS in RPMI 1640) and allowed to grow overnight at 37° C. and 5% CO$_2$. TNFα (0.04 ng/mL final concentration), varying concentrations of peptide (0-25 µM), and actinomycin D (1 µg/mL) were mixed and incubated for 1 h in the CO$_2$ incubator. Next, 50 µL of the resulting mixture was added into each well and the plate was incubated overnight. Ten µL of the MTT labeling reagent (final concentration 0.5 mg/ml) was added to each well and incubated for 4 h. One hundred µL of the MTT solubilization solution (Roche) was added to each well and the plate was let stand in the incubator overnight and the absorbance at 550 nm was measured and plotted as a function of the peptide concentration.

Bicyclic Peptidyl Antagonists of Tumor Necrosis Factor-Alpha

Design and Synthesis of Bicyclic Peptide Library.

Antibodies recognize specific antigens by utilizing six small loops, called the "complementarity determining regions". By grafting two or more flexible loops onto protein scaffolds, other investigators have engineered protein binders of antibody-like affinity and specificity (Koide, A et al. J. Mol. Biol., 1998, 284, 1141-1151; Beste, G et al. Proc. Natl. Acad. Sci. USA, 1999, 96, 1898-1903; Xu, L. H. et al. Chem. Biol., 2002, 9, 933-942; Rutledge, S E et al. J. Am. Chem. Soc., 2003, 125, 14336¬14347; Steiner, D et al. J. Mol. Biol., 2008, 382, 1211-1227). Displaying peptidic or peptidomimetic loops on small-molecule scaffolds can also generate molecules that rival antibodies for binding affinity and specificity. To develop inhibitors against PPIs, a planar structure was chosen as the scaffold, in order to maximize the surface area of the resulting molecules and therefore their ability to interact with flat protein surfaces. To test the validity of this approach, a bicyclic peptide library was designed by "wrapping" a peptide sequence of 6-10 random residues around a trimesoyl group (FIG. 1). Peptide cyclization was mediated by the formation of three amide bonds between trimesic acid and the N-terminal amine, the side chain of a C-terminal L-2,3-diaminopropionic acid (Dap), and the side chain of a fixed lysine within the random region. The resulting bicyclic peptides contained 3-5 random residues in each ring. The random sequence was constructed with a 25-amino acid set selected based on their structural diversity, metabolic stability, and commercial availability. It included 10 proteinogenic α-L-amino acids [Ala, Arg, Asp, Gln, Gly, His, Ile, Ser, Trp, and Tyr], 5 nonproteinogenic α-L-amino acids [L-4-fluorophenylalanine (Fpa), L-norleucine (Nle), L-ornithine (Orn), and L-phenylglycine (Phg)], and 10 a-D-amino acids [D-2-naphthylalanine (D-Nal), D-Ala, D-Asn, D-Glu, D-Leu, D-Lys, D-Phe, D-Pro, D-Thr, and D-Val]. This library has a theoretical diversity of 1.0× $10^{14}$. In practice, the library size is limited by the amount of resin employed and typically on the order of $10^7$ (vide infra). Although the actual diversity represents only a very small fraction of all possible structures, the library compounds can sample a large structural space. Once an active compound is identified, its affinity and specificity for the desired target may be improved by synthesizing and screening a second-generation library containing the analogs of the initial hit. To maximize the structural space while keeping the molecular weight to a minimum (e.g., <2000), it was concluded that in addition to the 20 proteinogenic amino acids, unnatural amino acids and potentially nonpeptidic building blocks can also be employed and such compound libraries can be most conveniently prepared by chemical synthesis.

The main challenge associated with screening chemically synthesized bicyclic peptide libraries is structural determination of the hit compounds; no methodology is yet available to directly sequence bicyclic peptides derived from combinatorial libraries. To overcome this difficulty, the bicyclic peptide library was synthesized in the one bead-two compound format (Joo, S H et al. *J. Am. Chem. Soc.,* 2006, 128, 13000-13009; Liu, T et al. *ACS Comb. Sci.,* 2011, 13, 537-546) on 2.0 g of TentaGel microbeads (90 µm, $2.86 \times 10^6$ beads/g, ~100 pmol peptide/bead). Each library bead was topologically segregated into two different layers, with the outer layer displaying a unique bicyclic peptide and the inner layer containing the corresponding linear peptide as an encoding tag. To spatially segregate the beads, the TentaGel resin was soaked in water, drained, and quickly suspended in 1:1 (v/v) DCM/Et$_2$O containing 0.5 equivalent of N-(9-fluorenylmethoxycarbonyloxy)succinimide (Fmoc-OSu) (Liu, R et al. *J. Am. Chem. Soc.,* 2002, 124, 7678-7680). Because the organic solvent is immiscible with water, only peptides on the bead surface were exposed to and reacted with Fmoc-OSu. The beads were washed with DMF and the remaining free N-terminal amines inside the beads were protected with a Boc group. After removal of the Fmoc group, a p-hydroxymethylbenzoic acid (Hmb) linker was added (for selective release of the bicyclic peptide), followed by the addition of β-Ala, L-propargylglycine (Pra), two β-Ala, and Fmoc-L-Dap(Alloc)-OH. The Pra residue serves as a handle for selective labeling of the bicyclic peptide via click chemistry (vide infra). The Dap residue permits attachment of the bicyclic peptide to the solid support as well as providing a side chain for peptide cyclization. The N-terminal Boc group was then removed from the inner peptides by treatment with trifluoroacetic acid (TFA) and an arginine residue was added to provide a fixed positive charge, which facilitates later peptide sequencing by mass spectrometry. The random region was synthesized by the split-and-pool method (Lam, K S et al. *Nature,* 1991, 354, 82-84; Houghten, R A et al. *Nature,* 1991, 354, 84-86; Furka, A et al. *Int. J. Pep. Prot. Res.,* 1991, 37, 487-493) and an N$^\varepsilon$-4-methoxytrityl (Mmt)-protected lysine was added in the middle of the random sequence to provide a side-chain amine for peptide cyclization. Following completion of the linear peptide synthesis, the Mmt group was removed using 2% TFA in DCM and replaced with an Fmoc group (the Mmt group was partially removed during deprotection of the Alloc group). The Alloc group on the C-terminal Dap was removed by treatment with Pd(PPh$_3$)$_4$ and the exposed side chain amine was acylated with diallyl trimesic acid. Finally, the allyl (on the trimesoyl moiety) and Fmoc protecting groups (on the N-terminus and the lysine side chain) were removed and the surface peptides were cyclized by treatment with benzotriazol-1-yl-oxy-tris(pyrrolidino)phosphonium hexafluorophosphate (PyBOP). The peptides inside the beads were unaffected by the cyclization procedure due to lack of the Dap residue and remained in the linear form to serve as encoding tags. Note that macromolecular targets (e.g., proteins) cannot diffuse into the bead interior and thus the linear encoding peptides do not interfere with library screening. The symmetry of the trimesoyl unit ensured that a single bicyclic product was formed on each bead.

Figure 6:
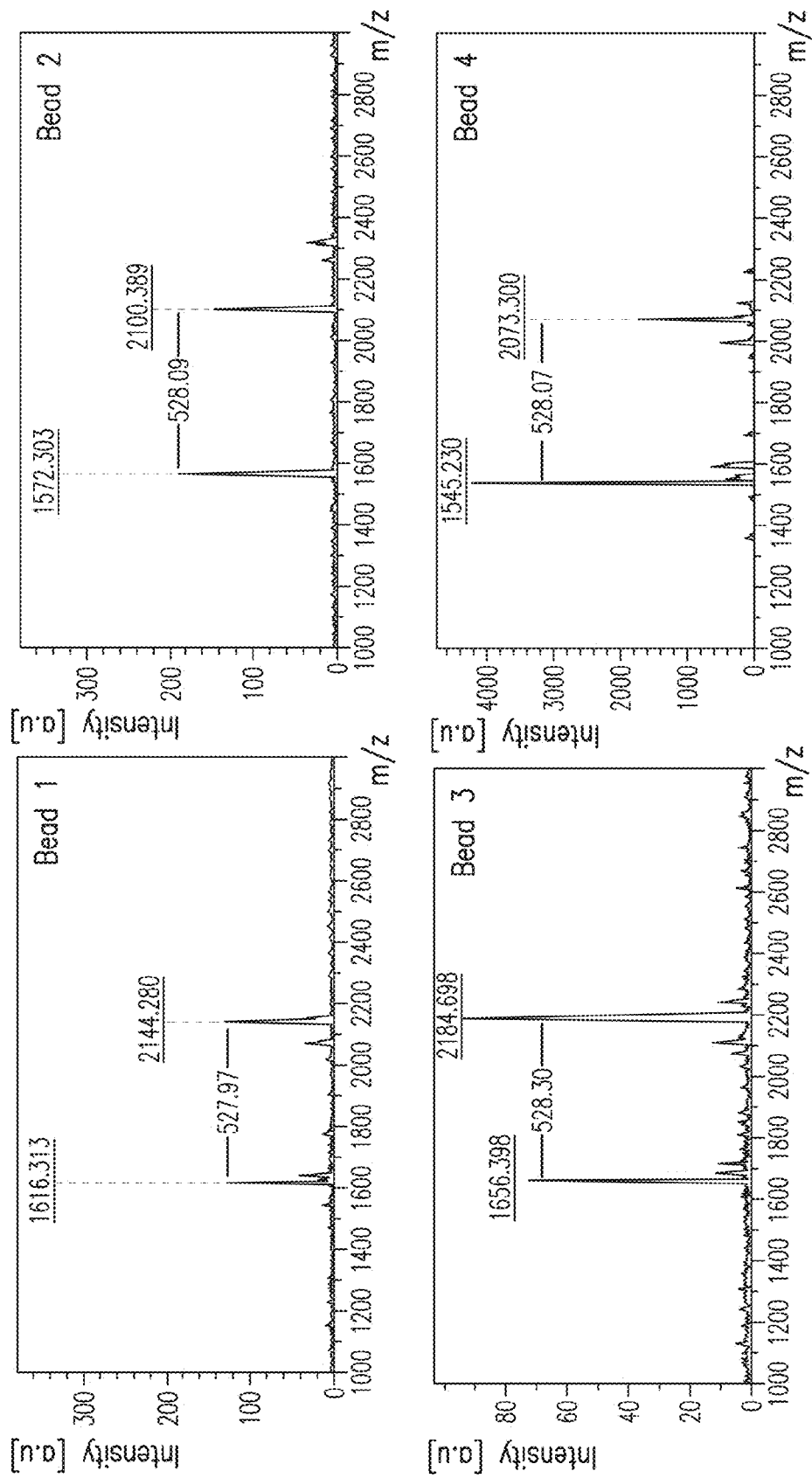
FIG. 6 shows mass spectra showing the quality of the bicyclic peptide library. Ten beads were randomly selected from the library and treated with CNBr, and the peptides released were analyzed by MALDI-TOF MS. Each bead produced a pair of peaks separated by 528 amu.
Figure 6:
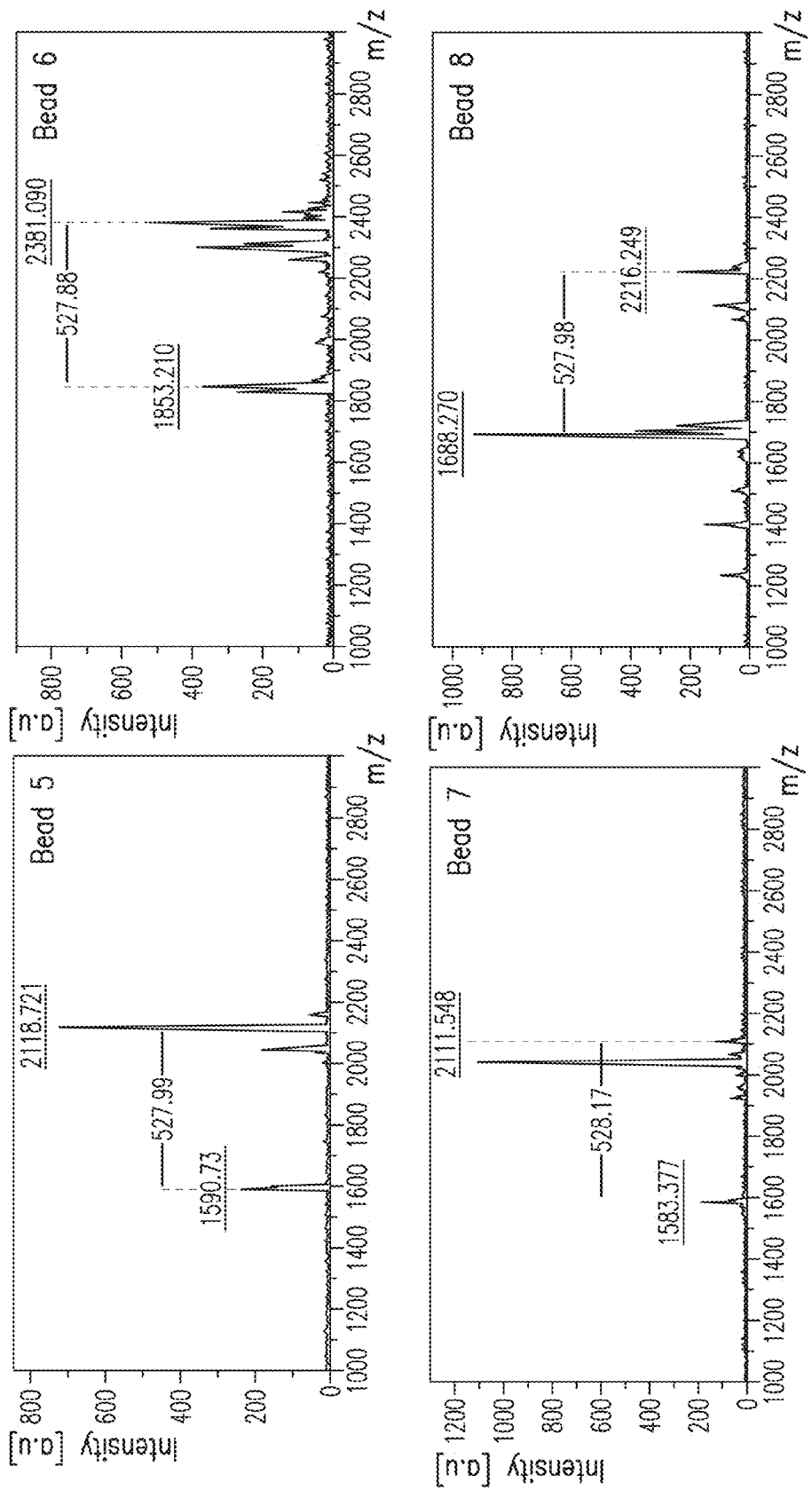
Figure 6:
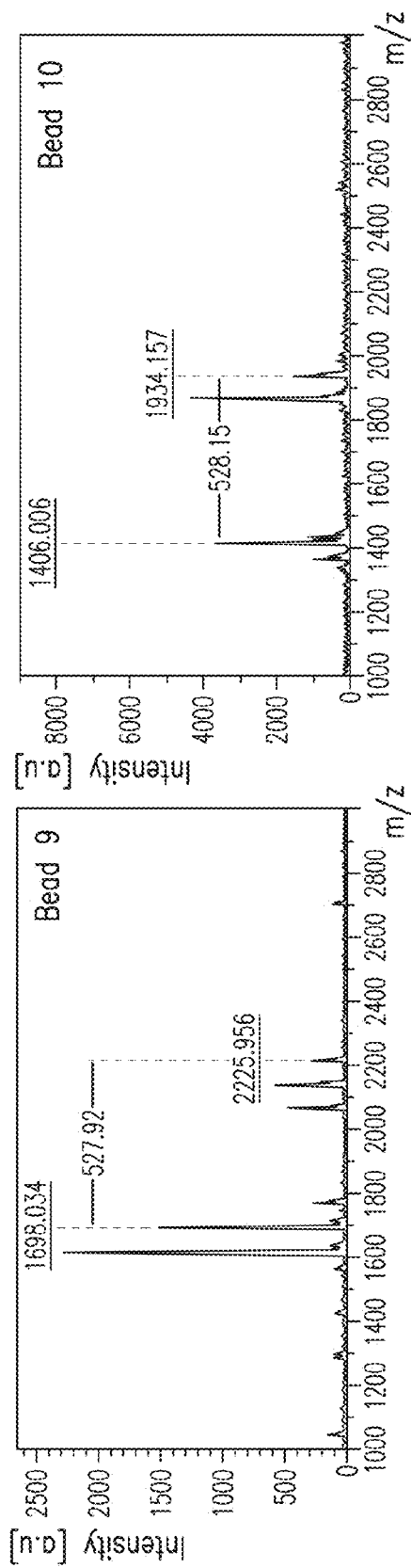

To assess the quality of the bicyclic library, 10 beads were randomly selected for MS analysis. The peptide on each bead was released by CNBr cleavage after the C-terminal methionine and analyzed by MALDI-TOF MS. For each of the 10 beads, the released peptides showed two peaks separated by 528 mass units, as expected for the molecular mass difference between the linear encoding sequence (m/z M) and the corresponding bicyclic peptide (m/z M+528) (FIG. 6). Previous studies have shown that on-resin cyclization of hexa- and longer peptides with PyBOP is essentially quantitative for ?99.96% of the sequences (Joo, S H et al. *J. Am. Chem. Soc.,* 2006, 128, 13000-13009; Thakkar, A et al. *ACS Comb. Sci.,* 2013, 15, 120-129).

Library Screening Against TNFα.

The bicyclic peptide library was subjected to four rounds of screening against TNFα. TNFα was expressed in *Escherichia coli* as a fusion to an N-terminal ybbR tag (MVLDSLEFIASKL; SEQ ID NO.: 66) and specifically labeled at the ybbR tag with a biotin or fluorescent dye by using phosphopantetheinyl transferase Sfp (Yin, J. et al. *Proc. Natl. Acad. Sci. USA,* 2005, 102, 15815-15820). During the first round, 100 mg of the bicyclic peptide library (~$3 \times 10^5$ beads) was incubated with biotinylated TNFα (0.8 µM) and streptavidin-coated magnetic particles. The resulting magnetic (positive) beads (~400 beads) were separated from the rest of library beads by applying a magnetic field to the wall of the container; the positive beads were attracted to the wall, while the negative beads settled to the bottom of the container (magnetic sortin) (Kodadek, T and Bachhawat-Sikder, K. *Mol. BioSyst.,* 2006, 2, 25-35; Hu, B H et al. *Anal. Chem.,* 2007, 79, 7275-7285). The ~400 beads were washed, incubated again with the biotinylated TNFα (1.5 µM), and subjected to a second round of screening using an on-bead enzyme-linked assay and a streptavidin-alkaline phosphatase (SA-AP) conjugate (Sweeney, M C et al. *Biochemistry,* 2005, 44, 14932-14947). Binding of TNFα to a bead recruits SA-AP to the bead surface and upon the addition of 5-bromo-4-chloro-3-indolyl phosphate (BCIP), produces a turquoise colored precipitate on that bead. This procedure resulted in 150 intensely turquoise colored beads, which were manually isolated using a micropipette with the aid of a dissecting microscope and washed exhaustively to remove the bound proteins and dye molecules. During the third round of screening, the 150 beads were incubated with Texas-red labeled TNFα (0.3 µM) and the 44 most fluorescent beads were manually isolated under a fluorescence microscope.

Figure 2A:
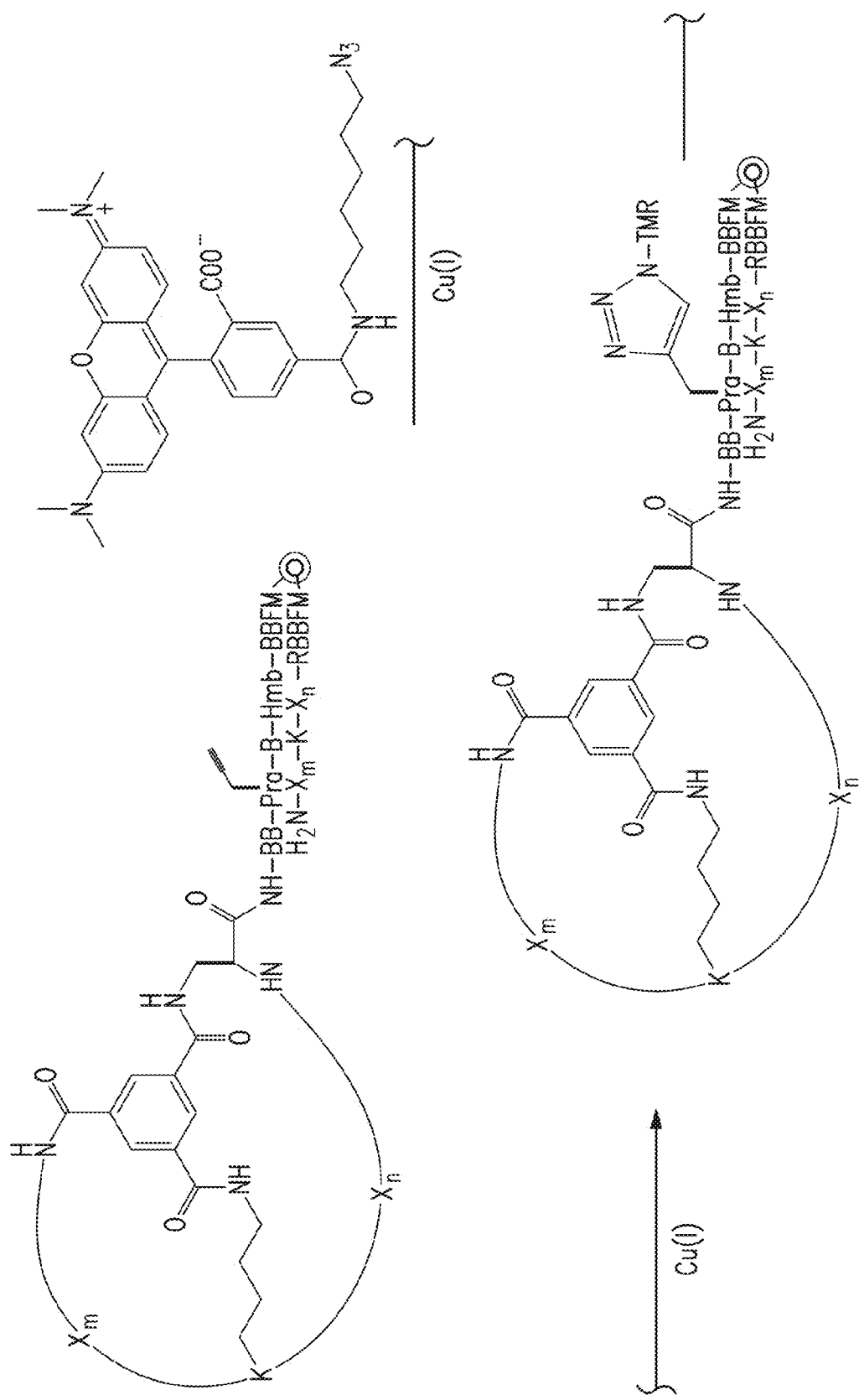
FIG. 2 shows Solution-phase screening of initial hits ($4^{th}$ round of screening). 2A—Selective labeling of bicyclic peptides with TMR and their release from individual beads by base hydrolysis. 2B— Evaluation of the 44 released bicyclic peptides for binding to TNFα in solution by fluorescent anisotropy using a fixed concentration of TNFα (5 μM) and TMR-labeled bicyclic peptide (100 nM).
Figure 2A:
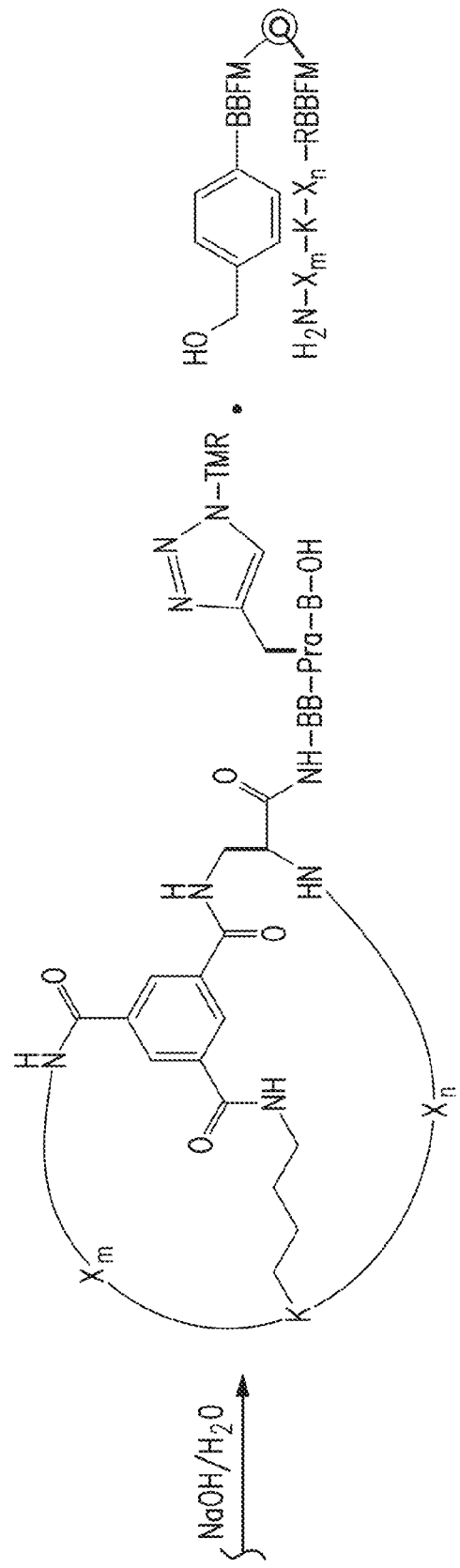
Figure 2B:
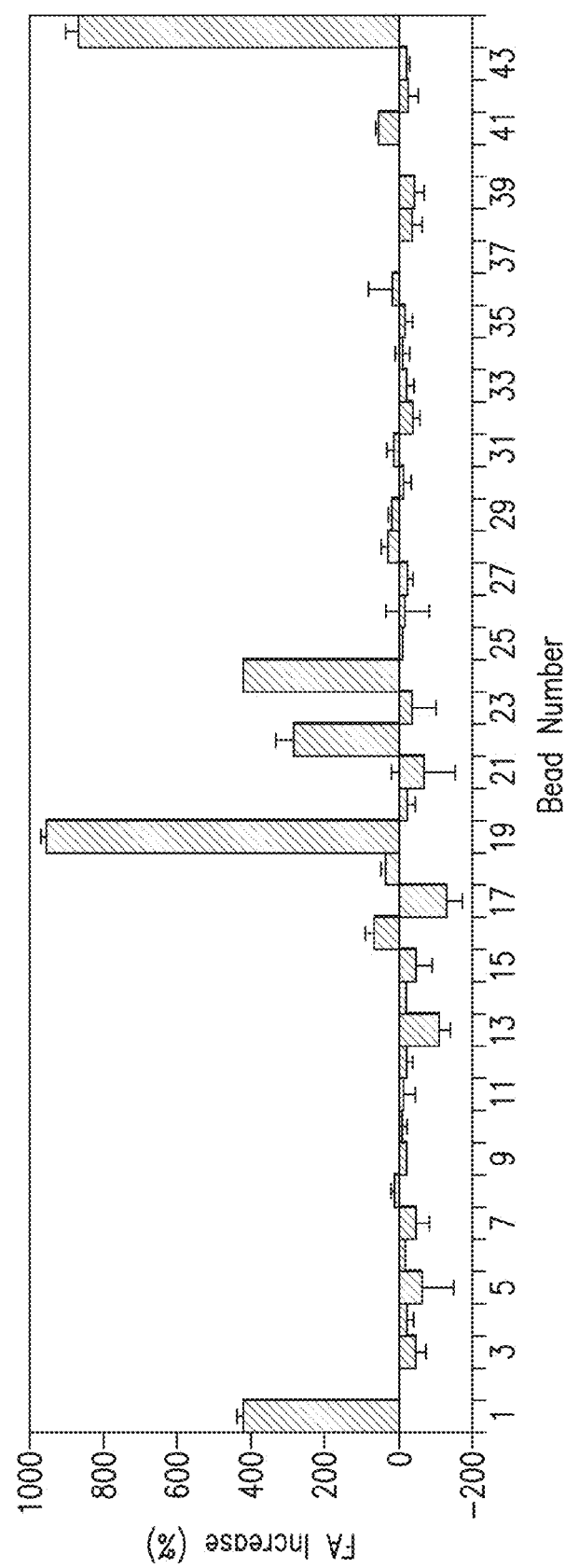
Figure 7:
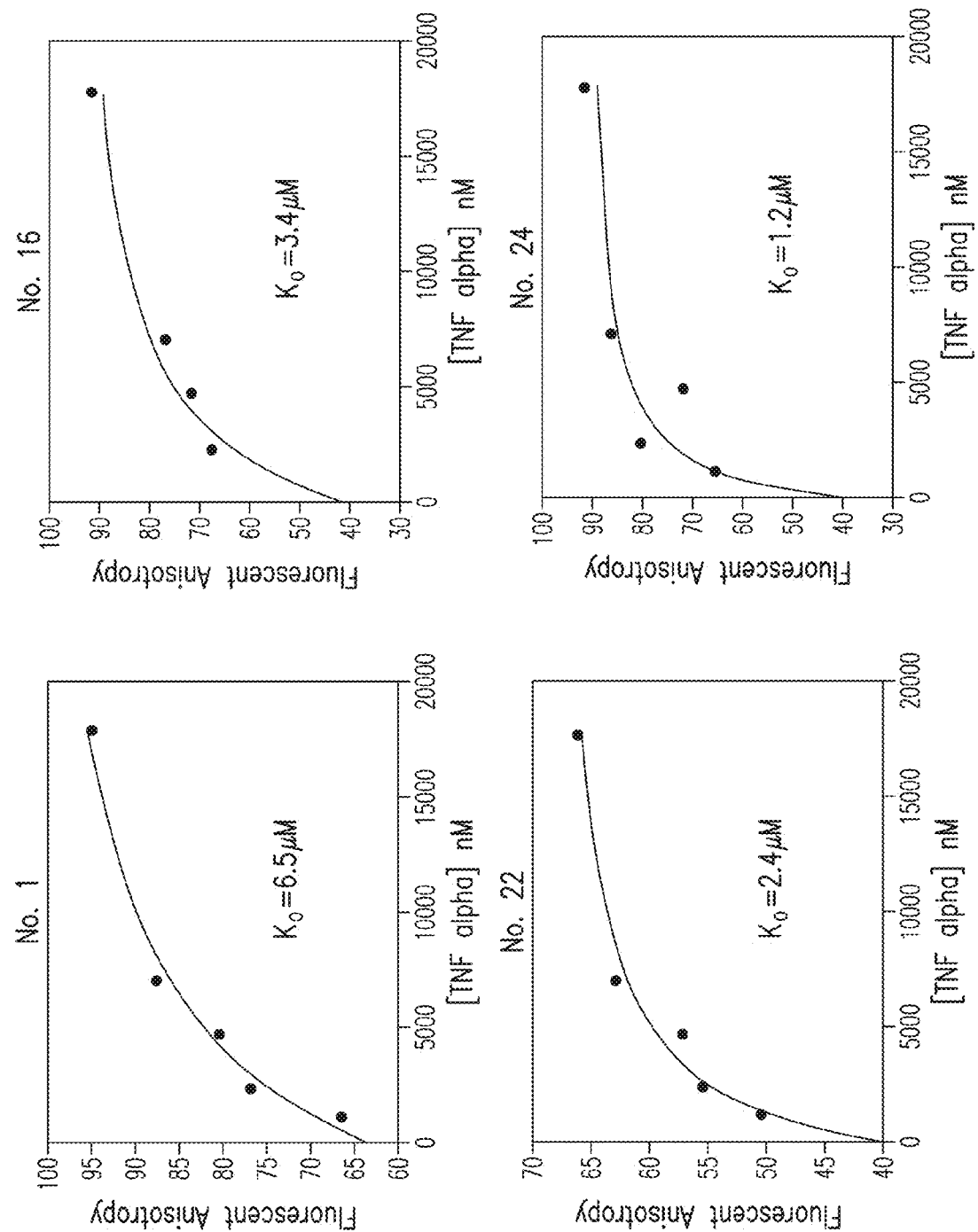
FIG. 7 shows FA analysis of TNFα Binding by bicyclic peptides released from single beads. For each bead, the released TMR-labeled bicyclic peptide (~50 nM) was incubated with varying concentrations of TNFα (0-18 μM) and the FA values are plotted against TNFα concentration. Curve fitting (as described in main text) gave the $K_D$ values.
Figure 7:
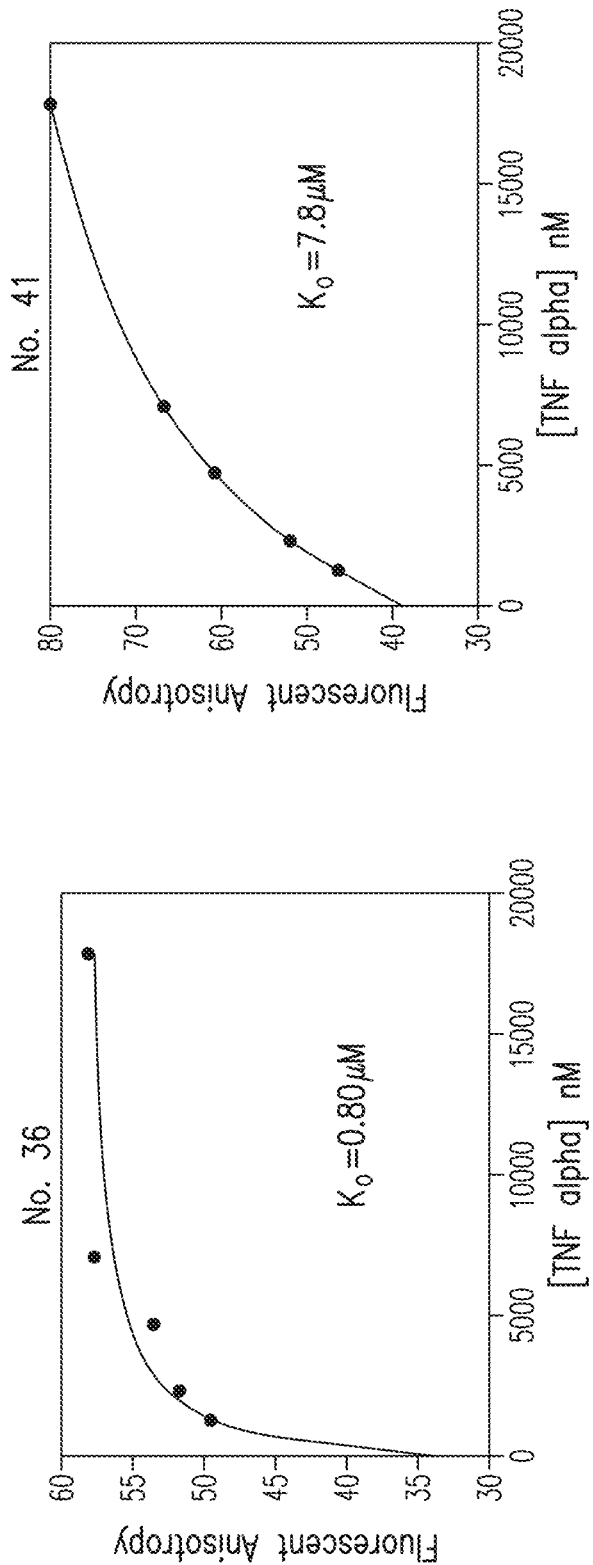
Figure 8A:
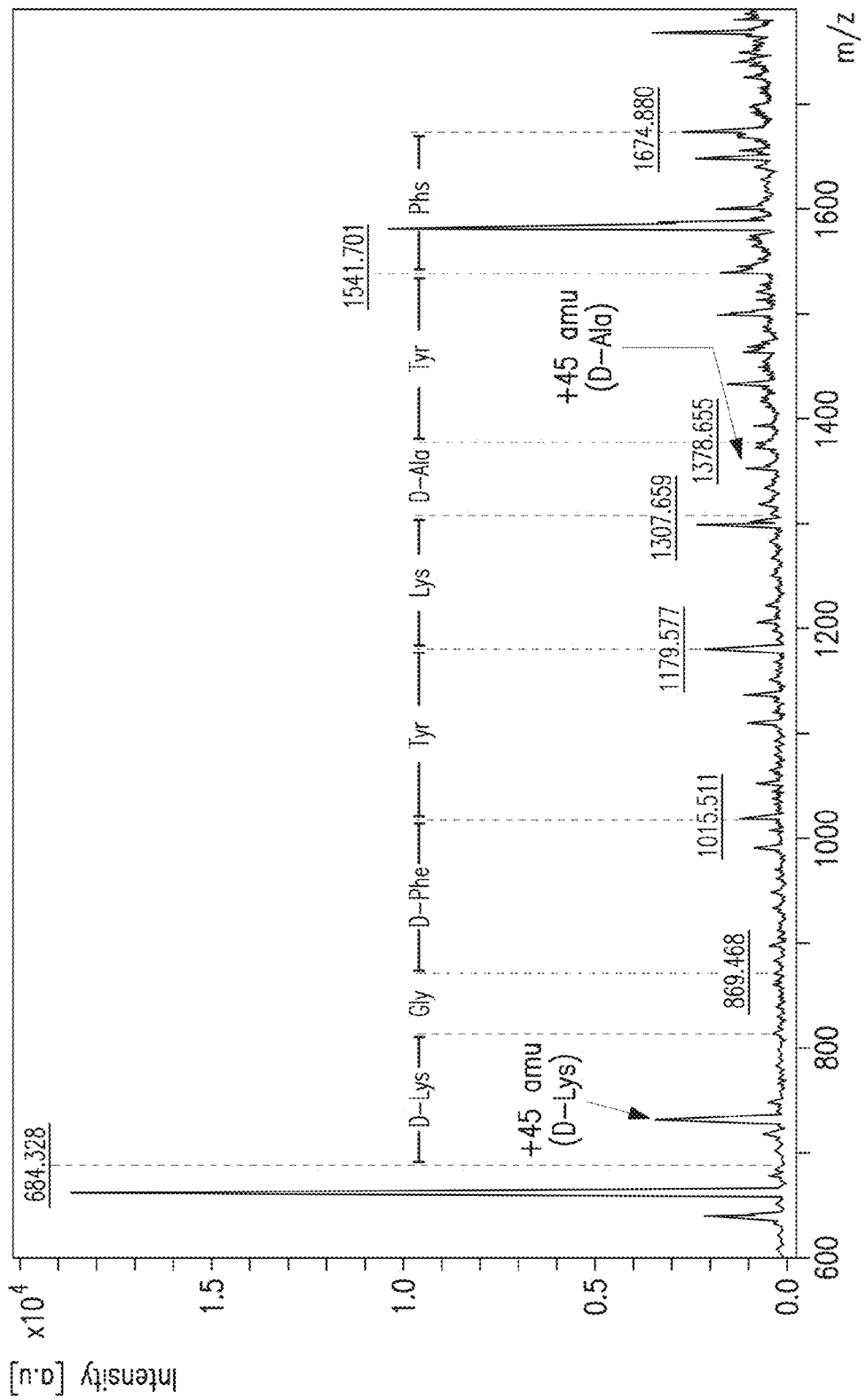
FIG. 8 shows sequence determination of positive hits by PED-MS. Positive beads after the solution-phase screening ($4^{th}$ round) were subjected to 11 cycles of PED, and the peptides were released from each bead by CNBr, and analyzed by MALDI-TOF MS. M*, homoserine lactone.
Figure 8B:
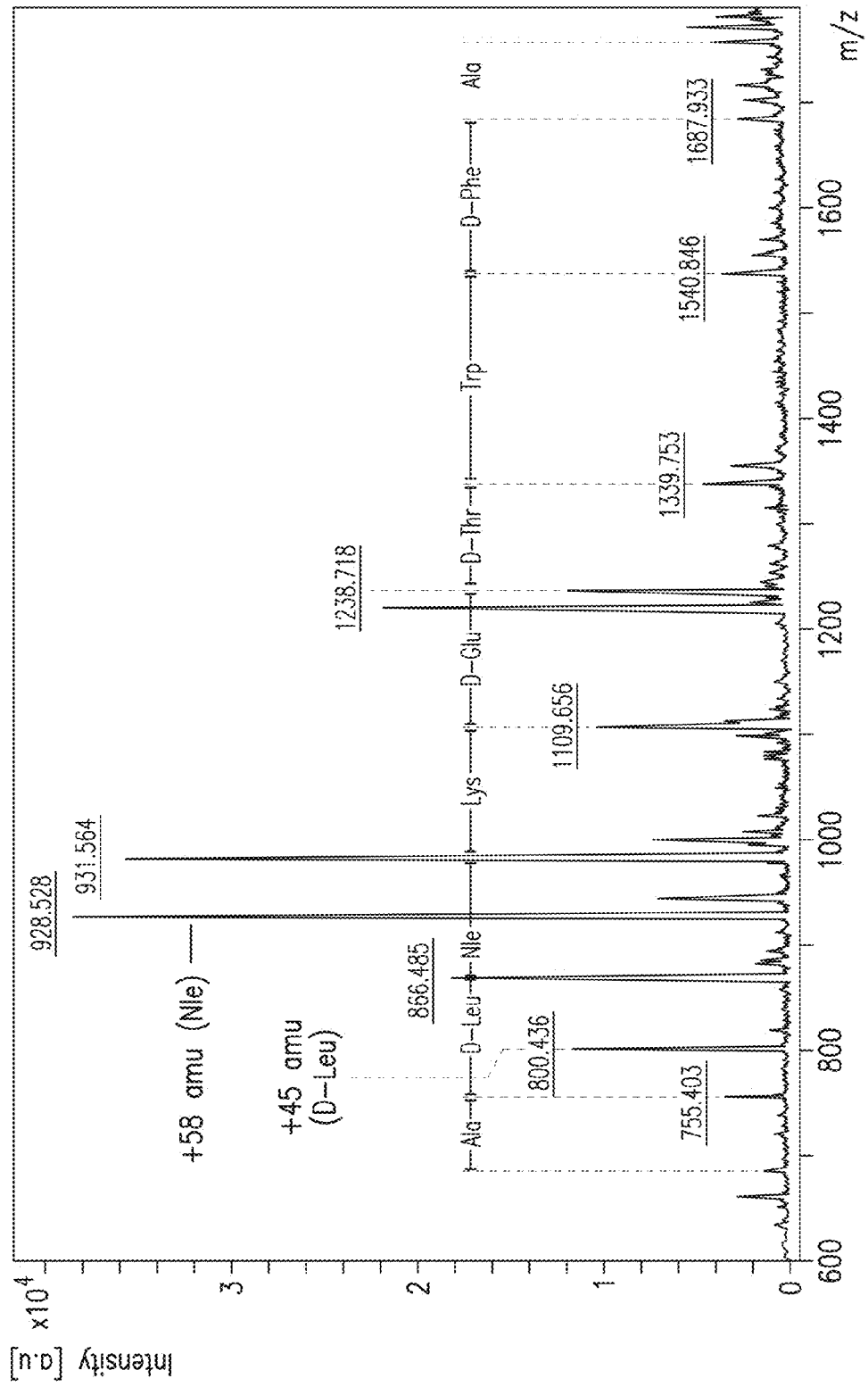
Figure 9A:
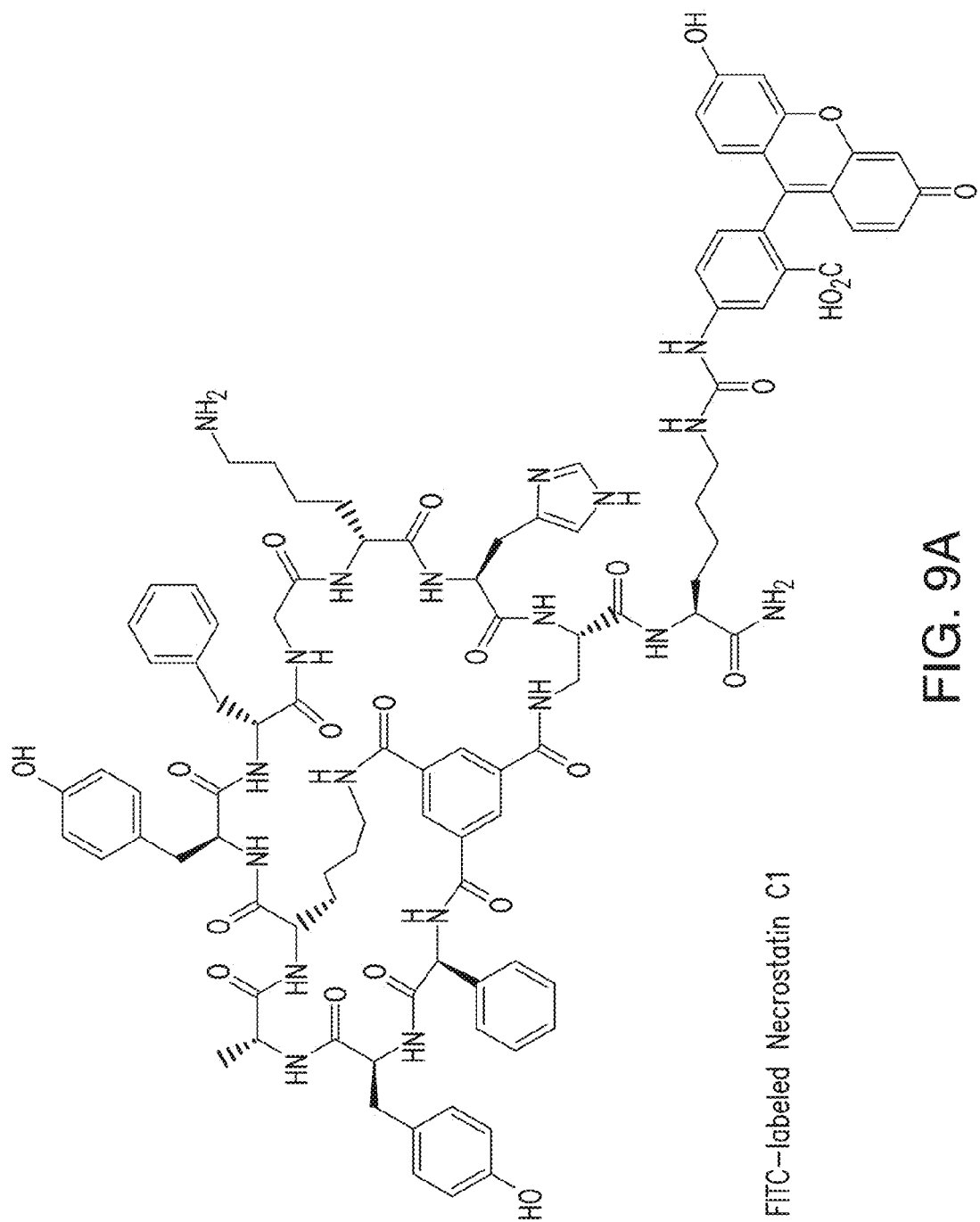
FIG. 9 shows—9A, Structures of FITC-labeled Necrostatin C1 and C2, the linear and monocyclic analogs of C1, and a control bicyclic peptide. 9B, Binding of C1 analogs and control bicyclic peptide to TNFα as determined by FA.
Figure 9A:
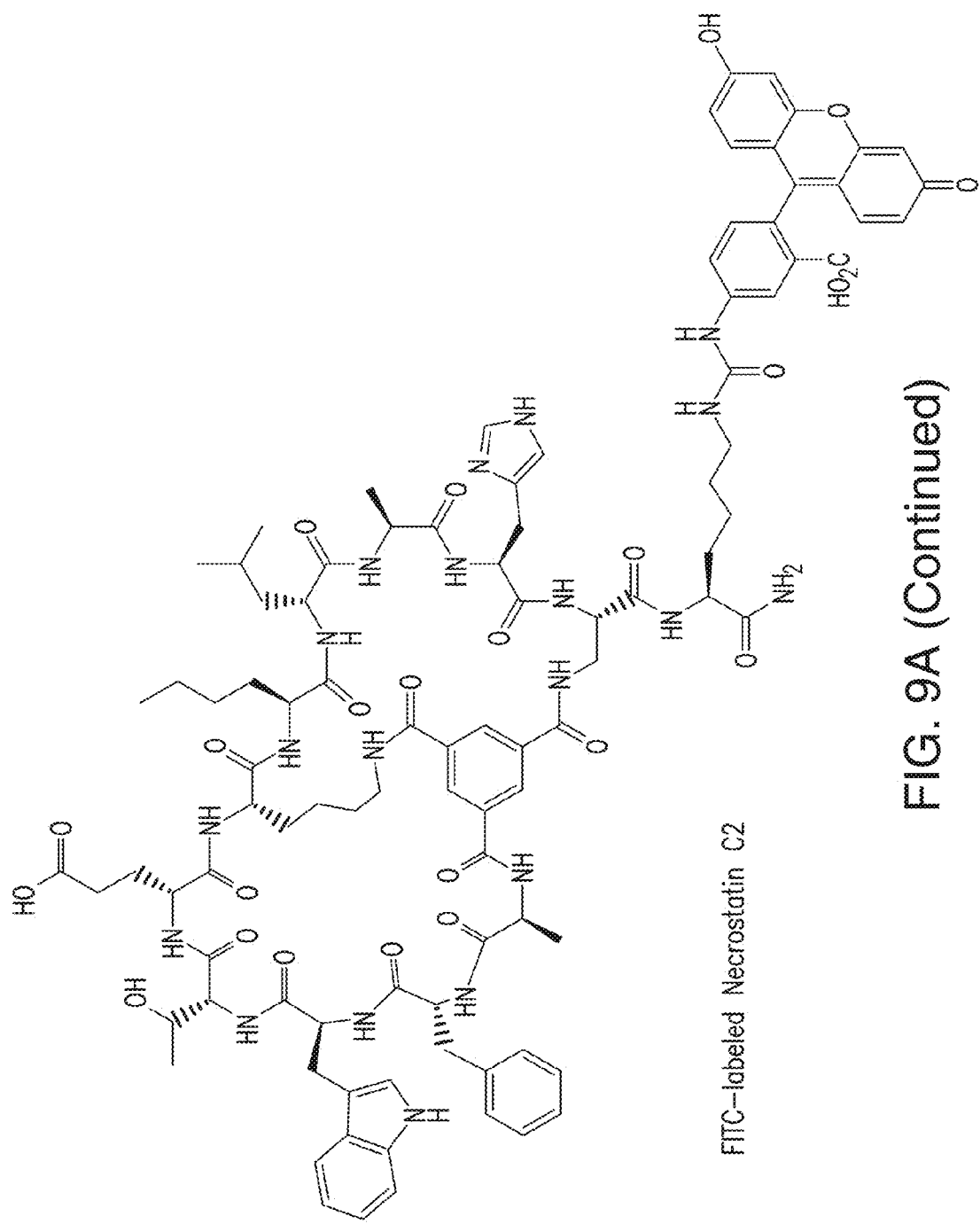
Figure 9A:
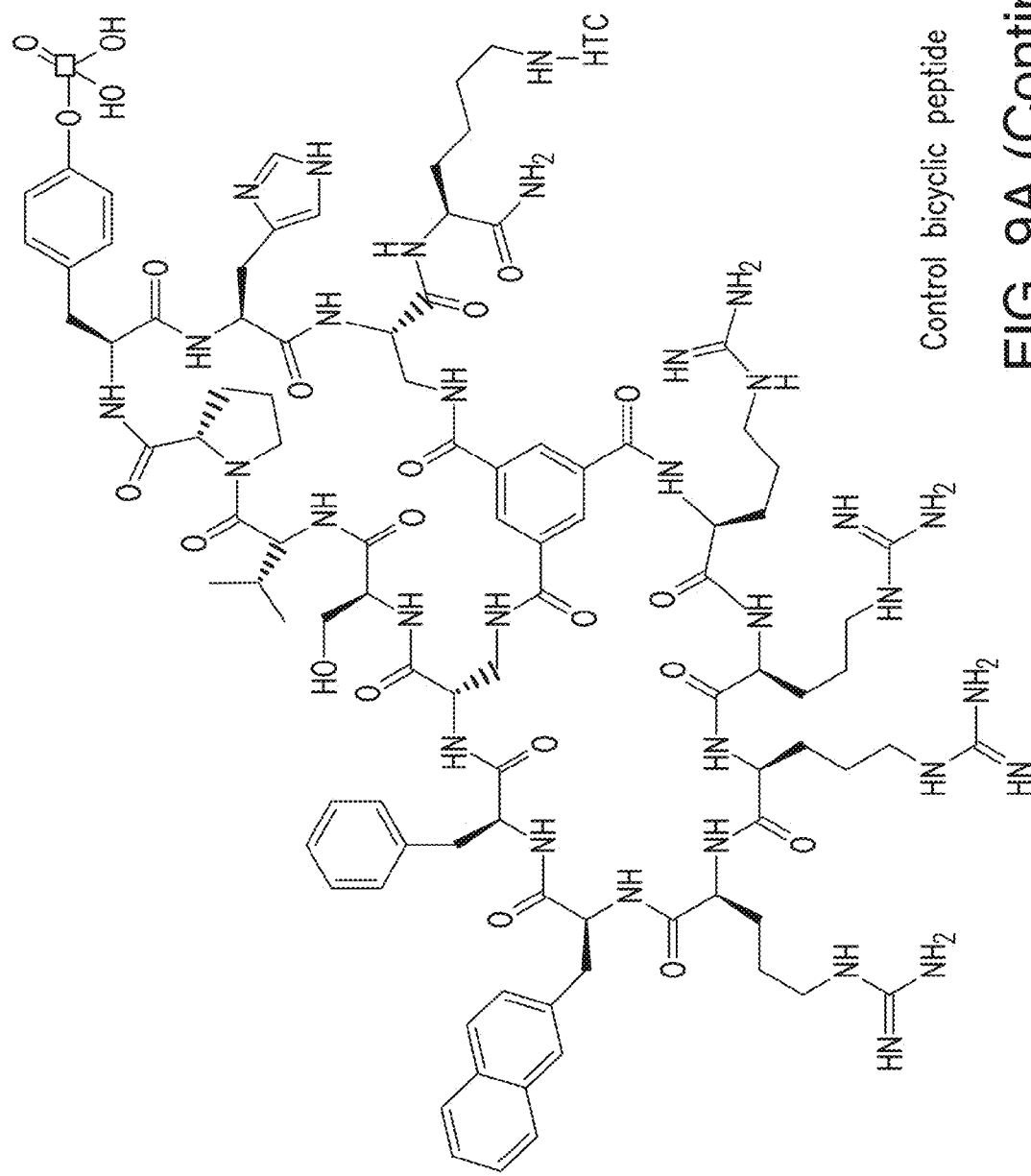
Figure 9A:
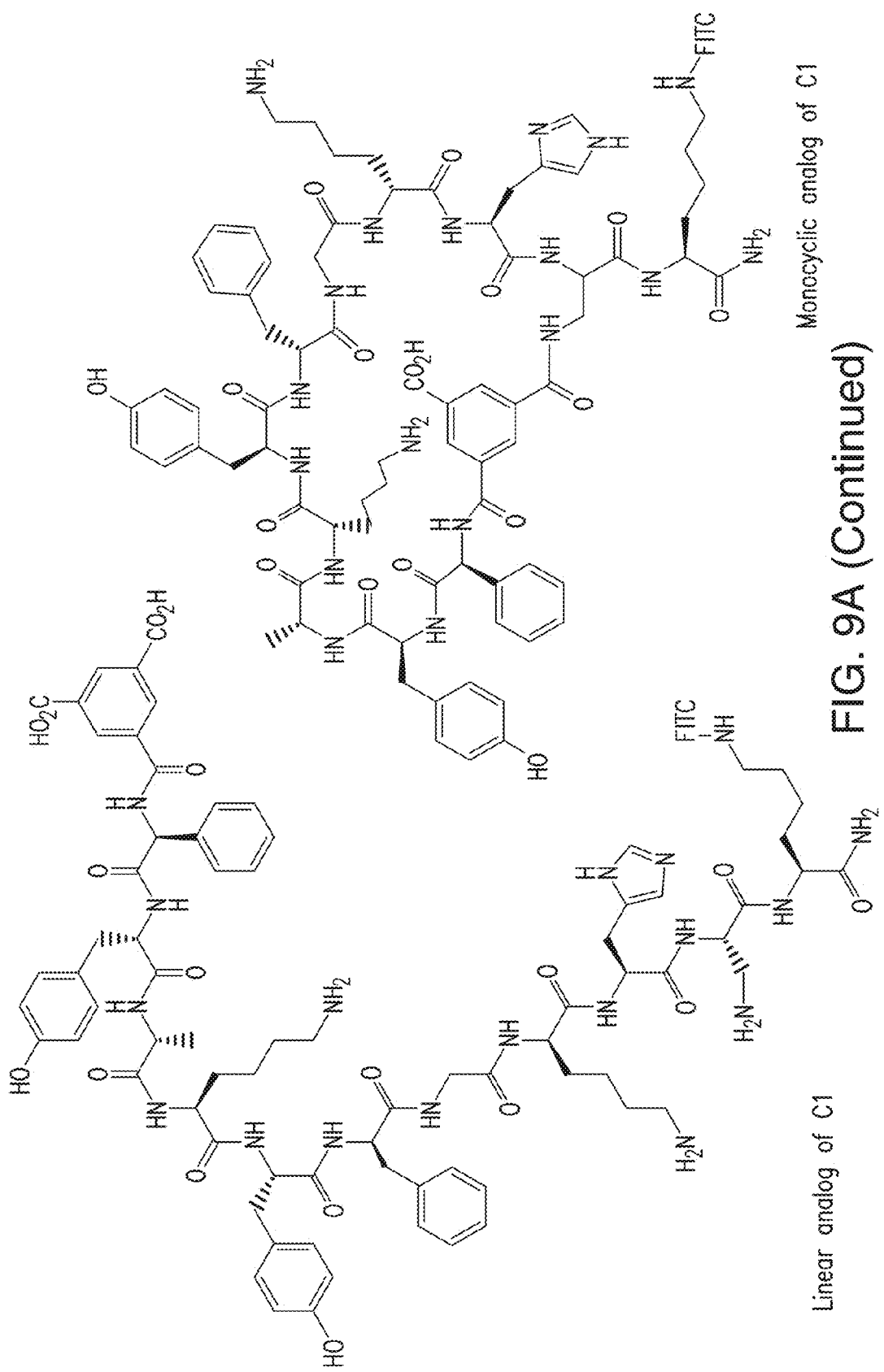

Finally, the 44 hits derived from the above on-bead assays were individually tested for binding to TNFα in solution by fluorescence polarization (FA) (fourth round) (Liu, T et al. *ACS Comb. Sci.,* 2011, 13, 537-546; Hintersteiner, M et al. *Chem. Biol.,* 2009, 16, 724-735). Thus, the 44 beads were treated with tetramethylrhodamine (TMR) azide in the presence of Cu(I), resulting in selective labeling of the bicyclic peptides at the Pra residue (FIG. 2a). The beads were then placed into individual microcentrifuge tubes (1 bead/tube) and the TMR-labeled bicyclic peptide was released from each bead by treatment with 0.1 M NaOH, which selectively hydrolyzed the Hmb ester linkage associated with the bicyclic peptide. After neutralization and evaporation of solvent, the released bicyclic peptide from each bead was dissolved in water to give a stock solution of ~1 µM. FA measurements were also carried out in two stages. During the initial stage, each of the 44 bicyclic peptides (100 nM) was incubated with a single concentration of TNFα (5 µM) and the anisotropy increase relative to the control (no TNFα) was measured. Out of the 44 peptides, 12 showed an increase of >15% (FIG. 2b). These 12 bicyclic peptides were further analyzed at varying concentrations of TNFα (0-18 µM) to generate a full binding curve for each peptide, from which a dissociation constant ($K_D$) was calculated. Complete binding curves were obtained for 6 of the 12 bicyclic peptides (bead No. 1, 16, 22, 24, 36, and 41) and their KD values ranged from 0.8 to 7.8 µM (FIG. 7). No significant TNFα binding was observed for the bicyclic peptides released from the other 6 beads (No. 18, 19, 28, 29, 31, and 44). Next, for the 6 bicyclic peptides that showed significant TNFα binding, the corresponding beads containing the linear encoding peptides were retrieved from the microcentrifuge tubes and subjected to partial Edman degradation-mass spectrometry (PED-MS) analysis (Thakkar, A et al. *Anal. Chem.*, 2006, 78, 5935-5939). Two of the beads (hits No. 1 and 36) produced mass spectra of sufficient quality, from which unambiguous, complete sequences of bicyclo(Phg-Tyr-D-Ala-Lys-Tyr-D-Phe-Gly-D-Lys-His-Dap; SEQ ID NO.: 67) and bicyclo(Ala-D-Phe-Trp-D-Thr-Gln-Lys-Nle-D-Leu-Ala-His-Dap; SEQ ID NO. 68) were derived (FIG. 3a and FIG. 8). These compounds are named as Necrostatin C1 and C2 thereafter, respectively.

The fact that only a relatively small number of the hits derived from on-bead screening (6 out of 44 beads) had strong binding to TNFα in solution suggests that many of the initial hits were false positives or weak binders, a common problem associated with on-bead screening which is likely caused by the high ligand densities on the beads (~100 mM) and multi-dentate interactions (i.e., simultaneous interaction of a single TNFα molecule with two or more resin-bound bicyclic peptides) (Chen, X et al. *J. Comb. Chem.*, 2009, 11, 604-611). False negatives are also possible due to certain technical difficulties (e.g., poor aqueous solubility, inefficient release from resin by 0.1 M NaOH due to strong binding to the TentaGel resin, and/or strong binding of a bicyclic peptide to bovine serum albumin which was present in all FA assays). This highlights the importance of this library design, which permits selective release of the bicyclic peptide and therefore solution-phase binding analysis and avoids the need to individually resynthesize all 44 initial hits.

Binding Affinity and Specificity for TNFα.

Figure 3B:
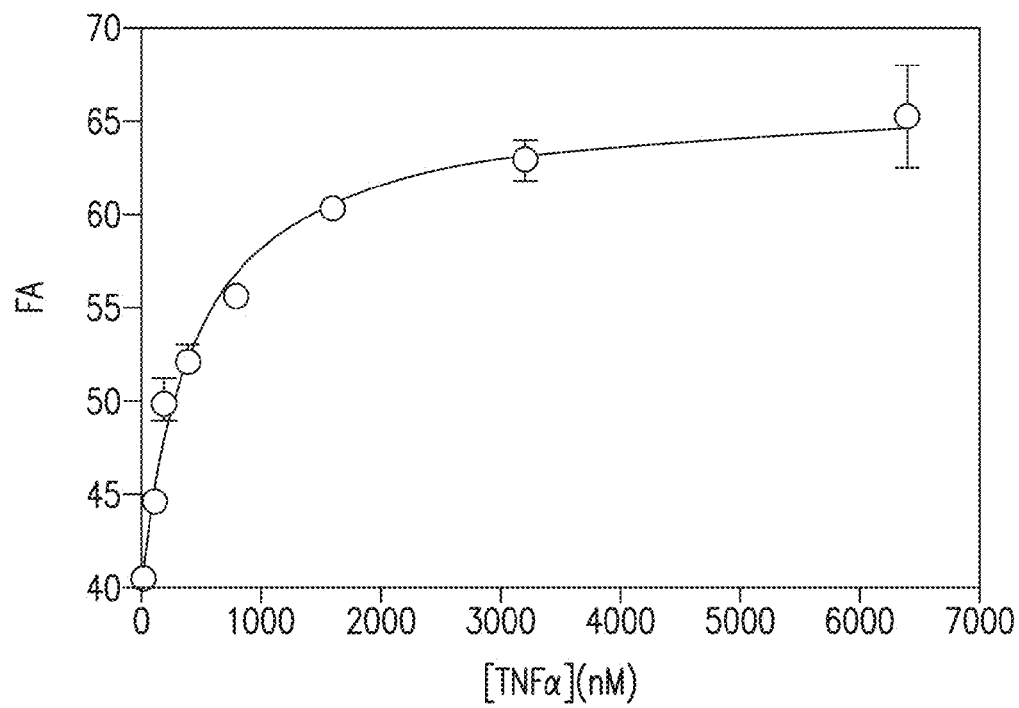
FIG. 3 shows FA analysis of the binding affinity of resynthesized Necrostatin C1 and C2 for TNFα. 3A—Structures of Necrostatin C1 and C2. 3B and 3C—Plot of FA values as a function of TNFα concentration for Necrostatin C1 and C2, respectively.
Figure 3C:
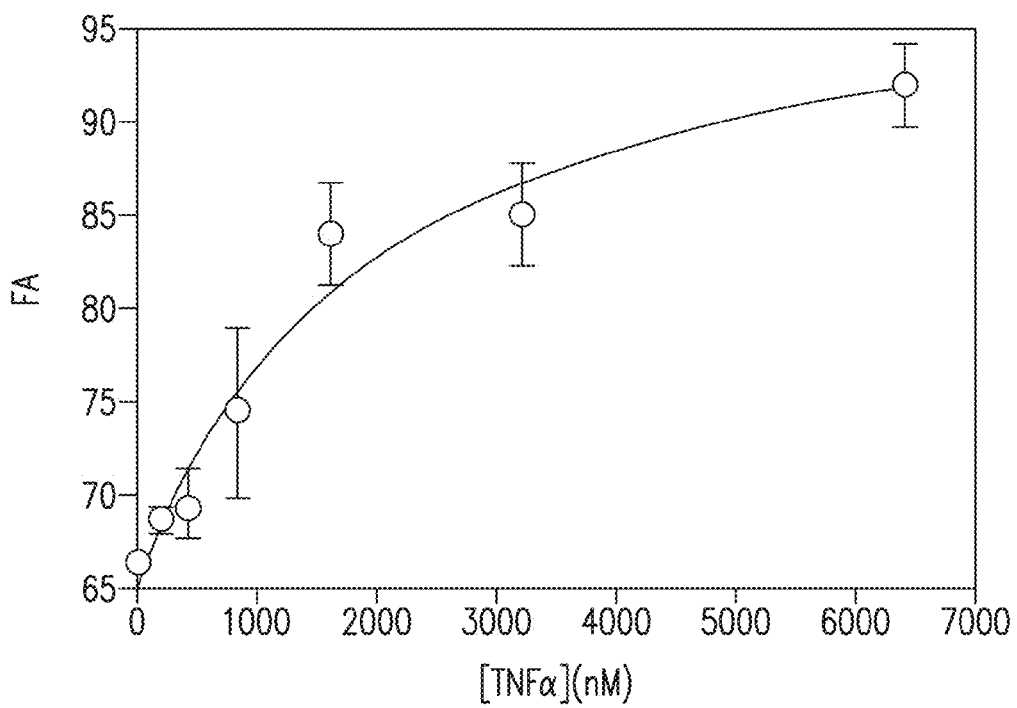
Figure 10A:
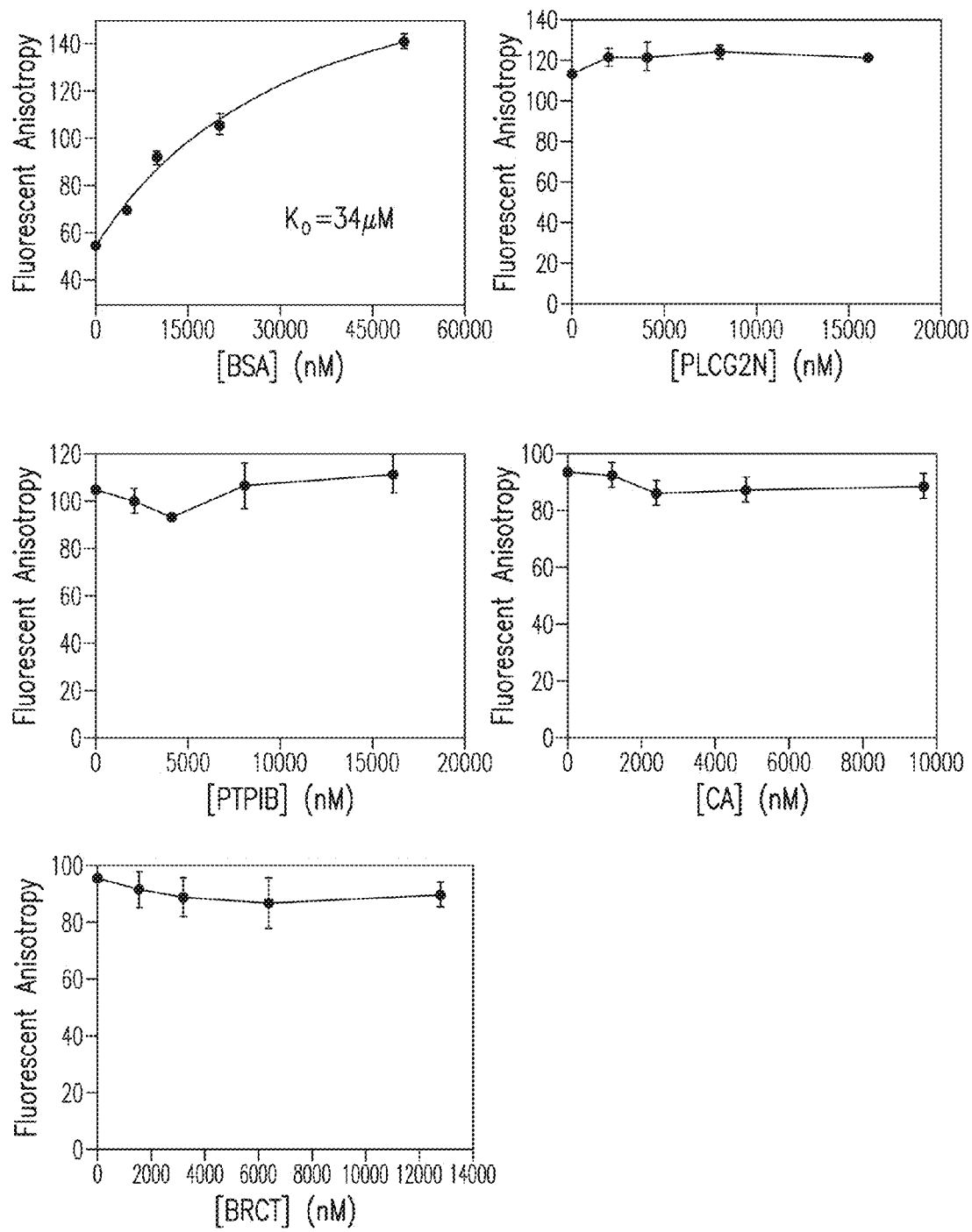
FIG. 10 shows FA analysis of binding of FITC-labeled Necrostatin C1 and C2 to control proteins. BSA, bovine serum albumin; BRCT, GST fusion with the BRCT domain of TopBP1; CA, HIV-1 capsid protein; PLCγ2N, GST fusion with the N—SH2 domain of SH2 of PLCγ; and PTP1B, protein tyrosine phosphatase 1B.
Figure 10B:
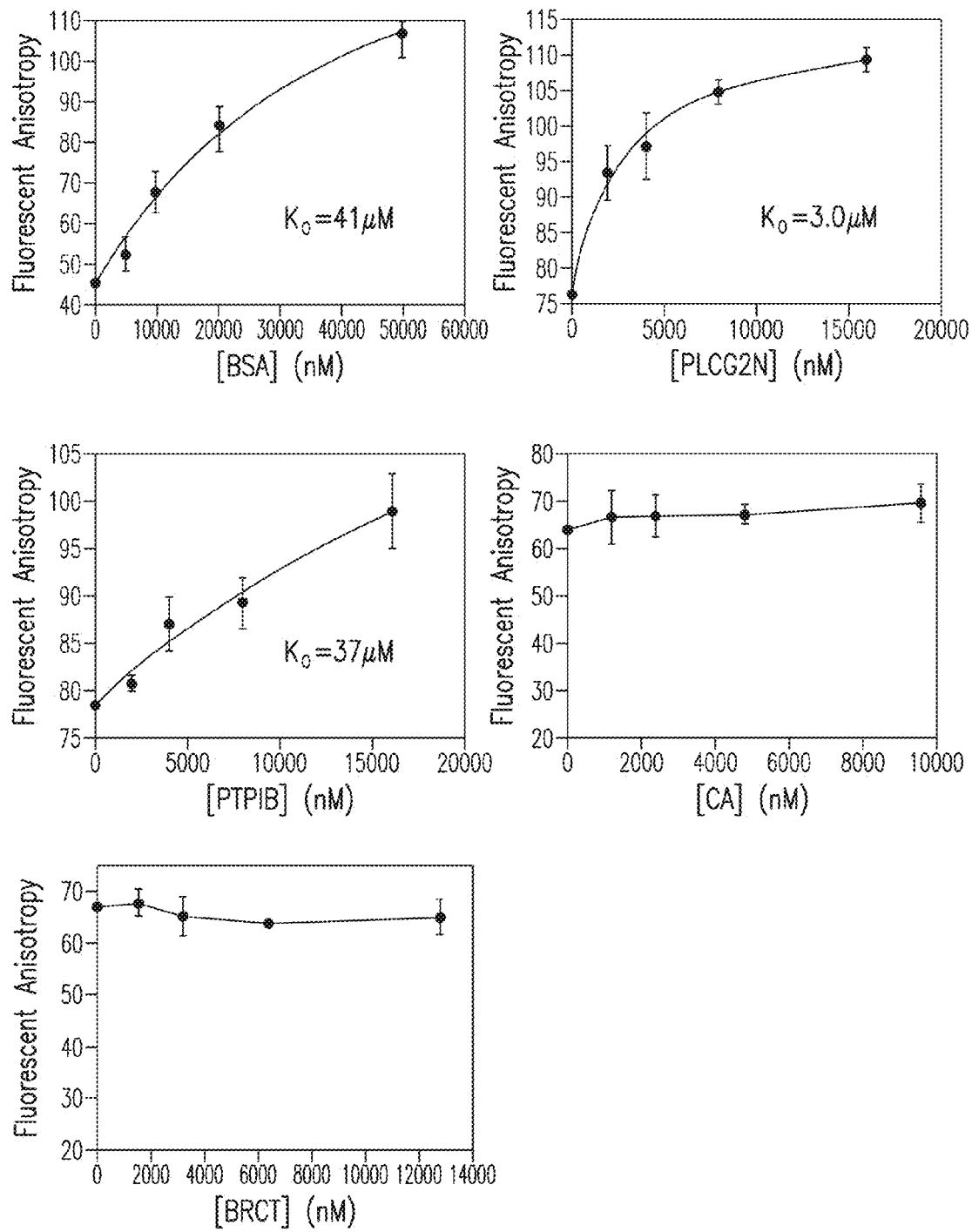
Figure 11:
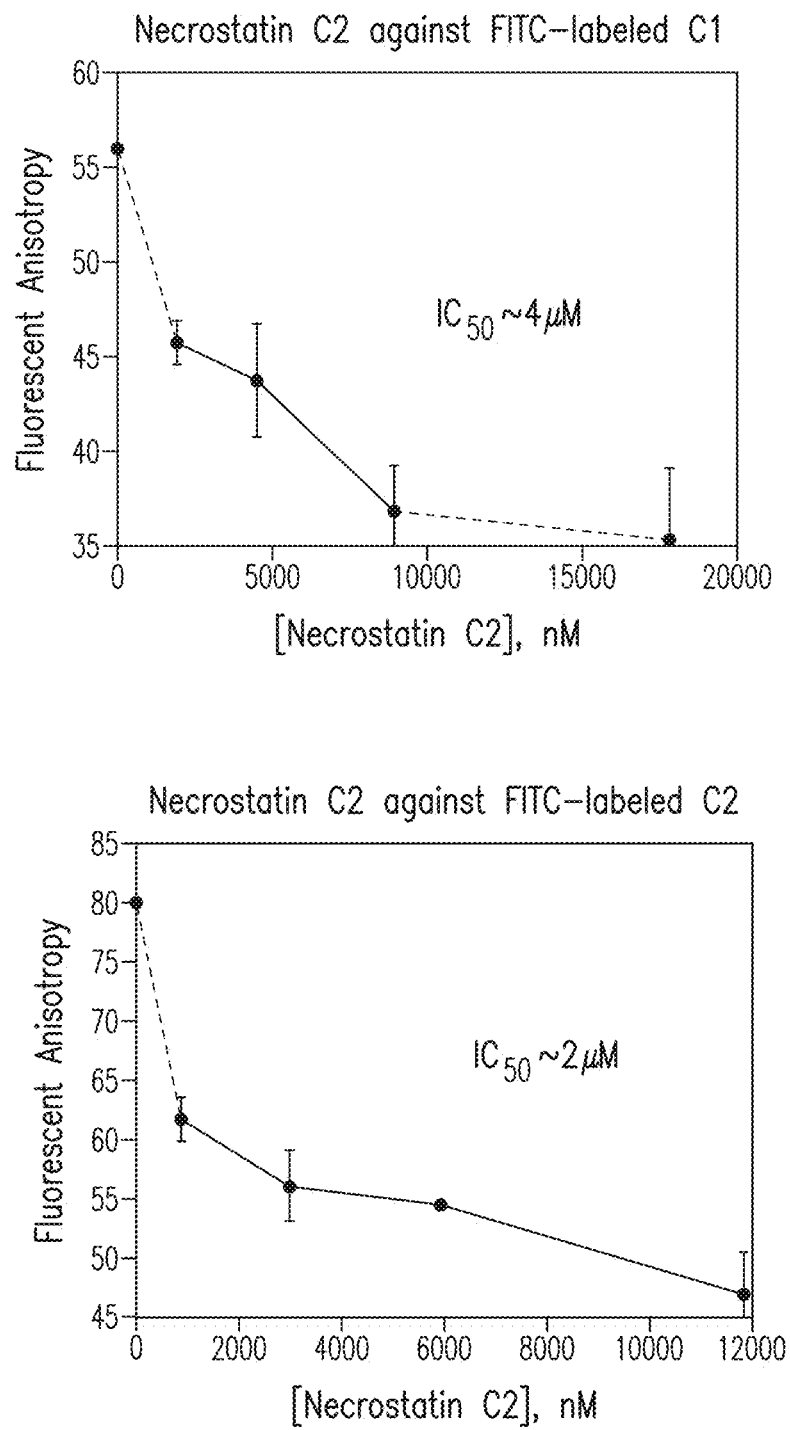
FIG. 11 shows competition between Necrostatin C1 and C2 for binding to TNFα. TNFα (1600 nM), FITC-labeled Necrostatin C1 or C2 (100 nM), and varying concentrations of unlabeled Necrostatin C2 (0-16 μM) were incubated for 1 h at 37° C. and the FA values were measured and plotted as a function of Necrostatin C2 concentration.

To confirm their binding affinity and specificity for TNFα, Necrostatin C1, C2, and the linear and monocyclic variants of Necrostatin C1 were resynthesized with a fluorescein isothiocyanate (FITC) label attached to the Dap residue (through a lysine linker) (FIG. 9), purified by HPLC, and assayed against TNFα by FA analysis. Necrostatin C1 and C2 bound to TNFα with $K_D$ values of 0.45 and 1.9 µM, respectively (FIG. 3b). These $K_D$ values are somewhat different from those derived from the single-bead FA analysis (FIG. 7), probably because of impurities present in the bead derived peptide samples and the lower-than-expected peptide concentration that made the single-bead analysis results less reliable. The linear C1 variant exhibited only weak binding to TNFα ($K_D$>10 µM), whereas the monocyclic peptide showed no significant binding affinity (FIG. 9). Bicyclo(Arg-Arg-Arg-Arg-Nal-Phe-Dap-Ser-D-Val-Pro-pTyr-His-Dap; SEQ ID NO.: 69), a control peptide arbitrarily selected from another library (unrelated to TNFα), was also tested and had no detectable binding to TNFα (FIG. 9). These results demonstrate that both the peptide sequence and the overall bicyclic structure can play a role in binding to the target protein. Presumably, the bicyclic scaffold can restrict the peptide sequence into a conformation(s) that is energetically inaccessible by the linear or monocyclic peptide. To determine whether Necrostatin C1 and C2 are specific ligands of TNFα, they were tested for binding to five other proteins of diverse structures and functions, including bovine serum albumin (BSA), a glutathione-S-transferase-PLC7 SH2 domain fusion (GST-SH2), protein phosphatase PTP1B, HIV capsid protein, and a GST-BRCT domain fusion protein. Necrostatin C1 showed weak binding to BSA ($K_D$-34 µM), but not to any of the other proteins, while Necrostatin C2 was less selective showing varying affinities to BSA, GST-SH2, and PTP1B proteins ($K_D$=3.0-37 µM; FIG. 10). Finally, Necrostatin C2 (unlabeled) inhibited the binding of FITC-labeled Necrostatin C1 and C2 to TNFα in a concentration-dependent manner ($IC_{50}$ values of ~4 and ~2 µM, respectively) (FIG. 11), suggesting that both compounds bind to the same (or overlapping) site on TNFα. It should be noted that intermediate binding affinity to serum proteins may be of therapeutic benefits, as it greatly increases the residence time of the therapeutic agent in circulation (Liu, X et al. *Curr. Top. Med. Chem.*, 2011, 11, 450-466). Because of its higher affinity and specificity for TNFα, Necrostatin C1 was selected for further biological tests.

Inhibition of TNFα-TNF Receptor Interaction by Necrostatin C1.

Figure 4:
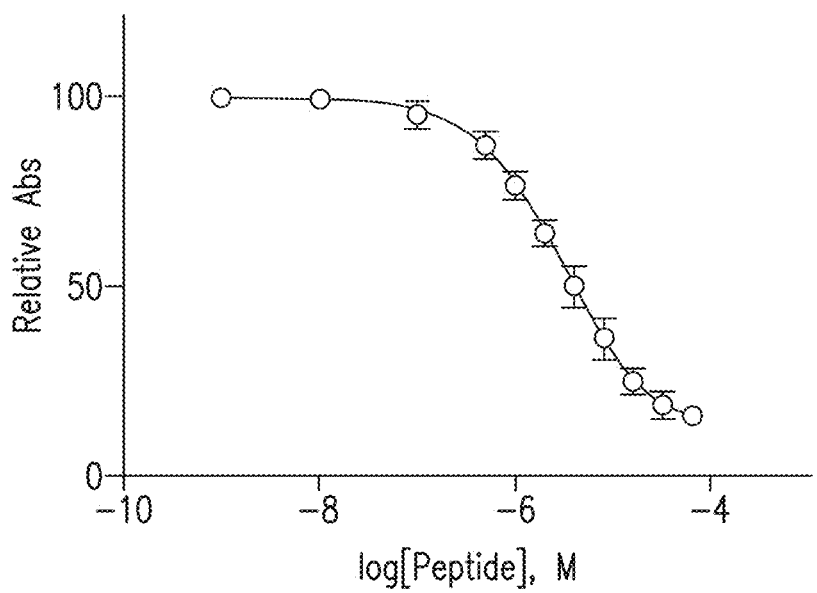
FIG. 4 shows Inhibition of TNFα-TNFR1 interaction by Necrostatin C1. The absorbance values on the y axis, which reflect the amount of TNFR1 bound to immobilized TNFα in the presence of increasing concentrations of Necrostatin C1, are relative to that in the absence of peptide inhibitor (100%).

TNFα signaling begins with the binding of the TNFα trimer to the extracellular domain of TNFR1, triggering the release of the inhibitory protein, silencer of death domains (SODD), from the intracellular domain of TNFR1 (Chen, G and Goeddel, D V. *Science*, 2002, 296, 1634-1635). To test whether Necrostatin C1 inhibits the interaction between TNFα and TNFR1, biotinylated TNFα was immobilized onto a Neutravidin-coated 96-well microtiter plate. The plate was incubated with 0.5 nM horse radish peroxidase (HRP)-conjugated TNFR1 in the presence of varying concentrations of Necrostatin C1. After washing, the amount of HRP-TNFR1 bound to each well was quantitated by ELISA using 3,3',5,5'-tetramethylbenzidine (TMB) as HRP substrate, which was converted into 3,3',5,5'-tetramethylbenzidine diimine by HRP resulting in absorbance at 450 nm (Martin, T L et al. *J. Histochem. Cytochem.*, 1984, 32, 793). Necrostatin C1 inhibited the TNFα-TNFR1 interaction in a concentration-dependent manner, with an $IC_{50}$ value of 3.1±0.3 µM (FIG. 4).

Necrostatin C1 Protects Cells from TNFα-Induced Apoptosis.

Figure 5:
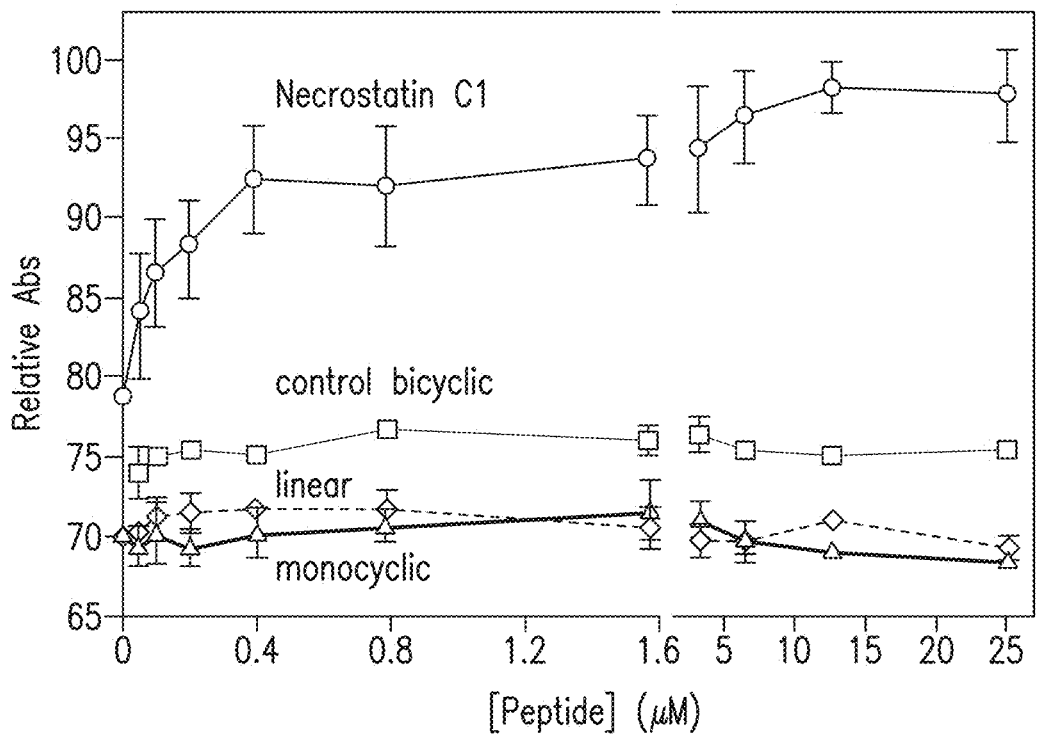
FIG. 5 shows the protection against TNFα-induced cell death by Necrostatin C1. WEHI-13VAR cells were incubated overnight at 37° C. in the presence of TNFα (0.04 ng/mL) and varying concentrations of peptide (0-25 μM), and the number of live cells was quantitated by MTT assay. The absorbance values on the y axis, which reflect the number of live cells, are relative to that of DMSO control (no TNFα, no peptide).
Figure 12:
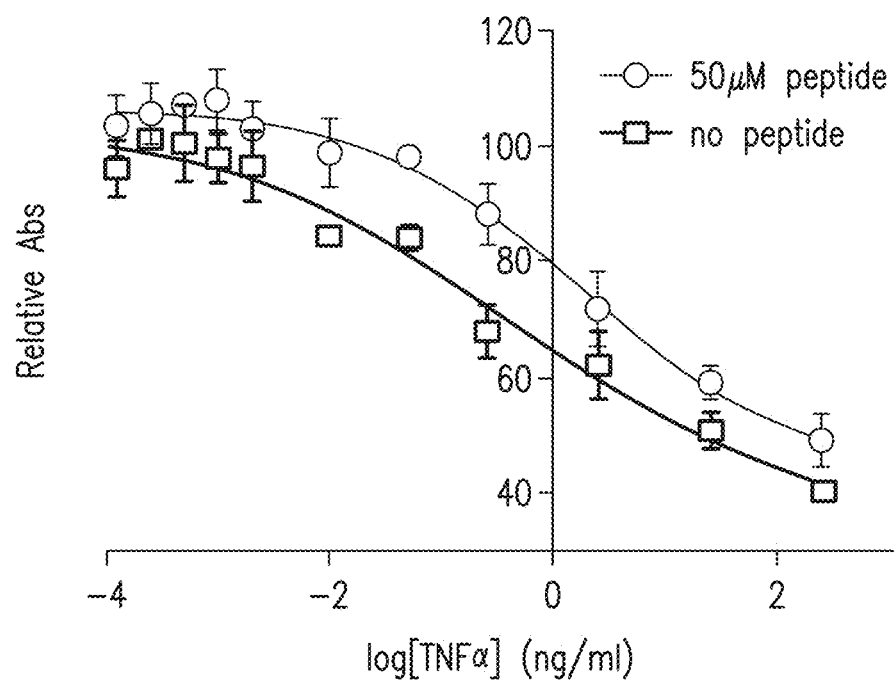
FIG. 12 shows protection of TNFα-induced cell death by Necrostatin C1. WEHI-13VAR cells were treated with increasing concentrations of TNFα (0-250 ng/mL) in the absence and presence of 50 μM Necrostatin C1. After incubation at 37° C. overnight, the number of live cells was determined by the MTT assay and plotted as a function of TNFα concentration. All y axis values are relative to that in the absence of TNFα or Necrostatin C1 (100%).

The ability of Necrostatin C1 to protect cells against TNFα-induced cell death was tested with cultured WEHI-13VAR fibroblasts, which are highly sensitive to TNFα in the presence of actinomycin-D ($LD_{50}$ range: 0.005-0.065 ng/mL) (Khabar, K S et al. *Immunol. Lett.*, 1995, 46, 107-110). WEHI-13VAR cells were treated with a fixed concentration of TNFα (0.04 ng/ml) and varying concentrations of Necrostatin C1 (0-25 µM) and the fraction of live cells was quantitated by the 3-(4,5-dimethylthiazol-2-yl)-2,5-diphenyltetrazolium bromide (MTT) assay. Necrostatin C1 protected the cells from TNFα-induced cell death in a concentration-dependent manner, whereas the corresponding monocyclic and linear peptides did not (FIG. 5). The control bicyclic peptide, bicycle(Arg-Arg-Arg-Arg-Nal-Phe-Dap-Ser-D-Val-Pro-pTyr-His-Dap; SEQ ID NO.: 70), which does not bind TNFα, had no protective effect. The MTT assay was also conducted at a fixed concentration of Nercostatin C1 (50 μM) but varying concentrations of TNFα (0-250 ng/mL). Under the assay conditions, TNFα exhibited an $LD_{50}$ value of 0.46 ng/mL in the absence of TNFα inhibitor; in the presence of 50 μM Necrostatin C1, the $LD_{50}$ value was shifted to 1.8 ng/mL (FIG. 12). Taken together, this data suggest that Necrostatin C1 binds to TNFα at or near the TNFα-TNFR1 interface.

Conclusions.

In conclusion, disclosed herein is a methodology for chemical synthesis and screening of large combinatorial libraries of bicyclic peptides against macromolecular targets of biomedical significance. Compared to the previously reported methods for bicyclic peptide library synthesis (Sun, Y et al. *Org. Lett.,* 2001, 3, 1681-1684; Virta, P and Lonnberg, H J. *J. Org. Chem.,* 2003, 68, 8534; Hennis, C et al. *Nat. Chem. Biol.,* 2009, 5, 502-507; Chen, S et al. *Chem Bio Chem.,* 2012, 13, 1032-1038; Sako, Y et al. *J. Am. Chem. Soc.,* 2008, 130, 7232-7234; Timmerman, P et al. *J. Biol. Chem.,* 2009, 284, 34126-34134), most of which involve ribosomal peptide synthesis followed by chemical cyclization, the disclosed methods have the advantage that it allows the incorporation of any unnatural amino acid or non-peptidic building blocks, resulting in greater structural diversity and improved metabolic stability of the cyclic peptides. In addition, chemical synthesis allows for the use of orthogonal protecting groups, which in turn permits more "forcing" reaction conditions to drive the desired cyclization reaction to completion and can prevent any undesired cyclization reaction from occurring. It was also demonstrated that bicyclic peptides, such as the compounds disclosed herein, containing a planar scaffold are capable of binding to flat protein surfaces such as PPI interfaces. With a $K_D$ value of 0.45 μM, Necrostatin C1 is the most potent non-protein TNFα inhibitor reported to date. The bicyclic library methodology described here should be applicable to other proteins and nucleic acid targets.

Example 2

Bicyclic Peptide Ligands Against K-Ras

Approximately 300 mg of the bicyclic library was screened against biotinylated or fluorescently labeled K-Ras in 4 rounds, as described for TNFα. This screening produced 130 initial hits after the third round (screening against Texas red-labeled K-Ras). FA analysis at a single concentration of peptide (~100 nM) and K-Ras protein (5 mM) showed that 8 hits produced FA increases of ≥25%. These 8 hits were subjected to full binding curve analysis using 50 nM peptide and 0-20 μM K-Ras. Six showed significant binding in the solution phase and their corresponding beads were sequenced by PED-MS. Complete sequences were obtained for hits #38, #28, #13, #82, and #105 (Table 4). Resynthesized hit #13 showed no significant binding while resynthesized 28 showed weak binding ($K_D$>5 μM).

TABLE 4

Binding affinities of hits from library.

| Hit No. | Sequence[a] | SEQ ID NO. | Binding affinity from single-bead analysis ($K_D$, μM) | $K_D$ of resynthesized peptide (μM) |
|---|---|---|---|---|
| 13 | Gln-Gln-val-Asp-Lys-Fpa-phe-nal-ala-Gly-Dap | 94 | 5.1 ± 1.8 NA | NA |
| 28 | Tyr-nal-leu-Lys-ala-Gln-Ala-Gly-Ser-Dap | 95 | 3.2 ± 1.6 | 6.8 ± 4.5 |
| 38 | Trp-phe-Asp-Lys-phe-asn-His-Dap | 71 | 2.6 ± 0.6 | 0.49 ± 0.08 |
| 82 | nal-Ser-Gln-nal-Phg-Lys-phe-Arg-val-Arg-Dap | 72 | 3.3 ± 1.1 | 2.1 ± 0.9 |
| 105A | Arg-Arg-nal-Arg-Fpa-Lys-phe-glu-Gly-Dap | 73 | ND | 1.4 ± 0.4 |
| 105B | Orn-Arg-nal-Arg-Fpa-Lys-phe-glu-Gly-Dap | 74 | 0.052 ± 0.020 | 2.6 ± 1.3 |

[a]The three-letter codes for L-amino acids have the first letter capitalized, whereas those of D- amino acids have all lower-case letters.
NA, no significant binding activity;
ND, not determined.

Figure 22A:
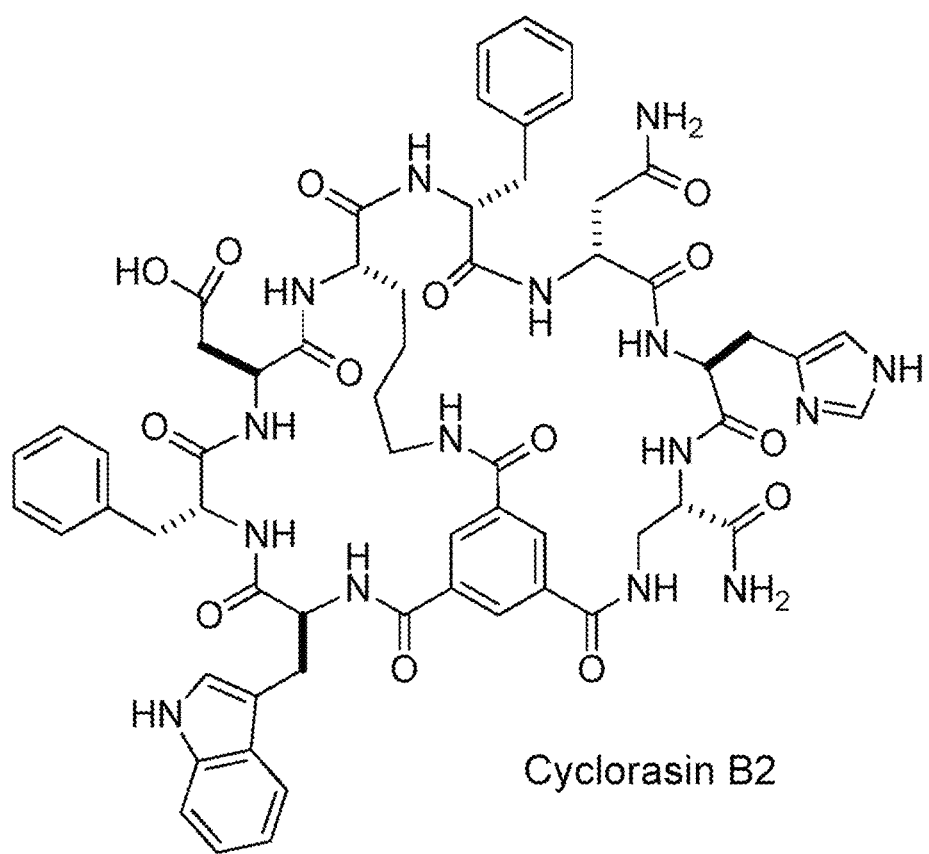
FIG. 22a displays structures of cyclorasin B2 and B3.
Figure 22A:
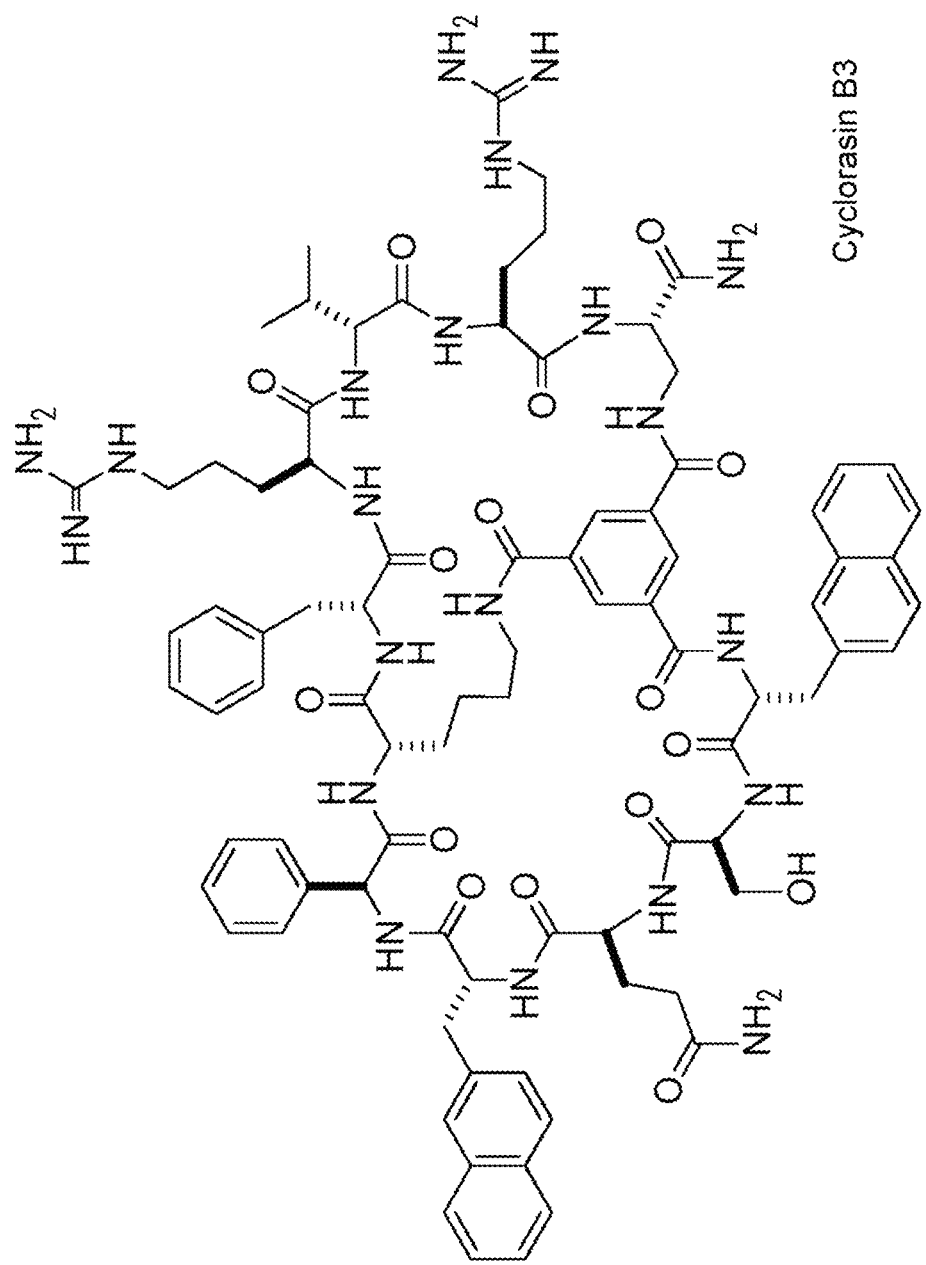

Bicyclic peptides 13, 28, 38, 82, and 105 were resynthesized, labeled with fluorescein isothiocyanate (FITC) at an added C-terminal Lys (FIG. 22a and Scheme 1), and analyzed for binding to K-Ras by FA.
Scheme 1
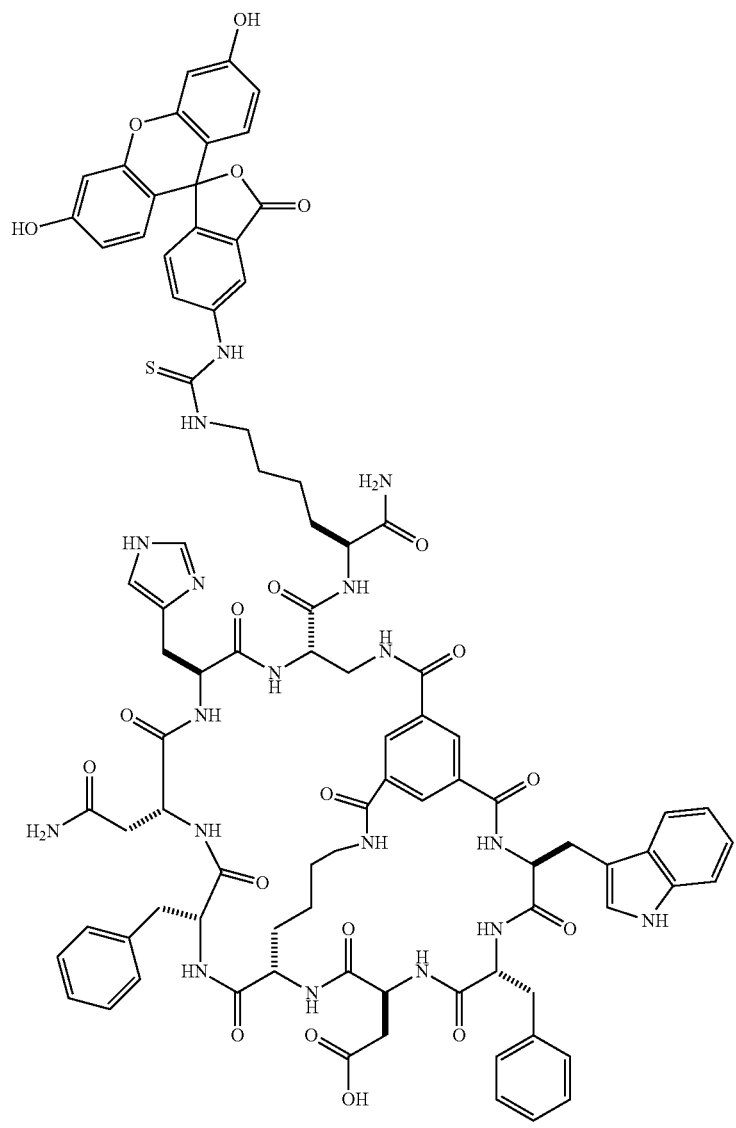
FITCF-cyclorasin B2

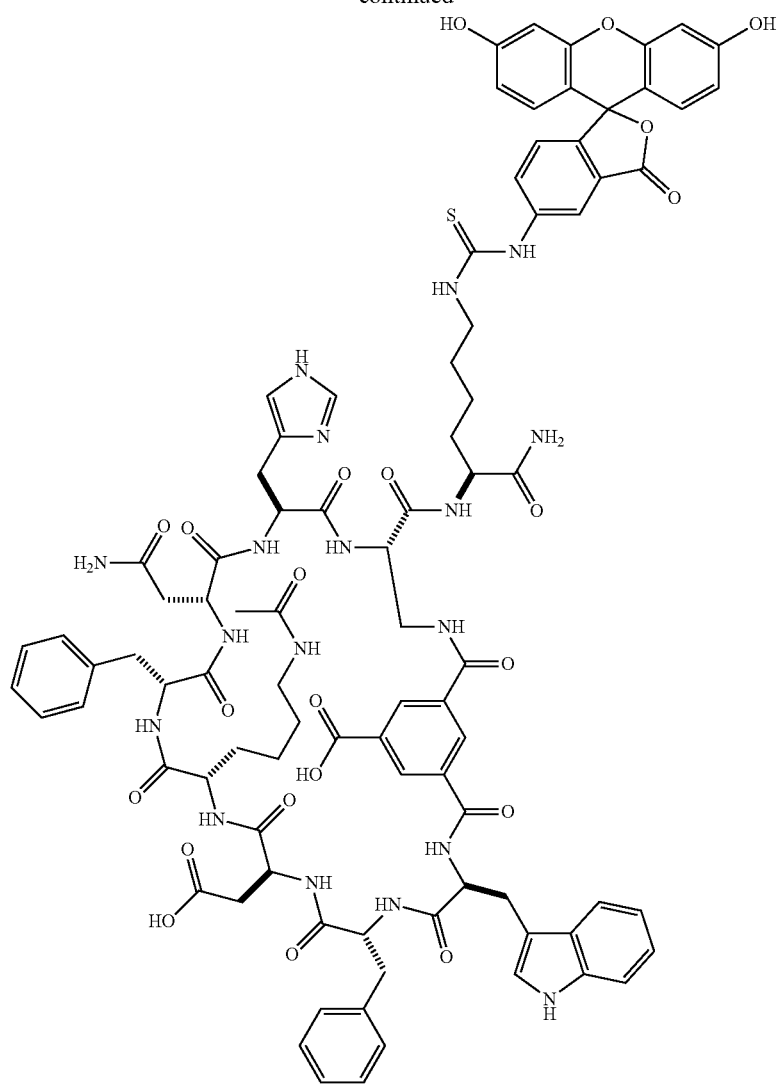
FITC-monocyclic analog

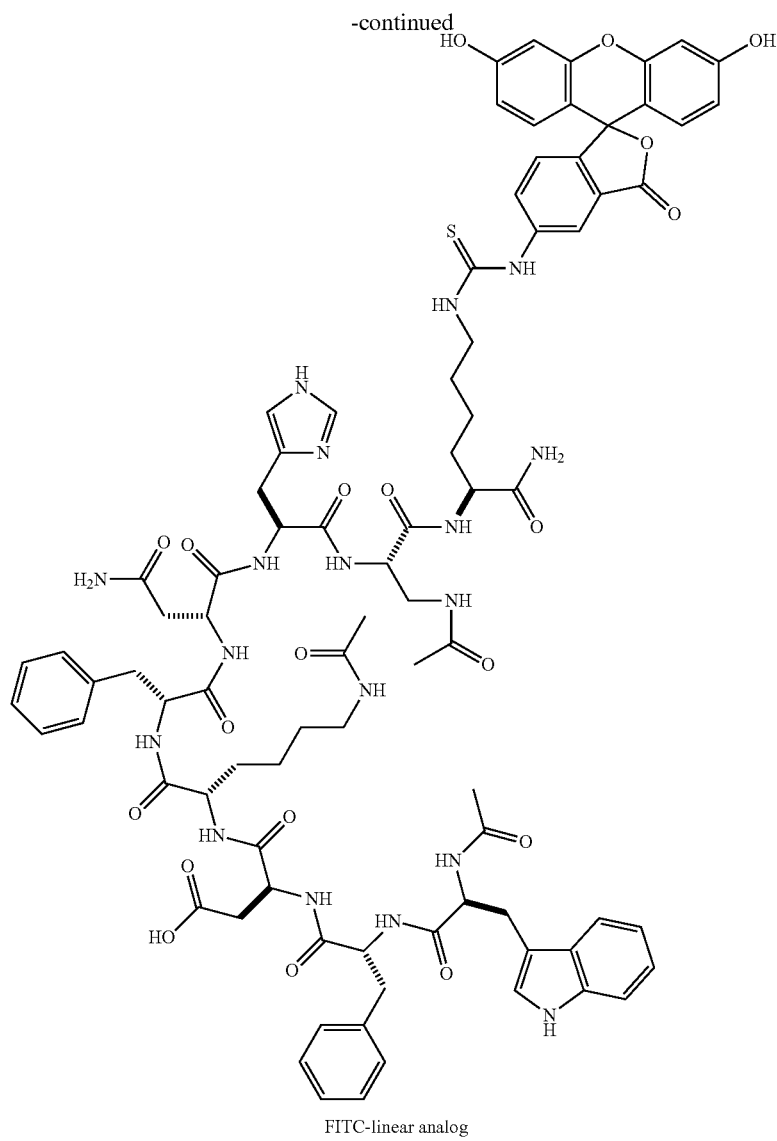

FITC-linear analog

Peptides 28, 38, 82 and 105 bound to recombinant K-Ras with $K_D$ values of 6.3, 0.49, 2.1, and 2.6 μM (FIG. 22b and Table 4) and were named as "cyclorasin B1-4" (for cyclic ras inhibitor bicyclic), respectively. Peptide 13 did not show significant binding to K-Ras. The discrepancy between the binding affinities derived from single-bead analysis and those determined with resynthesized and purified peptides may be caused by impurities present in the peptide samples released from the single beads (e.g., truncated peptides), which may interfere with the binding of bicyclic peptide with K-Ras. Cyclorasin B2-4 were selected for further characterization because of their relatively high potencies.

The ability of cyclorasin B2-4 to block Ras-effector interactions was first evaluated by a qualitative bead-binding assay (Wu, et al., *Med. Chem. Commun.* 2013, 4, 378-382). Briefly, GST-Raf was immobilized on glutathione beads and incubated with Texas red-labeled Ras protein; binding of the Ras protein to the immobilized Raf rendered the beads intensely red (FIG. 23a). However, the Ras-Raf interaction was completely abolished in the presence of 10 μM cyclorasin B3 or B4 (FIG. 23b), but not cyclorasin B2. The potency for inhibition of the Ras-Raf interaction was next determined by a homogeneous time resolved fluorescence (HTRF) assay (Leyris, J. P. et al. *Anal. Biochem.* 2011, 408, 253-262), giving an $IC_{50}$ value of ~1.4 μM for cyclorasin B3 (FIG. 23c). Cyclorasin B2 again showed no inhibition. The HTRF assay failed for cyclorasin B4 due to aggregation and precipitation of B4 at higher concentrations. The ability of cyclorasin B2-4 to compete with the Ras-binding domain (RBD) of Raf (GST-Raf RBD) and compound 12, the monocyclic K-Ras inhibitor we previously reported, was examined for binding to K-Ras using an FA-based competition assay. Addition of GST-Raf RBD (FIG. 23d) or compound 12 (FIG. 23e) inhibited the binding of FITC-labeled cyclorasin B3 to K-Ras in a concentration-dependent manner. Compound 12 also abolished the binding of cyclorasin B4 but not B2 to K-Ras. These results suggest that like compound 12, cyclorasin B3 and B4 bind to a site(s) at or near the Ras-Raf interface, whereas cyclorasin B2 binds to a site different from the Ras-Raf interface.

Figure 22B:
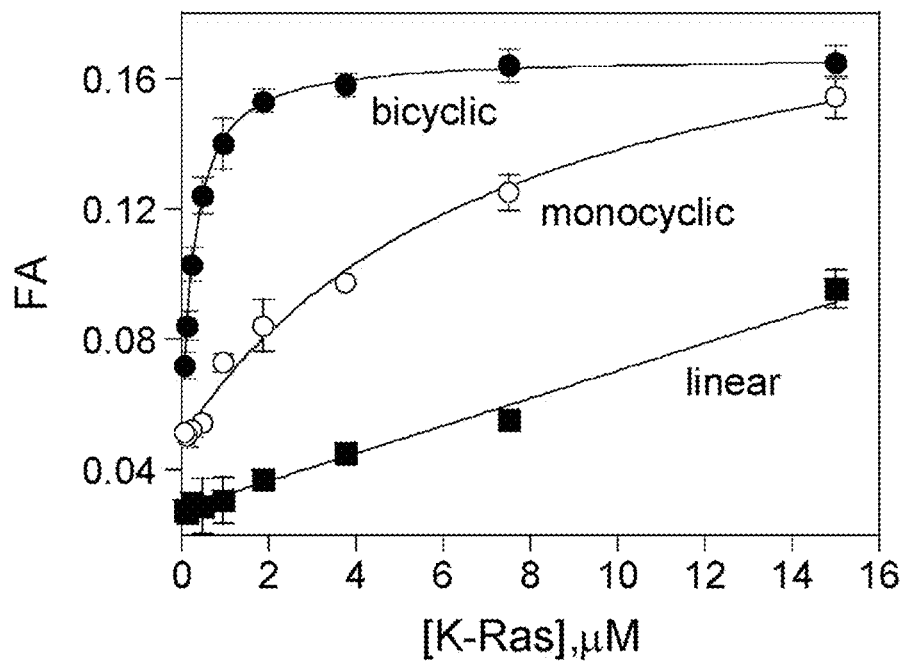
FIG. 22b displays a FA analysis of K-Ras (mixture of Ras-GTP and Ras-GDP) binding by FITC-labeled cyclorasin B2 and its monocyclic and linear counterparts.
Figure 22C:
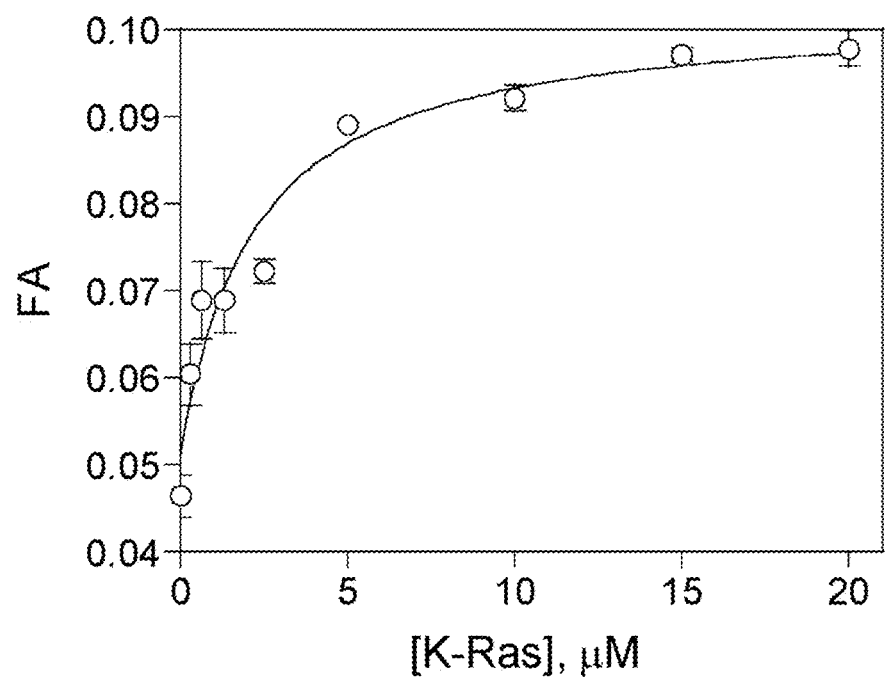
FIG. 22c displays a FA analysis of K-Ras binding by cyclorasin B3.
Figure 22D:
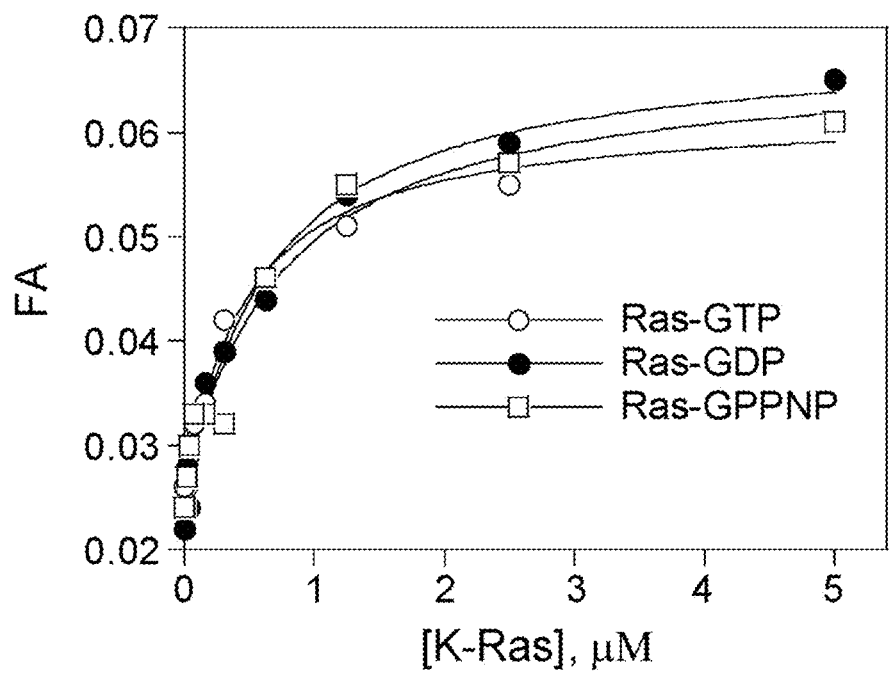
FIG. 22d is a comparison of FITC-labeled cyclorasin B2 binding to Ras-GTP, Ras-GDP, and Ras-GPPNP.
Figure 22E:
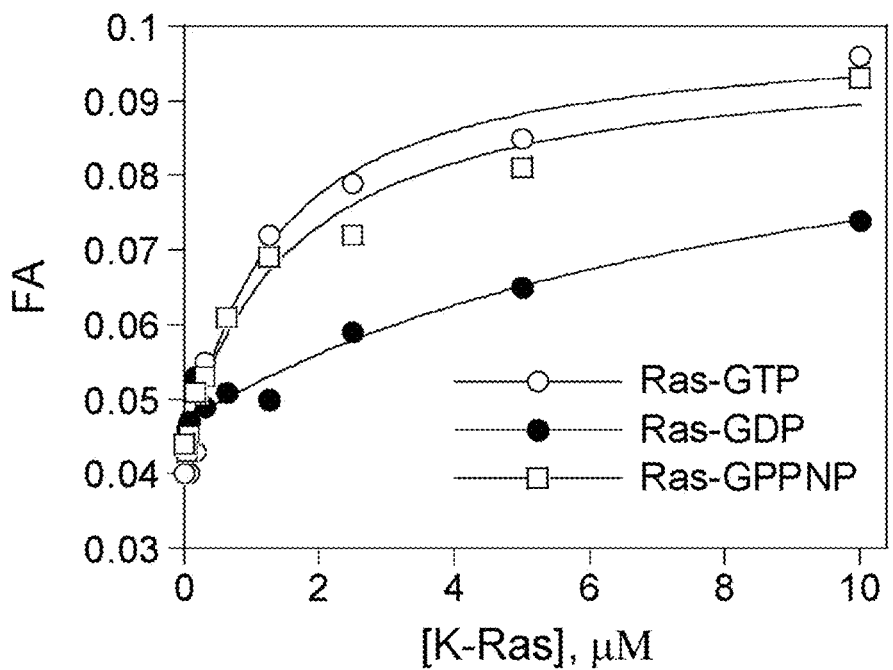
FIG. 22e is a comparison of FITC-labeled cyclorasin B3 binding to Ras-GTP, Ras-GDP, and Ras-GPPNP.

To assess the specificity of cyclorasin B2-4 for K-Ras, the ability of cyclorasin B2-4 to self-compete for binding to K-Ras and to bind other proteins was examined. Addition of unlabeled cyclorasin B2 inhibited the binding of FITC-labeled B2 to K-Ras in a concentration-dependent manner. Likewise, unlabeled cyclorasin B4 inhibited the binding of FITC-labeled B4 to K-Ras. These results further support the notion that cyclorasin B2-4 each bind to a specific site on K-Ras. To determine whether the bicyclic structure is important for binding to K-Ras, the monocyclic and linear counterparts of cyclorasin B2 (FIG. S3) were synthesized and their binding affinity for K-Ras was measured. The monocyclic and linear peptides bound to K-Ras with $K_D$ values of 7.4 and 58 μM, or 15- and 120-fold lower affinity than cyclorasin B2, respectively (FIG. 22b). Therefore, both the bicyclic structure and the amino acid sequence are required for high-affinity binding to K-Ras. To test whether the cyclic peptides have any selectivity for the signaling-active form of Ras, K-Ras was specifically loaded with GTP, GDP, or GPPNP (a GTP analog). Cyclorasin B2 bound to all three Ras forms with essentially the same affinity ($K_D$=0.49, 0.64, and 0.76 μM, respectively) (FIG. 22d). In contrast, cyclorasin B3 bound to Ras-GTP and Ras-GPPNP with approximately 8-fold higher affinity than Ras-GDP ($K_D$ values of 1.2, 1.6, and 9.3 μM, respectively) (FIG. 22e). Finally cyclorasin B2 and B3 were tested for binding to five arbitrarily selected proteins, including bovine serum albumin (BSA), protein-tyrosine phosphatase 1B (PTP1B), GST-SHD SH2 domain fusion protein, maltose-binding protein-XIAP BIR3 domain fusion (MBP-BIR3), and GST-FKBP12 fusion protein. Cyclorasin B2 is a selective K-Ras ligand, showing only weak binding to BSA, GST-SHD SH2, and MBP-BIR3 proteins ($K_D$=23-57 μM, which are 47-120-fold higher than that of K-Ras) but no binding to PTP1B or GST-FKBP12 (FIG. S5). Cyclorasin B3 is somewhat less selective than cyclorasin B2 and bound to MBP-BIR3 and BSA with $K_D$ values of 16 and 17 μM, respectively, and very weakly to PTP1B, GST-SHD SH2, and GST-FKBP12.

Cyclorasin B2-B4 were tested for inhibition of cell proliferation by the MTT assay. None of the compounds showed significant effect on the proliferation of cultured cancer cells up to 50 μM concentration, due to poor membrane permeability of the cyclic peptides (as determined by confocal microscopy of cells treated with FITC-labeled peptides). When attached to an oleic acid group to improve its membrane permeability (Scheme II), cyclorasin B3 exhibited modest anti-proliferative activity against H358 lung cancer cells (FIG. 23f).

Scheme II

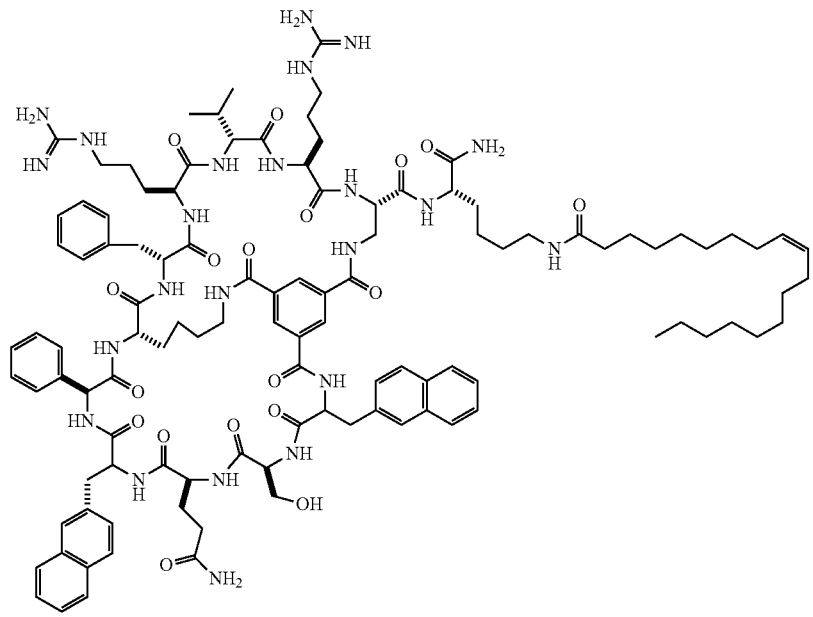

cyclorasin B3 conjugated to an oleic acid

Conjugation of cyclorasin B2 to a fatty acid or cell-penetrating peptide ($Arg_{11}$) failed to confer any cellular activity.

Example 3

Synthesis of Diallyl Nitrilotriacetic Acid

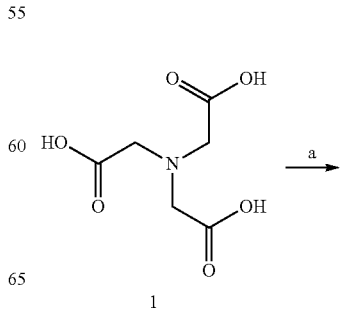

1

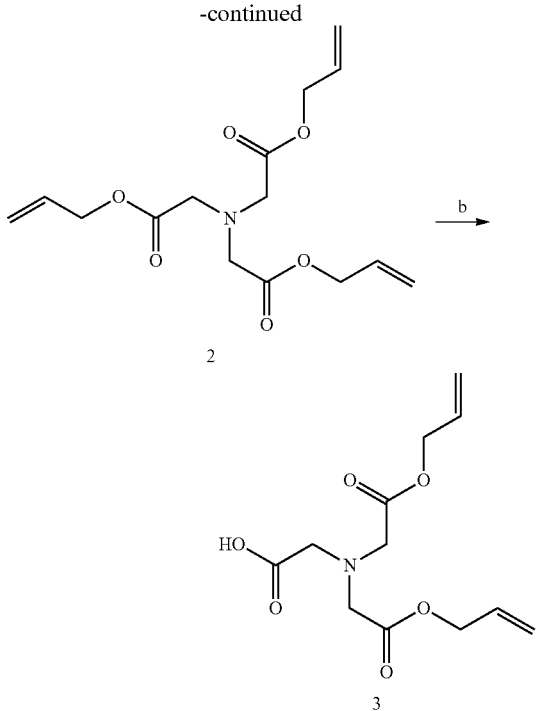

Synthesis of [2].

To a flame dried 25 mL round bottom flask was added 1 (nitrilotriacetic acid, 1.00 g, 5.24 mmol, 1.0 eq.) and allyl alcohol (10 mL). Thionyl chloride (2 mL, 26.18 mmol, 5.0 eq.) was added dropwise at 0° C., followed by DMF (40 µL, 0.524, 0.1 eq.). The reaction was allowed to warm to room temperature before being heated at 75° C. overnight. The reaction was concentrated under reduced pressure, and water (10 mL) and DCM (10 mL) were added. The organic layer was washed with saturated sodium carbonate solution (1×), and then extracted with DCM (3×). The combined organic layers were dried (MgSO₄), filtered, and concentrated to yield 2 quantitatively.

Synthesis of [3].

To crude residue of 2 was added THF (10 mL), KOH (0.264 g, 4.7 mmol, 0.9 eq.), and allyl alcohol (6 mL). The mixture was allowed to stir for 1 h at room temperature, and then concentrated under reduced pressure. It was then extracted with isopropyl alcohol (3×), and the extracts were combined, filtered, and concentrated to yield a mixture of 2 and 3 (~60% 3 by NMR).

Example 4

Peptide Library Design

Figure 13:
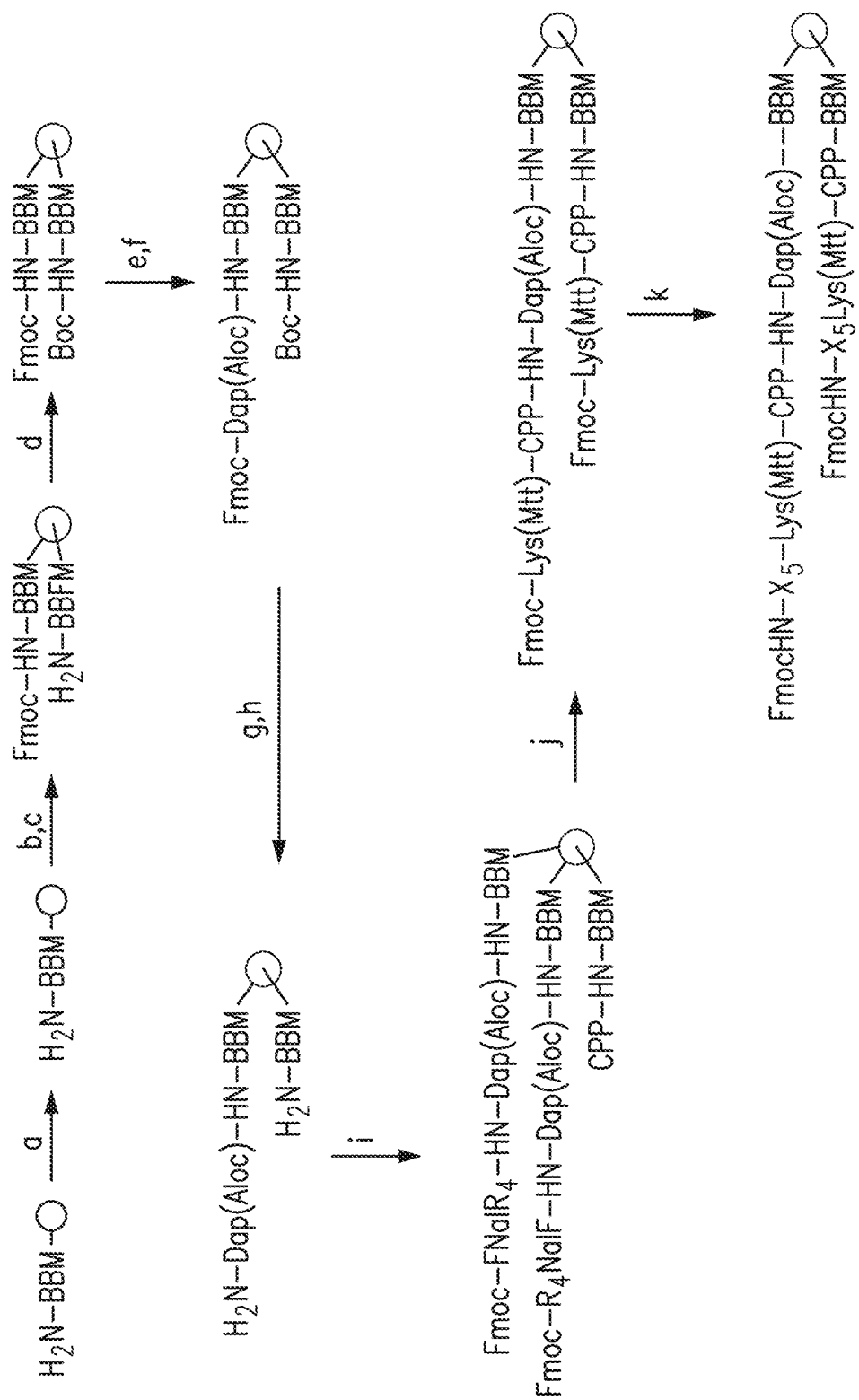
FIG. 13 displays a schematic of the synthesis of peptide library I. Reagents and Conditions: (a) Standard Fmoc/HBTU chemistry; (b) Soak in water; (c) 0.5 eq. of Fmoc-OSu; (d) Boc anhydride, DMF; (e) 20% piperidine; (f) Fmoc-Dap(Alloc)-OH, HATU; (g) 95:5 TFA/$H_2O$; (h) 20% piperidine; (i) Split into 2 equal portions, then standard Fmoc/HATU chemistry; CPP=cell penetrating peptide (j) Pooled the beads, then Fmoc-Lys(Mtt)-OH, HATU; (k) Split and pool synthesis.

A bicyclic peptide library (library I) was designed in the form of Fmoc-NH-X₅-Lys(Mtt)-(Membrane transporter)-Dap(Aloc)-BBM-Resin (where B is β-Alanine) utilizing a previously published strategy (FIG. 13). The C-terminal ring contains a membrane transporter sequence in two directions (Phe-Nal-Arg-Arg-Arg-Arg (SEQ ID NO: 96) or Arg-Arg-Arg-Arg-Nal-Phe (SEQ ID NO: 97)) while the N-terminal ring contains the random amino acids. To facilitate the attachment of a small molecule to the library through click chemistry, propargyl glycine (Pra) was incorporated in the random region. The amount of Pra on each bead was reduced by 10-fold by co-coupling Fmoc-Pra-OH with an inert amino acid (Fmoc-Lys(Ac)-OH) at a ratio of 10% Pra to 90% Lys(Ac). The Lys(Ac) residue conveniently serves as the encoder for sequencing after the Pra residue was modified by click chemistry. At each random position, 20% of the library was separated and coupled with Pra/Lys(Ac). The remaining 80% of the library was split equally into 25 vessels and coupled with an amino acid from the set of 25 amino acids, which includes 10 proteinogenic amino acid (Ala, Asp, Gly, His, Ile, Gln, Arg, Ser, Trp, Tyr), 9 D-amino acids (ala, glu, phe, lys, leu, asn, pro, thr, val), and 6 unnatural amino acids (L-Abu (replaced Cys), L-Nle (replaced Met), L-Phg, L-Fpa, D-Nal, L-Orn) (FIG. 14).

The library was synthesized on 90 µm TentaGel resin, starting with the addition of the BBM linker using standard Fmoc/HBTU chemistry. Spatial segregation of the beads into two layers was achieved by soaking the beads in water overnight, following by treating with 0.5 eq. of Fmoc-OSu in 1:1 (v/v) CH₂Cl₂/Et₂O. The remaining (~50%)N-terminal amines in the bead interior were capped by Boc anhydride. Subsequent removal of the Fmoc group in the outer layer, following by coupling with Fmoc-Dap(Aloc)-OH ensured only the outer layer can undergo bi-cyclization. After the removal of the Boc and Fmoc groups, the beads were split into two equal portions and the membrane transporter sequence was coupled in two opposite directions (Phe-Nal-Arg-Arg-Arg-Arg (SEQ ID NO: 96) or Arg-Arg-Arg-Arg-Nal-Phe (SEQ ID NO: 97)). The beads were pooled and coupled with Fmoc-Lys(Mtt)-OH. At each random position, 20% of the beads were coupled with 9:1 Fmoc-Lys(Ac)-OH/Fmoc-Pra-OH while the remaining 80% were split and coupled with one of the 25 amino acids.

Figure 15:
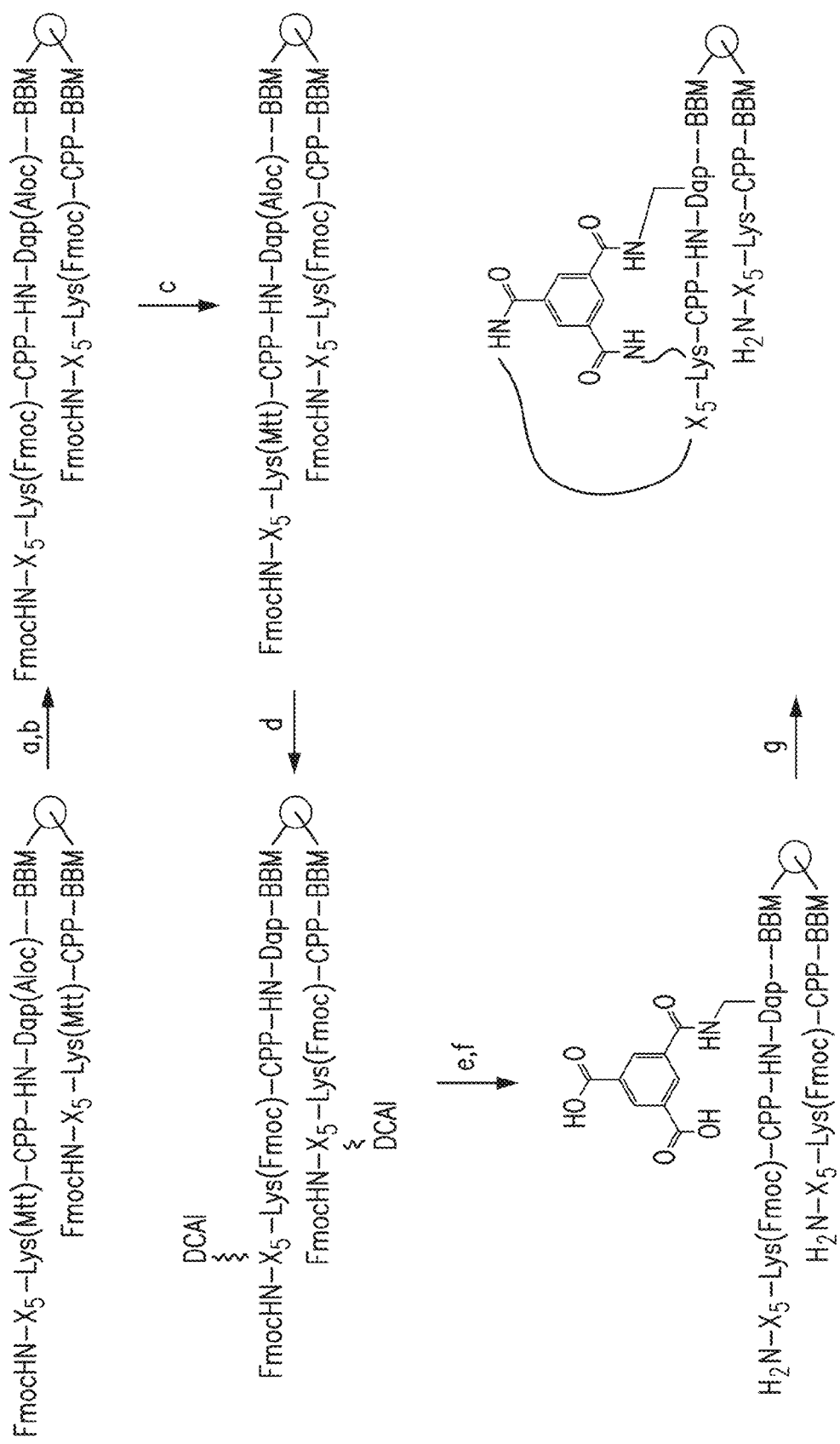
FIG. 15 displays a schematic of the preparation of the bicyclic peptide library for screening. Reagents and Conditions: (a) 2% TFA in DCM; (b) Fmoc-OSu; (c)$Pd(PPh_3)_4$; (d) Click Chemistry: DCAI-$N_3$, Cu(I); (e) Trimesic acid, HATU; (f) 2% DBU in DMF; (g) pyBOP, HOBt.

To facilitate the incorporation of small molecule and bi-cyclization, the Mtt protecting group was removed by 2% TFA in DCM, and the exposed Lys side chain was protected by treatment with Fmoc-OSu. After removal of the Aloc group on the side chain of Dap, the beads were treated with the appropriate azide (80-100 mM), 25 mM CuSO₄ and 25 mM ascorbic acid in 8:1:1 DMF/H₂O/t-butyl alcohol overnight (click chemistry). After washing to remove the click chemistry reagents, trimesic acid was coupled to the side chain of Dap using HATU as coupling reagent. Removal of the Fmoc groups with piperidine and treatment with pyBOP/HOBt/NMM afforded the bicyclic peptides containing the small-molecule "head group" on the Pra residues (FIG. 15).

Selection and Synthesis of Small Molecule Probe

Figure 16:
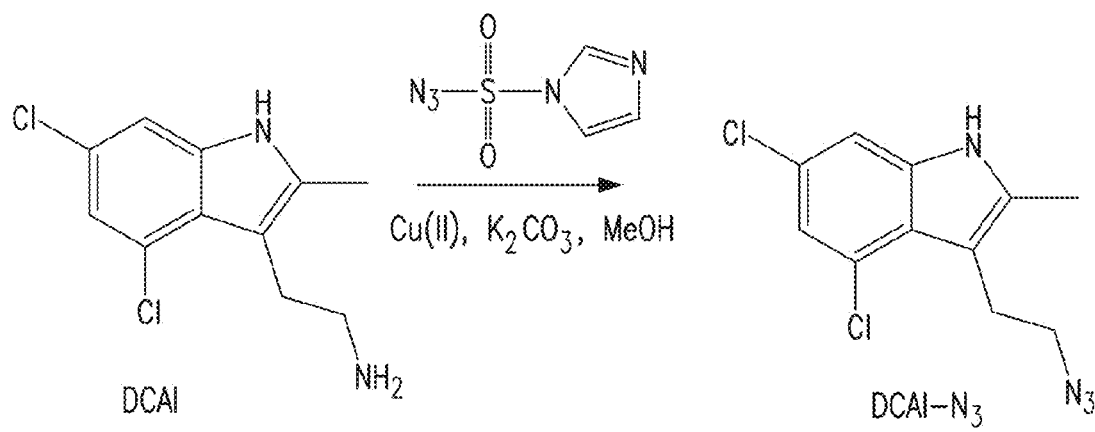
FIG. 16 displays a schematic of the synthesis of DCAI-N₃.

Several small molecules have been reported to bind to K-Ras with low affinity. Among them, 4,6-dichloro-2-methyl-3-aminoethyl-indole (DCAI) is attractive due to its low molecular weight, relatively good binding affinity to K-Ras (1.1 mM) and commercial availability. The co-crystal structure of DCAI with K-Ras revealed that the indole portion binds to a pocket on the surface of K-Ras while the alkyl amine only has minimal interaction with the protein. This provides a convenient position for attachment to bicyclic peptides through first conversion of the amine to azide and subsequent click chemistry with the alkyne group of Pra residues. DCAI was converted to the corresponding azide using imidazole-1-sulfonyl azide hydrochloride as the diazo transfer reagent (FIG. 16).

Screening Strategy and Results

GST-tagged K-Ras G12V protein was purified and labeled with biotin. A typical screening reaction involved incubating 100 mg of the library resin (~300,000 beads) with the biotinylated K-Ras overnight. After washing, the beads were be treated with streptavidin-alkaline phosphatase (SA-AP), followed by 5-Bromo-4-chloro-3-indolyl phosphate (BCIP). Binding of K-Ras to a bed recruits SA-AP to the beads (through binding to biotin by streptavidin). After dephosphorylation by alkaline phosphatase, the indolyl product dimerizes in air to form a turquoise color on positive beads. The colored beads were selected under a microscope and subjected to sequencing by PED/MS.

Screening 100 mg of the DCAI-labeled bicyclic library against biotinylated K-Ras (300 nM) produced 21 hits, resulting in 13 full sequences after PED/MS analysis (FIG. 20). The sequences revealed several trends. The transporter sequence is preferred in the forward orientation (Phe-Nal-Arg-Arg-Arg-Arg (SEQ ID NO: 96)), with 12 out of the 13 hits containing this motif. The Pra/Lys(Ac) (Z) residue is preferred at the $X_1$ or $X_3$ position, with all sequences containing Z at either $X_1$, $X_3$ or both psotions (FIG. 20). When a sequence contains two Z residues, it is most likely that one of them is Pra while the other is Lys(Ac).

Binding Analysis of Selected Peptide by Fluorescence Anisotropy

To confirm the screening results, four hit sequences (peptides A2, A8, B5 and B8; hereafter named as peptides 1-4) were selected for resynthesis and tested for binding to K-Ras in solution by fluorescence anisotropy. The peptides were synthesized on Rink Amide resin, cleaved, deprotected, and purified by reversed-phase HPLC. Each peptide contains a Lys outside of the bicyclic rings to serve as the point of labeling with an amine-reactive fluorescent dye (FAM-NHS or FITC). Peptides 2 and 4 showed fairly potent binding to K-Ras, with $K_D$ values of 5.1 μM and 9 μM, respectively. Peptide 3 binds to K-Ras with weak affinity (20 μM), while peptide 1 does not bind to K-Ras (Table 5).

TABLE 5

Binding Affinities of peptides 1-4 against K-Ras.

| Peptide | Sequence | SEQ ID NO. | $K_D$ (μM) |
|---|---|---|---|
| 1 | bicyclo(Arg-Asp-Phg-Pra-d-Asn-K-FNalR$_4$-Dap)-K | 75 | NB |
| 2 | bicyclo(Phg-Arg-d-Asn-Pra-Ile-K-FNalR$_4$-Dap)-K | 76 | 5.1 |
| 3 | bicyclo(Pra-Ser-Phg-Lys(Ac)-Lys(Ac)-K-FNalR$_4$-Dap)-K | 77 | 20 |
| 4 | bicyclo(Pra-Arg-d-Val-Asp-Ala-K-FNalR$_4$-Dap)-K | 78 | 9 |

NB = no binding

Figure 17:
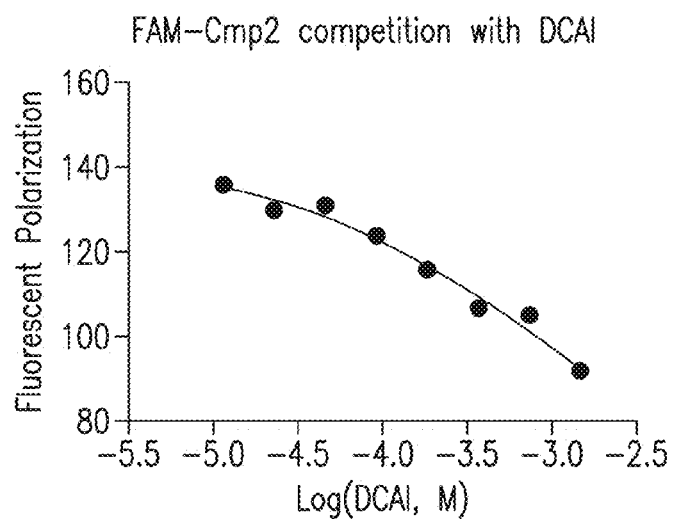
FIG. 17 displays the results of a competition assay between FAM-labeled peptide 2 and DCAI.

To test whether peptide 2 and DCAI bind to similar sites, a competition experiment was performed in which the binding of FITC-labeled peptide 2 to K-Ras was assayed in the presence of increasing concentrations of DCAI (FIG. 17). DCAI inhibited the binding of peptide 2 with an $IC_{50}$ value of 1.4 mM, indicating that peptide 2 occupies the same binding pocket that recognizes DCAI.

Optimization of Peptide 2

To test whether ring expansion would improve the binding affinity, four peptides (peptide 5-8) were synthesized by inserting one to three Ala into the Pra-containing ring. It was found that the addition of only one Ala to either side of the Pra-containing sequence (peptide 5 and 6) did not significantly improve the binding ($K_D$ of 6.4 μM and 5.6 μM respectively). However, adding one Ala residue to both sides of the motif (peptide 7) improved the binding affinity to 1.8 μM while the addition of three Ala residues (two to the N-terminus and one to the C-terminus of Pra motife) improved the binding affinity to 1.1 μM (Table 6).

TABLE 6

Binding affinities of peptide 5-8 against K-Ras

| Peptide | Sequence | SEQ ID NO. | $K_D$ (μM) |
|---|---|---|---|
| 5 | bicyclo(Ala-Phg-Arg-d-Asn-Pra-Ile-K-FNalR$_4$-Dap)-K | 79 | 6.4 |
| 6 | bicyclo(Phg-Arg-d-Asn-Pra-Ile-Ala-K-FNalR$_4$-Dap)-K | 80 | 5.6 |
| 7 | bicyclo(Ala-Phg-Arg-d-Asn-Pra-Ile-Ala-K-FNalR$_4$-Dap)-K | 81 | 1.8 |
| 8 | bicyclo(Ala-Ala-Phg-Arg-d-Asn-Pra-Ile-Ala-K-FNalR$_4$-Dap)-K | 82 | 1.1 |

It was next tested whether replacement of the added Ala residues by other amino acids might further improve the potency of the peptide. A focused bicyclic library (library II) based on the sequence of peptide 2 was synthesized in the form of: bicyclo($X^1$-$X^2$-Phg-Arg-d-Asn-Pra-Ile-$X^3$-K-FNalR$_4$-Dap)-BBM-TentaGel bicyclo($X^1$-$X^2$-Phg-Arg-d-Asn-Pra-Ile-$X^3$-K-FNalR$_4$-Dap)-BBM-TentaGel (SEQ ID NO: 98, underlined portion), where X is any of the 25 amino acids used for library I. Screening 50 mg of library 2 against 100 nM of biotinylated K-Ras produced 25 hits, which gave 19 full sequences after PED/MS. The results showed that small hydrophobic amino acids (Ala, d-Ala) are preferred at $X^1$ position while $X^2$ and $X^3$ positions had little selectivity (FIG. 21).

Nine of the hit peptides (D4, D6, D9, E1, E3, E4, E5, E6, and E8) were resynthezided and tested for binding to K-Ras in solution. Peptides selected from library II showed only moderately improved binding affinities over peptide 2, with $K_D$ values of 1.1 μM-6 μM (Table 7). Peptide 11 [bicyclo (A-dL-Phg-R-dN-Pra-I-D-K-FNalR$_4$-Dap-K] showed the highest affinity toward K-Ras (1.1 μM) and was chosen for further optimization.

TABLE 7

Binding affinities of peptide selected from library II toward K-Ras.

| Peptide | Sequence | SEQ ID NO. | $K_D$ (μM) |
|---|---|---|---|
| 9 | bicyclo(d-Ala-Abu-Phg-Arg-d-Asn-Pra-Ile-Abu-K-FNalR$_4$-Dap)-K | 83 | 2.5 |
| 10 | bicyclo(Phg-Ile-Phg-Arg-d-Asn-Pra-Ile-Abu-K-FNalR$_4$-Dap)-K | 84 | 2.4 |
| 11 | bicyclo(Ala-d-Leu-Phg-Arg-d-Asn-Pra-Ile-Asp-K-FNalR$_4$-Dap)-K | 85 | 1.1 |
| 12 | bicyclo(d-Ala-Gln-Phg-Arg-d-Asn-Pra-Ile-Asp-K-FNalR$_4$-Dap)-K | 86 | 2 |
| 13 | bicyclo(Ala-Orn-Phg-Arg-d-Asn-Pra-Ile-d-Phe-K-FNalR$_4$-Dap)-K | 87 | 6.3 |
| 14 | bicyclo(d-Ala-Phg-Phg-Arg-d-Asn-Pra-Ile-d-Phe-K-FNalR$_4$-Dap)-K | 88 | 4.9 |

TABLE 7-continued

Binding affinities of peptide selected from library II toward K-Ras.

| Peptide | Sequence | SEQ ID NO. | $K_D$ (µM) |
|---|---|---|---|
| 18 | bicyclo(d-Ala-Abu-Phg-Arg-d-Asn-Pra-Ile-Abu-K-FNalR$_4$-Dap)-K | 89 | NT |
| 19 | bicyclo(Ala-Ala-Phg-Arg-d-Asn-Pra-Ile-Ala-K-FNalR$_4$-Dap)-K | 90 | NT |
| 20 | bicyclo(Ala-Ala-Phg-Arg-d-Asn-Pra-Ile-Ala-K-FNalR$_4$-Dap)-K | 91 | 4 |

NT = not tested

Peptides 8 and 11 were subjected to a conventional medicinal chemistry SAR campaign, by making conservative substitutions (e.g., Ile to Leu, d-Asn to d-Asp). It was found that replacement of the Phg residue proved to be fruitful. For example, substitution of Phe for the Phg residues in peptide 8 and 11, resulted in peptides 29 and 41, which have $K_D$ values of 0.8 and 0.3 µM for K-Ras, respectively (Table 8).

TABLE 8

Binding affinities of peptide 29 and 41

| Peptide | Sequence | SEQ ID NO. | $K_D$ (µM) |
|---|---|---|---|
| 29 | bicyclo(Ala-Ala-Phe-Arg-d-Asn-Pra-Ile-Ala-K-FNalR$_4$-Dap)-K | 92 | 0.8 |
| 41 | bicyclo(Ala-d-Leu-Phe-Arg-d-Asn-Pra-Ile-Asp-K-FNalR$_4$-Dap)-K | 93 | 0.3 |

Peptide 41 is Biologically Active

Figure 18:
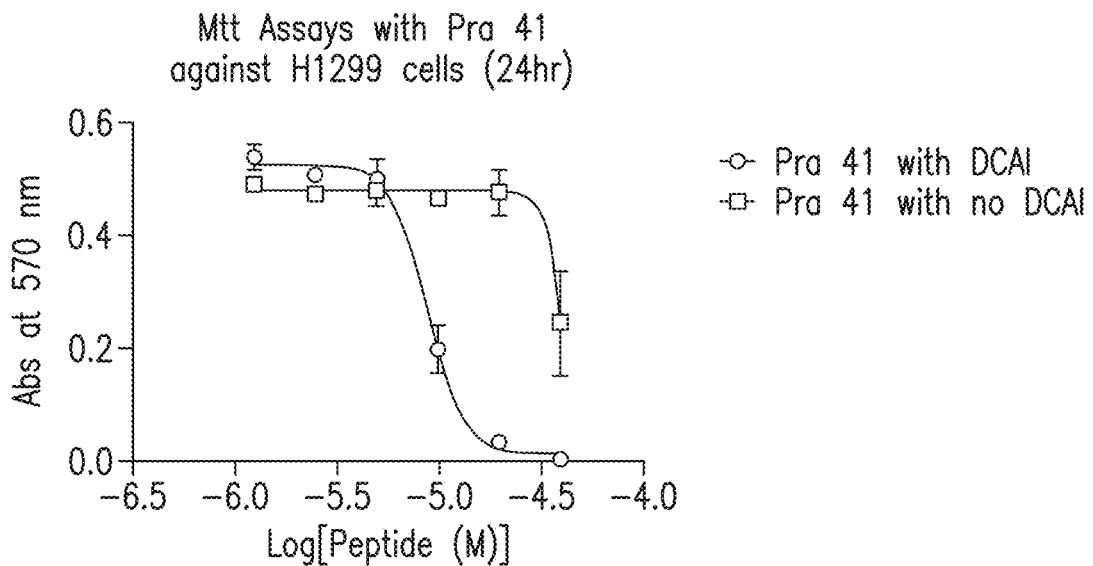
FIG. 18 displays the anti-proliferative properties of peptide 41 against H1299 cells measured by 24-hour MTT assays.
Figure 19:
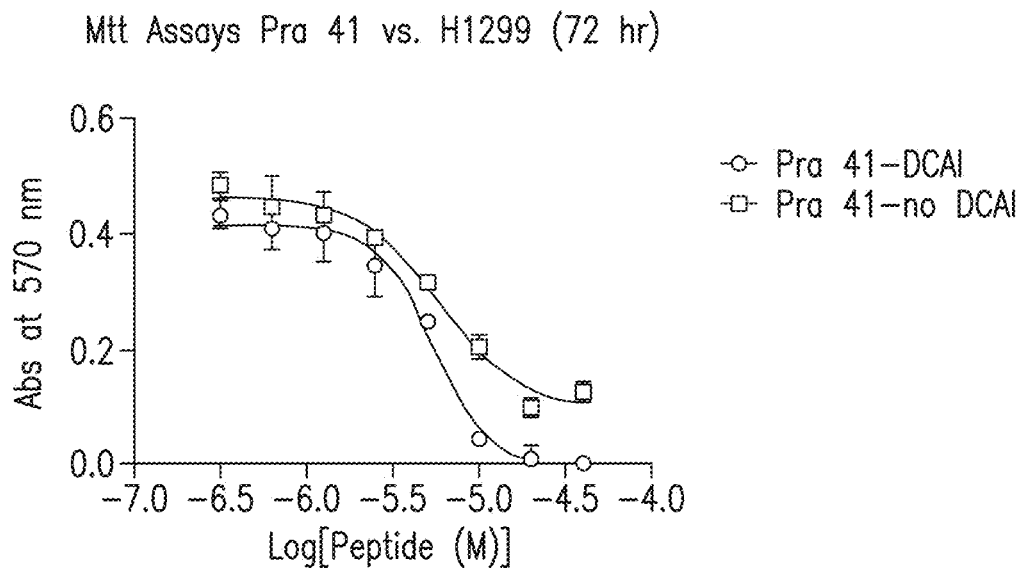
FIG. 19 displays the anti-proliferative properties of peptide 41 against H1299 cells measured by 72-hour MTT assays.

Peptide 41 was evaluated for anti-proliferative activity against H1299 lung cancer cells by MTT proliferation assays. One hundred µL of H1299 cells ($0.5 \times 10^5$ cells/mL) were placed in each well of a 96-well culture plate and allowed to grow overnight. Varying concentrations of peptide 41 (0-40 µM) were added to the each well and the cells were incubated at 37° C. with 5% $CO_2$ for 24-72 h. Ten µL of a MTT stock solution (5 mg/ml) was added into each well. The plate was incubated at 37° C. for 4 h. Then 100 µL of SDS-HCl solubilizing buffer was added into each well, and the resulting solution was mixed thoroughly. The plate was incubated at 37° C. overnight. The absorbance of the formazan product was measured at 570 nm using a Molecular Devices Spectramax M5 plate reader. Cells treated with DMSO were used as control. Peptide 41 showed moderate anti-proliferative activity with an $ED_{50}$ of ~9 µM (FIG. 18). Under the same conditions, a control peptide which lacks the DCAI moiety but is otherwise identical to peptide 41 showed an $ED_{50}>40$ µM after the 24-hour treatment. After 72 h, peptide 41 inhibited cell growth with an $ED_{50}$~7 µM. The control peptide also exhibited moderate cellular toxicity, but was again less potent than peptide 41 (FIG. 19).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A compound of Formula I-A:

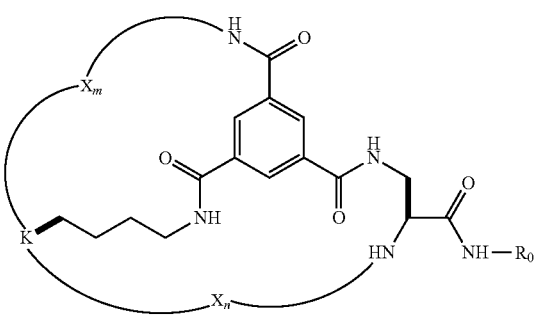

I-A wherein $X_m$ and $X_n$ independently comprise a sequence of 1-10 amino acids;

$R^0$ is selected from hydrogen, substituted or unsubstituted $C_1$-$C_6$ alkyl, or linker to solid phase support; and K has a structure represented by a formula:

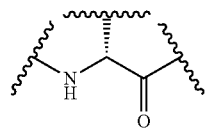

2. The compound of claim 1, wherein $X_m$ and $X_n$ comprise different amino acid sequences.

3. The compound of claim 1, wherein $X_m$ comprises 3-7 residues.

4. The compound of claim 1, wherein $X_m$ comprises 4-6 residues.

5. The compound of claim 1, wherein $X_n$ comprises 2-6 residues.

6. The compound of claim 1, wherein $X_n$ comprises 3-5 residues.

7. The compound of claim 1, wherein the amino acid residues in $X_n$, $X_m$, or both $X_n$ and $X_m$ are all natural amino acids.

8. The compound of claim 1, wherein the compound has a molecular weight of 500-5000.

9. The compound of claim 1, wherein the compound is of Formula I-A-1:

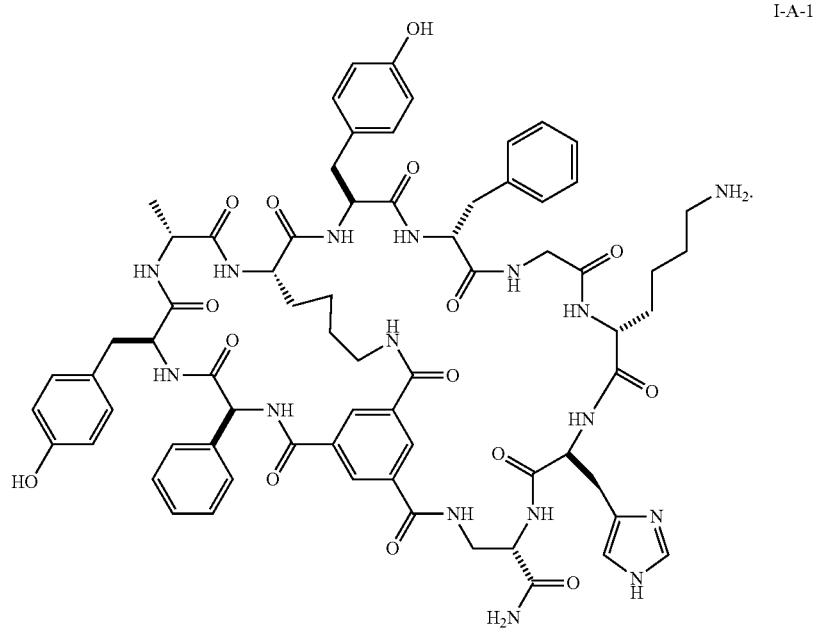

I-A-1

10. The compound of claim 1, wherein the compound is of Formula I-A-2:

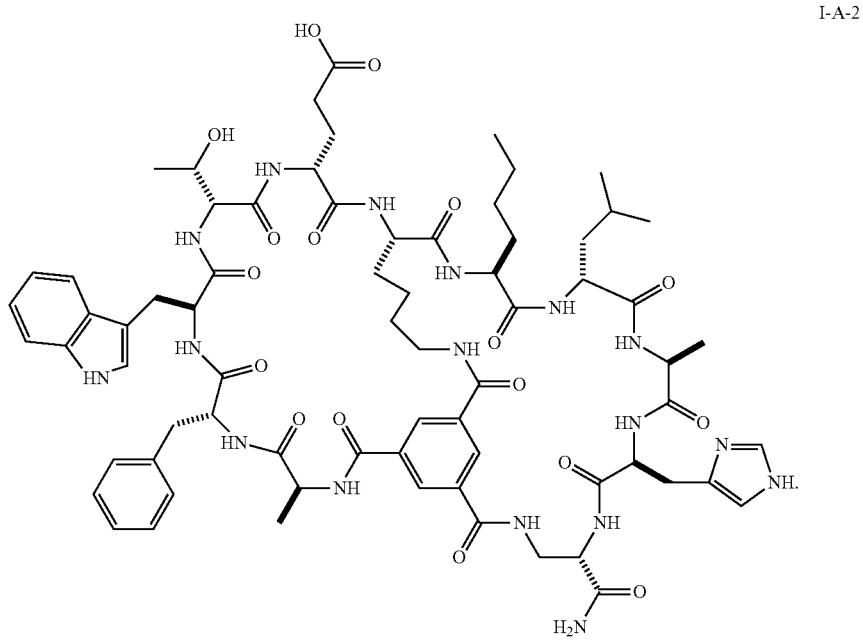

I-A-2

11. A compound comprising:
a. a residue of trimesic acid, the residue bearing three carboxyl functionalities;
b. a lysine residue covalently bonded to the first carboxyl functionality of the trimesic acid residue;
c. a first peptide chain of 1-10 amino acid residues, $X_m$, covalently bonded to the second carboxyl functionality of the trimesic acid residue and to the lysine residue; and
d. a second peptide chain of 1-10 amino acid residues, $X_n$, covalently bonded to the third carboxyl functionality of the trimesic acid residue and to the lysine residue.

12. The compound of claim 11, wherein the first peptide chain comprises 3-7 residues.

13. The compound of claim 11, wherein the second peptide chain comprises 2-6 residues.

14. The compound of claim 11, wherein all of the residues in the first peptide chain, the second peptide chain, or both the first and second peptide chains are natural amino acids.

15. The compound of claim 11, wherein the compound has a molecular weight between 500 and 5000.

16. The compound of claim 1, wherein $X_m$ and $X_n$ are selected from SEQ ID NO.:"1-4 and 6-63".

17. The compound of claim 1, wherein $X_m$ and $X_n$ are selected from SEQ ID NO.:"1-4 and 6-25".

18. The compound of claim 11, wherein $X_m$ and $X_n$ are selected from SEQ ID NO.:"1-4 and 6-63".

19. The compound of claim 11, wherein $X_m$ and $X_n$ are selected from SEQ ID NO.:"1-4 and 6-25".

\* \* \* \* \*

SEQUENCE LISTING

```
<160> NUMBER OF SEQ ID NOS: 100

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

His Lys Gly Phe Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Ala Phe Trp Thr Glu
1               5

<210> SEQ ID NO 3
<211> LENGTH: 4
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Nle

<400> SEQUENCE: 3

His Ala Leu Xaa
1

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (10)..(10)
<223> OTHER INFORMATION: 2,3-diaminopropionic acid

<400> SEQUENCE: 4

Xaa Tyr Ala Lys Tyr Phe Gly Lys His Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Nle
<220> FEATURE:
<221> NAME/KEY: MISC_FEATURE
<222> LOCATION: (11)..(11)
<223> OTHER INFORMATION: 2,3-diaminopropionic acid

<400> SEQUENCE: 5

Ala Phe Trp Thr Glu Lys Xaa Leu Ala His Xaa
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: 2,3-diaminopropionic acid
<220> FEATURE:
<221> NAME/KEY: MISC_FEATURE
<222> LOCATION: (8)..(8)
<223> OTHER INFORMATION: 2,3-diaminopropionic acid

<400> SEQUENCE: 6

Phe Xaa Ser Val Pro Tyr His Xaa
1               5
```

```
<210> SEQ ID NO 7
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: 2,3-diaminopropionic acid

<400> SEQUENCE: 7

Trp Phe Asp Lys Phe Asn His Xaa
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: D-naphthylalanine
<220> FEATURE:
<221> NAME/KEY: MISC_FEATURE
<222> LOCATION: (4)..(4)
<223> OTHER INFORMATION: D-naphthylalanine
<220> FEATURE:
<221> NAME/KEY: MISC_FEATURE
<222> LOCATION: (10)..(10)
<223> OTHER INFORMATION: 2,3-diaminopropionic acid

<400> SEQUENCE: 8

Xaa Ser Gln Xaa Lys Phe Arg Val Arg Xaa
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: D-naphthylalanine
<220> FEATURE:
<221> NAME/KEY: MISC_FEATURE
<222> LOCATION: (5)..(5)
<223> OTHER INFORMATION: 4-fluorophenylalanine
<220> FEATURE:
<221> NAME/KEY: MISC_FEATURE
<222> LOCATION: (8)..(8)
<223> OTHER INFORMATION: D-glutamine
<220> FEATURE:
<221> NAME/KEY: MISC_FEATURE
<222> LOCATION: (10)..(10)
<223> OTHER INFORMATION: 2,3-diaminopropionic acid

<400> SEQUENCE: 9

Arg Arg Xaa Arg Xaa Lys Phe Xaa Gly Xaa
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (3)..(3)
<223> OTHER INFORMATION: D-naphthylalanine
<220> FEATURE:
<221> NAME/KEY: MISC_FEATURE
<222> LOCATION: (5)..(5)
<223> OTHER INFORMATION: 4-fluorophenylalanine
<220> FEATURE:
<221> NAME/KEY: MISC_FEATURE
<222> LOCATION: (10)..(10)
<223> OTHER INFORMATION: 2,3-diaminopropionic acid

<400> SEQUENCE: 10

Gln Arg Xaa Arg Xaa Lys Phe Gln Gly Xaa
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(4)
<223> OTHER INFORMATION: Propargylglycine or acetylated leucine

<400> SEQUENCE: 11

Arg Xaa Xaa Xaa Phe Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (4)..(4)
<223> OTHER INFORMATION: Propargylglycine or acetylated leucine

<400> SEQUENCE: 12

Arg Asp Xaa Xaa Asn Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Propargylglycine or acetylated leucine

<400> SEQUENCE: 13

Xaa Xaa Pro Gly Ala Lys
1               5
```

```
<210> SEQ ID NO 14
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Propargylglycine or acetylated leucine

<400> SEQUENCE: 14

Xaa Xaa Ala Ser Ala Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Propargylglycine or acetylated leucine
<220> FEATURE:
<221> NAME/KEY: MISC_FEATURE
<222> LOCATION: (5)..(5)
<223> OTHER INFORMATION: D-threonine

<400> SEQUENCE: 15

Xaa Xaa Leu Pro Xaa Lys
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (4)..(4)
<223> OTHER INFORMATION: Propargylglycine or acetylated leucine

<400> SEQUENCE: 16

Xaa Arg Asn Xaa Ile Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Propargylglycine or acetylated leucine

<400> SEQUENCE: 17

Xaa Thr Glu Ala Asn Lys
1               5
```

```
<210> SEQ ID NO 18
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Propargylglycine or acetylated leucine
<220> FEATURE:
<221> NAME/KEY: MISC_FEATURE
<222> LOCATION: (2)..(2)
<223> OTHER INFORMATION: D-naphthylalanine

<400> SEQUENCE: 18

Xaa Xaa Val Gly Gln Lys
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Propargylglycine or acetylated leucine
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: MISC_FEATURE
<222> LOCATION: (4)..(5)
<223> OTHER INFORMATION: Propargylglycine or acetylated leucine

<400> SEQUENCE: 19

Xaa Xaa Ser Xaa Xaa Lys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Propargylglycine or acetylated leucine
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: MISC_FEATURE
<222> LOCATION: (5)..(5)
<223> OTHER INFORMATION: Propargylglycine or acetylated leucine

<400> SEQUENCE: 20

Xaa Xaa Met Ser Xaa Lys
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (1)..(1)
<223> OTHER INFORMATION: Propargylglycine or acetylated leucine
<220> FEATURE:
<221> NAME/KEY: MISC_FEATURE
<222> LOCATION: (4)..(4)
<223> OTHER INFORMATION: Propargylglycine or acetylated leucine

<400> SEQUENCE: 21

Xaa Ser Met Xaa Gly Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Propargylglycine or acetylated leucine
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (4)..(5)
<223> OTHER INFORMATION: Propargylglycine or acetylated leucine

<400> SEQUENCE: 22

Xaa Ser Xaa Xaa Xaa Lys
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Propargylglycine or acetylated leucine

<400> SEQUENCE: 23

Xaa Arg Val Asp Ala Lys
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (4)..(4)
<223> OTHER INFORMATION: Propargylglycine

<400> SEQUENCE: 24

Arg Asp Xaa Xaa Asn
1               5
```

```
<210> SEQ ID NO 25
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-naphthylalanine
<220> FEATURE:
<221> NAME/KEY: MISC_FEATURE
<222> LOCATION: (7)..(7)
<223> OTHER INFORMATION: 2,3-diaminopropionic acid

<400> SEQUENCE: 25

Phe Xaa Arg Arg Arg Arg Xaa
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (4)..(4)
<223> OTHER INFORMATION: Propargylglycine

<400> SEQUENCE: 26

Xaa Arg Asn Xaa Ile
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Propargylglycine
<220> FEATURE:
<221> NAME/KEY: MISC_FEATURE
<222> LOCATION: (3)..(3)
<223> OTHER INFORMATION: Phenylglycine

<400> SEQUENCE: 27

Xaa Ser Xaa Lys Lys
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Propargylglycine

<400> SEQUENCE: 28

Xaa Arg Val Asp Ala
1               5
```

```
<210> SEQ ID NO 29
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: MISC_FEATURE
<222> LOCATION: (5)..(5)
<223> OTHER INFORMATION: Propargylglycine

<400> SEQUENCE: 29

Ala Xaa Arg Asn Xaa Ile
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (4)..(4)
<223> OTHER INFORMATION: Propargylglycine

<400> SEQUENCE: 30

Xaa Arg Asn Xaa Ile Ala
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: MISC_FEATURE
<222> LOCATION: (5)..(5)
<223> OTHER INFORMATION: Propargylglycine

<400> SEQUENCE: 31

Ala Xaa Arg Asn Xaa Ile Ala
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine
```

```
<400> SEQUENCE: 32

Ala Ala Xaa Arg Asn Xaa Ile Ala
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine

<400> SEQUENCE: 33

Ala Phe Xaa Arg Asn Xaa Ile Ala
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Abu
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MOD_RES
<222> LOCATION: (8)..(8)
<223> OTHER INFORMATION: Abu

<400> SEQUENCE: 34

Ala Xaa Xaa Arg Asn Xaa Ile Xaa
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MOD_RES
<222> LOCATION: (8)..(8)
<223> OTHER INFORMATION: Abu
```

```
<400> SEQUENCE: 35

Xaa Ile Xaa Arg Asn Xaa Ile Xaa Lys
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Phenylglycine
<220> FEATURE:
<221> NAME/KEY: MISC_FEATURE
<222> LOCATION: (5)..(5)
<223> OTHER INFORMATION: Propargylglycine
<220> FEATURE:
<221> NAME/KEY: MOD_RES
<222> LOCATION: (7)..(7)
<223> OTHER INFORMATION: Abu

<400> SEQUENCE: 36

Xaa Xaa Arg Asn Xaa Ile Xaa
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-leucine
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine

<400> SEQUENCE: 37

Ala Xaa Xaa Arg Asn Xaa Ile Asp
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine

<400> SEQUENCE: 38

Ala Gln Xaa Arg Asn Xaa Ile Asp
1               5
```

```
<210> SEQ ID NO 39
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine

<400> SEQUENCE: 39

Ile Glu Xaa Arg Asn Xaa Ile Asp
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine

<400> SEQUENCE: 40

Ala Ser Xaa Arg Asn Xaa Ile Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: MISC_FEATURE
<222> LOCATION: (5)..(5)
<223> OTHER INFORMATION: Propargylglycine

<400> SEQUENCE: 41

Leu Xaa Arg Asn Xaa Ile Glu
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine
```

```
<400> SEQUENCE: 42

Ala Xaa Xaa Arg Asn Xaa Ile Phe
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: misc_feature
<222> LOCATION: (7)..(7)
<223> OTHER INFORMATION: Xaa can be any naturally occurring amino acid

<400> SEQUENCE: 43

Ala Xaa Xaa Arg Asn Xaa Xaa Ile Phe
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Abu
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine

<400> SEQUENCE: 44

Ala Xaa Xaa Arg Asn Xaa Ile Asn
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: D-alanine
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine
```

```
<400> SEQUENCE: 45

Xaa Ala Xaa Arg Asn Xaa Ile Asn
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine

<400> SEQUENCE: 46

Xaa Asn Xaa Arg Asn Xaa Ile Ile
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Abu
<220> FEATURE:
<221> NAME/KEY: MISC_FEATURE
<222> LOCATION: (3)..(3)
<223> OTHER INFORMATION: Xaa = Phenylglycine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MOD_RES
<222> LOCATION: (8)..(8)
<223> OTHER INFORMATION: Nle

<400> SEQUENCE: 47

Ala Xaa Xaa Arg Asn Xaa Ile Xaa
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: MISC_FEATURE
<222> LOCATION: (5)..(5)
<223> OTHER INFORMATION: Propargylglycine
<220> FEATURE:
<221> NAME/KEY: MISC_FEATURE
<222> LOCATION: (7)..(7)
<223> OTHER INFORMATION: Phenylglycine
```

```
<400> SEQUENCE: 48

Trp Xaa Arg Asn Xaa Ile Xaa
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Propargylglycine

<400> SEQUENCE: 49

Ala Asn Xaa Arg Asn Xaa Ile Arg
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Nle
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine

<400> SEQUENCE: 50

Arg Xaa Xaa Arg Asn Xaa Ile Ser
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: MISC_FEATURE
<222> LOCATION: (5)..(5)
<223> OTHER INFORMATION: Propargylglycine
<220> FEATURE:
<221> NAME/KEY: MISC_FEATURE
<222> LOCATION: (10)..(10)
<223> OTHER INFORMATION: D-naphthylalanine

<400> SEQUENCE: 51

His Xaa Arg Asn Xaa Ile Tyr Lys Phe Xaa
1               5                   10
```

```
<210> SEQ ID NO 52
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Abu
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MOD_RES
<222> LOCATION: (8)..(8)
<223> OTHER INFORMATION: Abu

<400> SEQUENCE: 52

Ala Xaa Xaa Arg Asn Xaa Ile Xaa
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MOD_RES
<222> LOCATION: (8)..(8)
<223> OTHER INFORMATION: Abu

<400> SEQUENCE: 53

Xaa Ile Xaa Arg Asn Xaa Ile Xaa
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Propargylglycine
```

```
<400> SEQUENCE: 54

Ala Leu Xaa Arg Asn Xaa Ile Asp
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Propargylglycine

<400> SEQUENCE: 55

Ala Gln Xaa Arg Asn Xaa Ile Asp
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine

<400> SEQUENCE: 56

Ala Xaa Xaa Arg Asn Xaa Ile Phe
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine

<400> SEQUENCE: 57

Ala Xaa Xaa Arg Asn Xaa Ile Phe
1               5
```

```
<210> SEQ ID NO 58
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Abu
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MOD_RES
<222> LOCATION: (8)..(8)
<223> OTHER INFORMATION: Abu

<400> SEQUENCE: 58

Ala Xaa Xaa Arg Asn Xaa Ile Xaa
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Propargylglycine

<400> SEQUENCE: 59

Ala Ala Xaa Arg Asn Xaa Ile Ala
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Propargylglycine

<400> SEQUENCE: 60

Ala Ala Phe Arg Asn Xaa Ile Ala
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (6)..(6)
<223> OTHER INFORMATION: Propargylglycine

<400> SEQUENCE: 61

Ala Leu Phe Arg Asn Xaa Ile Asp
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine

<400> SEQUENCE: 62

Xaa Tyr Ala Lys Tyr Phe Gly Lys His
1               5

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Nle

<400> SEQUENCE: 63

Ala Phe Trp Thr Glu Lys Xaa Leu Ala His
1               5                   10

<210> SEQ ID NO 64
<211> LENGTH: 32
<212> TYPE: DNA
<213> ORGANISM: Artificial Sequence
<220> FEATURE:
<223> OTHER INFORMATION: Synthetic Construct

<400> SEQUENCE: 64
catctcgagt cacagggcaa tgatcccaaa gt                                    32

<210> SEQ ID NO 65
<211> LENGTH: 33
<212> TYPE: DNA
<213> ORGANISM: Artificial Sequence
<220> FEATURE:
<223> OTHER INFORMATION: Synthetic Construct

<400> SEQUENCE: 65
caccgcaagc ttgtcagatc atcttctcga acc                                   33

<210> SEQ ID NO 66
<211> LENGTH: 13
<212> TYPE: PRT
<213> ORGANISM: Artificial Sequence
<220> FEATURE:
<223> OTHER INFORMATION: Synthetic Construct
```

```
<400> SEQUENCE: 66

Met Val Leu Asp Ser Leu Glu Phe Ile Ala Ser Lys Leu
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (13)..(13)
<223> OTHER INFORMATION: 2,3-diaminopropionic acid

<400> SEQUENCE: 67

Xaa Tyr Asp Ala Lys Tyr Asp Phe Gly Asp Lys His Xaa
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Nle
<220> FEATURE:
<221> NAME/KEY: MISC_FEATURE
<222> LOCATION: (14)..(14)
<223> OTHER INFORMATION: 2,3-diaminopropionic acid

<400> SEQUENCE: 68

Ala Asp Phe Trp Asp Thr Gln Lys Xaa Asp Leu Ala His Xaa
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: napthylalanine
<220> FEATURE:
<221> NAME/KEY: MISC_FEATURE
<222> LOCATION: (7)..(7)
<223> OTHER INFORMATION: 2,3-diaminopropionic acid
<220> FEATURE:
<221> NAME/KEY: MISC_FEATURE
<222> LOCATION: (9)..(9)
<223> OTHER INFORMATION: D-Valine
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MISC_FEATURE
<222> LOCATION: (13)..(13)
<223> OTHER INFORMATION: 2,3-diaminopropionic acid

<400> SEQUENCE: 69

Arg Arg Arg Arg Xaa Phe Xaa Ser Xaa Pro Tyr His Xaa
1               5                   10
```

```
<210> SEQ ID NO 70
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: napthylalanine
<220> FEATURE:
<221> NAME/KEY: MISC_FEATURE
<222> LOCATION: (7)..(7)
<223> OTHER INFORMATION: 2,3-diaminopropionic acid
<220> FEATURE:
<221> NAME/KEY: MISC_FEATURE
<222> LOCATION: (9)..(9)
<223> OTHER INFORMATION: D-Valine
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MISC_FEATURE
<222> LOCATION: (13)..(13)
<223> OTHER INFORMATION: 2,3-diaminopropionic acid

<400> SEQUENCE: 70

Arg Arg Arg Arg Xaa Phe Xaa Ser Xaa Pro Tyr His Xaa
1               5                   10

<210> SEQ ID NO 71
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (5)..(5)
<223> OTHER INFORMATION: D-phenylalanine
<220> FEATURE:
<221> NAME/KEY: MISC_FEATURE
<222> LOCATION: (6)..(6)
<223> OTHER INFORMATION: D-asparagine
<220> FEATURE:
<221> NAME/KEY: MISC_FEATURE
<222> LOCATION: (8)..(8)
<223> OTHER INFORMATION: 2,3-diaminopropionic acid

<400> SEQUENCE: 71

Trp Xaa Asp Lys Xaa Xaa His Xaa
1               5

<210> SEQ ID NO 72
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: D-naphthylalanine
<220> FEATURE:
<221> NAME/KEY: MISC_FEATURE
<222> LOCATION: (4)..(4)
<223> OTHER INFORMATION: D-naphthylalanine
```

```
<220> FEATURE:
<221> NAME/KEY: MISC_FEATURE
<222> LOCATION: (5)..(5)
<223> OTHER INFORMATION: Phenylglycine
<220> FEATURE:
<221> NAME/KEY: MISC_FEATURE
<222> LOCATION: (7)..(7)
<223> OTHER INFORMATION: D-phenylalanine
<220> FEATURE:
<221> NAME/KEY: MISC_FEATURE
<222> LOCATION: (9)..(9)
<223> OTHER INFORMATION: D-Valine
<220> FEATURE:
<221> NAME/KEY: MISC_FEATURE
<222> LOCATION: (11)..(11)
<223> OTHER INFORMATION: 2,3-diaminopropionic acid

<400> SEQUENCE: 72

Xaa Ser Gln Xaa Xaa Lys Xaa Arg Xaa Arg Xaa
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: D-naphthylalanine
<220> FEATURE:
<221> NAME/KEY: MISC_FEATURE
<222> LOCATION: (5)..(5)
<223> OTHER INFORMATION: 4-fluorophenylalanine
<220> FEATURE:
<221> NAME/KEY: MISC_FEATURE
<222> LOCATION: (7)..(7)
<223> OTHER INFORMATION: D-phenylalanine
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: 2,3-diaminopropionic acid

<400> SEQUENCE: 73

Arg Arg Xaa Arg Xaa Lys Xaa Gly Xaa
1               5

<210> SEQ ID NO 74
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Orn
<220> FEATURE:
<221> NAME/KEY: MISC_FEATURE
<222> LOCATION: (3)..(3)
<223> OTHER INFORMATION: D-naphthylalanine
<220> FEATURE:
<221> NAME/KEY: MISC_FEATURE
<222> LOCATION: (5)..(5)
<223> OTHER INFORMATION: 4-fluorophenylalanine
```

```
<220> FEATURE:
<221> NAME/KEY: MISC_FEATURE
<222> LOCATION: (7)..(7)
<223> OTHER INFORMATION: D-phenylalanine
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (10)..(10)
<223> OTHER INFORMATION: 2,3-diaminopropionic acid

<400> SEQUENCE: 74

Xaa Arg Xaa Arg Xaa Lys Xaa Xaa Gly Xaa
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (4)..(4)
<223> OTHER INFORMATION: Propargylglycine
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (8)..(8)
<223> OTHER INFORMATION: D-naphthylalanine
<220> FEATURE:
<221> NAME/KEY: MISC_FEATURE
<222> LOCATION: (13)..(13)
<223> OTHER INFORMATION: 2,3-diaminopropionic acid

<400> SEQUENCE: 75

Arg Asp Xaa Xaa Xaa Lys Phe Xaa Arg Arg Arg Arg Xaa Lys
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (3)..(3)
<223> OTHER INFORMATION: D-asparagine
<220> FEATURE:
<221> NAME/KEY: MISC_FEATURE
<222> LOCATION: (4)..(4)
<223> OTHER INFORMATION: Propargylglycine
<220> FEATURE:
<221> NAME/KEY: MISC_FEATURE
<222> LOCATION: (8)..(8)
<223> OTHER INFORMATION: D-naphthylalanine
<220> FEATURE:
<221> NAME/KEY: MISC_FEATURE
<222> LOCATION: (13)..(13)
<223> OTHER INFORMATION: 2,3-diaminopropionic acid
```

```
<400> SEQUENCE: 76

Xaa Arg Xaa Xaa Ile Lys Phe Xaa Arg Arg Arg Arg Xaa Lys
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Propargylglycine
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MOD_RES
<222> LOCATION: (4)..(5)
<223> OTHER INFORMATION: ACETYLATION
<220> FEATURE:
<221> NAME/KEY: MISC_FEATURE
<222> LOCATION: (8)..(8)
<223> OTHER INFORMATION: D-naphthylalanine
<220> FEATURE:
<221> NAME/KEY: MISC_FEATURE
<222> LOCATION: (13)..(13)
<223> OTHER INFORMATION: 2,3-diaminopropionic acid

<400> SEQUENCE: 77

Xaa Ser Xaa Lys Lys Lys Phe Xaa Arg Arg Arg Arg Xaa Lys
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Propargylglycine
<220> FEATURE:
<221> NAME/KEY: MISC_FEATURE
<222> LOCATION: (3)..(3)
<223> OTHER INFORMATION: D-valine
<220> FEATURE:
<221> NAME/KEY: MISC_FEATURE
<222> LOCATION: (8)..(8)
<223> OTHER INFORMATION: D-naphthylalanine
<220> FEATURE:
<221> NAME/KEY: MISC_FEATURE
<222> LOCATION: (13)..(13)
<223> OTHER INFORMATION: 2,3-diaminopropionic acid

<400> SEQUENCE: 78

Xaa Arg Xaa Asp Ala Lys Phe Xaa Arg Arg Arg Arg Xaa Lys
1               5                   10

<210> SEQ ID NO 79
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
```

```
<220> FEATURE:
<221> NAME/KEY: MISC_FEATURE
<222> LOCATION: (4)..(4)
<223> OTHER INFORMATION: D-asparagine
<220> FEATURE:
<221> NAME/KEY: MISC_FEATURE
<222> LOCATION: (5)..(5)
<223> OTHER INFORMATION: Propargylglycine
<220> FEATURE:
<221> NAME/KEY: MISC_FEATURE
<222> LOCATION: (9)..(9)
<223> OTHER INFORMATION: D-naphthylalanine
<220> FEATURE:
<221> NAME/KEY: MISC_FEATURE
<222> LOCATION: (14)..(14)
<223> OTHER INFORMATION: 2,3-diaminopropionic acid

<400> SEQUENCE: 79

Ala Xaa Arg Xaa Xaa Ile Lys Phe Xaa Arg Arg Arg Arg Xaa Lys
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (3)..(3)
<223> OTHER INFORMATION: D-asparagine
<220> FEATURE:
<221> NAME/KEY: MISC_FEATURE
<222> LOCATION: (4)..(4)
<223> OTHER INFORMATION: Propargylglycine
<220> FEATURE:
<221> NAME/KEY: MISC_FEATURE
<222> LOCATION: (9)..(9)
<223> OTHER INFORMATION: D-naphthylalanine
<220> FEATURE:
<221> NAME/KEY: MISC_FEATURE
<222> LOCATION: (14)..(14)
<223> OTHER INFORMATION: 2,3-diaminopropionic acid

<400> SEQUENCE: 80

Xaa Arg Xaa Xaa Ile Ala Lys Phe Xaa Arg Arg Arg Arg Xaa Lys
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Phenylglycine
<220> FEATURE:
<221> NAME/KEY: MISC_FEATURE
<222> LOCATION: (4)..(4)
<223> OTHER INFORMATION: D-asparagine
<220> FEATURE:
<221> NAME/KEY: MISC_FEATURE
<222> LOCATION: (5)..(5)
<223> OTHER INFORMATION: Propargylglycine
<220> FEATURE:
<221> NAME/KEY: MISC_FEATURE
<222> LOCATION: (10)..(10)
<223> OTHER INFORMATION: D-naphthylalanine
```

```
<220> FEATURE:
<221> NAME/KEY: MISC_FEATURE
<222> LOCATION: (15)..(15)
<223> OTHER INFORMATION: 2,3-diaminopropionic acid

<400> SEQUENCE: 81

Ala Xaa Arg Xaa Xaa Ile Ala Lys Phe Xaa Arg Arg Arg Arg Xaa Lys
1               5                   10                  15

<210> SEQ ID NO 82
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 82

Ala Ala Xaa Arg Xaa Xaa Ile Ala Lys Phe Xaa Arg Arg Arg Arg Xaa
1               5                   10                  15

Lys

<210> SEQ ID NO 83
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: D-alanine
<220> FEATURE:
<221> NAME/KEY: MOD_RES
<222> LOCATION: (2)..(2)
<223> OTHER INFORMATION: Abu
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MOD_RES
<222> LOCATION: (8)..(8)
<223> OTHER INFORMATION: Abu
```

```
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 83

Xaa Xaa Xaa Arg Xaa Xaa Ile Xaa Lys Phe Xaa Arg Arg Arg Arg Xaa
1               5                   10                  15

Lys

<210> SEQ ID NO 84
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Phenylglycine
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MOD_RES
<222> LOCATION: (8)..(8)
<223> OTHER INFORMATION: Abu
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 84

Xaa Ile Xaa Arg Xaa Xaa Ile Xaa Lys Phe Xaa Arg Arg Arg Arg Xaa
1               5                   10                  15

Lys

<210> SEQ ID NO 85
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-leucine
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (5)..(5)
<223> OTHER INFORMATION: D-asparagine
```

```
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 85

Ala Xaa Xaa Arg Xaa Xaa Ile Asp Lys Phe Xaa Arg Arg Arg Arg Xaa
1               5                   10                  15

Lys

<210> SEQ ID NO 86
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: D-alanine
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 86

Xaa Gln Xaa Arg Xaa Xaa Ile Asp Lys Phe Xaa Arg Arg Arg Arg Xaa
1               5                   10                  15

Lys

<210> SEQ ID NO 87
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (5)..(5)
<223> OTHER INFORMATION: D-asparagine
```

```
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MISC_FEATURE
<222> LOCATION: (8)..(8)
<223> OTHER INFORMATION: D-phenylalanine
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 87

Ala Xaa Xaa Arg Xaa Xaa Ile Xaa Lys Phe Xaa Arg Arg Arg Arg Xaa
1               5                   10                  15

Lys

<210> SEQ ID NO 88
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: D-alanine
<220> FEATURE:
<221> NAME/KEY: MISC_FEATURE
<222> LOCATION: (2)..(3)
<223> OTHER INFORMATION: Phenylglycine
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MISC_FEATURE
<222> LOCATION: (8)..(8)
<223> OTHER INFORMATION: D-phenylalanine
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 88

Xaa Xaa Xaa Arg Xaa Xaa Ile Xaa Lys Phe Xaa Arg Arg Arg Arg Xaa
1               5                   10                  15

Lys

<210> SEQ ID NO 89
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: D-alanine
```

```
<220> FEATURE:
<221> NAME/KEY: MOD_RES
<222> LOCATION: (2)..(2)
<223> OTHER INFORMATION: Abu
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MOD_RES
<222> LOCATION: (8)..(8)
<223> OTHER INFORMATION: Abu
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 89

Xaa Xaa Xaa Arg Xaa Xaa Ile Xaa Lys Phe Xaa Arg Arg Arg Arg Xaa
1               5                   10                  15

Lys

<210> SEQ ID NO 90
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 90

Ala Ala Xaa Arg Xaa Xaa Ile Ala Lys Phe Xaa Arg Arg Arg Arg Xaa
1               5                   10                  15

Lys

<210> SEQ ID NO 91
<211> LENGTH: 17
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 91

Ala Ala Xaa Arg Xaa Xaa Ile Ala Lys Phe Xaa Arg Arg Arg Arg Xaa
 1               5                  10                  15

Lys

<210> SEQ ID NO 92
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (6)..(6)
<223> OTHER INFORMATION: Propargylglycine
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: D-asparagine

<400> SEQUENCE: 92

Ala Ala Phe Arg Xaa Xaa Ile Ala Lys Phe Xaa Arg Arg Arg Arg Xaa
 1               5                  10                  15

Lys

<210> SEQ ID NO 93
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-leucine
<220> FEATURE:
<221> NAME/KEY: MISC_FEATURE
<222> LOCATION: (5)..(5)
<223> OTHER INFORMATION: D-asparagine
<220> FEATURE:
<221> NAME/KEY: MISC_FEATURE
<222> LOCATION: (6)..(6)
<223> OTHER INFORMATION: Propargylglycine
```

<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 93

```
Ala Xaa Phe Arg Xaa Xaa Ile Asp Lys Phe Xaa Arg Arg Arg Arg Xaa
1               5                  10                  15

Lys
```

<210> SEQ ID NO 94
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: D-valine
<220> FEATURE:
<221> NAME/KEY: MISC_FEATURE
<222> LOCATION: (6)..(6)
<223> OTHER INFORMATION: 4-fluorophenylalanine
<220> FEATURE:
<221> NAME/KEY: MISC_FEATURE
<222> LOCATION: (7)..(7)
<223> OTHER INFORMATION: D-phenylalanine
<220> FEATURE:
<221> NAME/KEY: MISC_FEATURE
<222> LOCATION: (8)..(8)
<223> OTHER INFORMATION: Xaa = D-naphthylalanine
<220> FEATURE:
<221> NAME/KEY: MISC_FEATURE
<222> LOCATION: (9)..(9)
<223> OTHER INFORMATION: D-alanine
<220> FEATURE:
<221> NAME/KEY: MISC_FEATURE
<222> LOCATION: (11)..(11)
<223> OTHER INFORMATION: 2,3-diaminopropionic acid

<400> SEQUENCE: 94

```
Gln Gln Asp Asp Lys Xaa Asp Xaa Asp Gly Xaa
1               5                  10
```

<210> SEQ ID NO 95
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-naphthylalanine
<220> FEATURE:
<221> NAME/KEY: MISC_FEATURE
<222> LOCATION: (3)..(3)
<223> OTHER INFORMATION: D-leucine
<220> FEATURE:
<221> NAME/KEY: MISC_FEATURE
<222> LOCATION: (5)..(5)
<223> OTHER INFORMATION: D-alanine
<220> FEATURE:
<221> NAME/KEY: MISC_FEATURE
<222> LOCATION: (10)..(10)
<223> OTHER INFORMATION: 2,3-diaminopropionic acid

```
<400> SEQUENCE: 95

Tyr Xaa Xaa Lys Xaa Gln Ala Gly Ser Xaa
1               5                   10

<210> SEQ ID NO 96
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-naphthylalanine

<400> SEQUENCE: 96

Phe Xaa Arg Arg Arg Arg
1               5

<210> SEQ ID NO 97
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: D-naphthylalanine

<400> SEQUENCE: 97

Arg Arg Arg Arg Xaa Phe
1               5

<210> SEQ ID NO 98
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: any amino acid
<220> FEATURE:
<221> NAME/KEY: MISC_FEATURE
<222> LOCATION: (3)..(3)
<223> OTHER INFORMATION: Phenylglycine
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: any amino acid
<220> FEATURE:
<221> NAME/KEY: MISC_FEATURE
<222> LOCATION: (11)..(11)
<223> OTHER INFORMATION: D-naphthylalanine
<220> FEATURE:
<221> NAME/KEY: MISC_FEATURE
<222> LOCATION: (16)..(16)
<223> OTHER INFORMATION: 2,3-diaminopropionic acid

<400> SEQUENCE: 98

Xaa Xaa Xaa Arg Xaa Xaa Ile Xaa Lys Phe Xaa Arg Arg Arg Arg Xaa
1               5                   10                  15
```

```
<210> SEQ ID NO 99
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: phenylglycine
<220> FEATURE:
<221> NAME/KEY: MISC_FEATURE
<222> LOCATION: (2)..(2)
<223> OTHER INFORMATION: D-alanine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: D-phenylalanine
<220> FEATURE:
<221> NAME/KEY: MISC_FEATURE
<222> LOCATION: (8)..(8)
<223> OTHER INFORMATION: D-lysine

<400> SEQUENCE: 99

Xaa Tyr Xaa Lys Tyr Xaa Gly Xaa His
1               5

<210> SEQ ID NO 100
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (4)..(4)
<223> OTHER INFORMATION: D-threonine
<220> FEATURE:
<221> NAME/KEY: MISC_FEATURE
<222> LOCATION: (5)..(5)
<223> OTHER INFORMATION: D-glutamine
<220> FEATURE:
<221> NAME/KEY: MOD_RES
<222> LOCATION: (7)..(7)
<223> OTHER INFORMATION: Nle
<220> FEATURE:
<221> NAME/KEY: MISC_FEATURE
<222> LOCATION: (8)..(8)
<223> OTHER INFORMATION: D-leucine

<400> SEQUENCE: 100

Ala Xaa Trp Xaa Xaa Lys Xaa Xaa Ala His
1               5                   10
```